(12) United States Patent
York et al.

(10) Patent No.: US 11,512,042 B2
(45) Date of Patent: Nov. 29, 2022

(54) ENAMINE COMPOUNDS FOR ABSORBANCE OF ELECTROMAGNETIC ENERGY

(71) Applicant: Commonwealth Scientific and Industrial Research Organisation, Acton (AU)

(72) Inventors: Mark York, Clayton (AU); John Ryan, Clayton (AU)

(73) Assignee: Commonwealth Scientific and Industrial Research Organisation, Acton (AU)

( * ) Notice: Subject to any disclaimer, the term of this patent is extended or adjusted under 35 U.S.C. 154(b) by 0 days.

(21) Appl. No.: 15/518,748

(22) PCT Filed: Dec. 23, 2016

(86) PCT No.: PCT/AU2016/051284
§ 371 (c)(1),
(2) Date: Apr. 12, 2017

(87) PCT Pub. No.: WO2017/106930
PCT Pub. Date: Jun. 29, 2017

(65) Prior Publication Data
US 2018/0022693 A1    Jan. 25, 2018

(30) Foreign Application Priority Data

Dec. 23, 2015 (AU) .............................. 2015905371
Sep. 20, 2016 (AU) .............................. 2016903778

(51) Int. Cl.
| | | |
|---|---|---|
| C07D 209/12 | (2006.01) | |
| C07D 403/14 | (2006.01) | |
| C07D 403/10 | (2006.01) | |
| C07D 403/08 | (2006.01) | |
| A61K 31/405 | (2006.01) | |
| A61K 31/404 | (2006.01) | |
| C07C 225/22 | (2006.01) | |
| A61Q 17/04 | (2006.01) | |
| C09D 5/32 | (2006.01) | |
| A61K 8/41 | (2006.01) | |
| C07C 225/16 | (2006.01) | |
| C07C 229/34 | (2006.01) | |
| C07C 229/60 | (2006.01) | |
| C11D 3/30 | (2006.01) | |
| C07C 255/42 | (2006.01) | |
| C07C 235/78 | (2006.01) | |
| C07C 311/37 | (2006.01) | |

(Continued)

(52) U.S. Cl.
CPC .............. *C07C 225/22* (2013.01); *A61K 8/41* (2013.01); *A61K 8/411* (2013.01); *A61K 8/466* (2013.01); *A61K 8/49* (2013.01); *A61K 8/492* (2013.01); *A61K 8/494* (2013.01); *A61K 8/4906* (2013.01); *A61K 8/4913* (2013.01); *A61K 8/4926* (2013.01); *A61K 8/4953* (2013.01); *A61K 8/585* (2013.01); *A61K 8/70* (2013.01); *A61Q 17/04* (2013.01); *C07C 225/16* (2013.01); *C07C 229/34* (2013.01); *C07C 229/60* (2013.01); *C07C 235/78* (2013.01); *C07C 255/42* (2013.01); *C07C 255/58* (2013.01); *C07C 311/37* (2013.01); *C07D 209/08* (2013.01); *C07D 215/06* (2013.01); *C07D 217/04* (2013.01); *C07D 233/16* (2013.01); *C07D 243/12* (2013.01); *C07D 295/108* (2013.01); *C07F 7/1804* (2013.01); *C08K 5/16* (2013.01); *C08K 5/17* (2013.01); *C08K 5/175* (2013.01); *C08K 5/18* (2013.01); *C08K 5/3412* (2013.01); *C08K 5/3415* (2013.01); *C08K 5/3417* (2013.01); *C08K 5/3432* (2013.01); *C08K 5/3435* (2013.01); *C08K 5/3437* (2013.01); *C08K 5/3442* (2013.01); *C08K 5/3462* (2013.01); *C08K 5/3465* (2013.01); *C08K 5/357* (2013.01); *C09D 5/32* (2013.01); *C09D 7/48* (2018.01); *C09D 133/12* (2013.01); *C11D 3/30* (2013.01); *G02B 1/041* (2013.01); *C08K 5/005* (2013.01); *G02C 7/108* (2013.01)

(58) Field of Classification Search
CPC .. C07D 209/12; C07D 403/14; C07D 403/10; C07D 403/08; A61K 31/405; A61K 31/404
USPC .......... 548/491, 490, 511, 510; 514/419, 415
See application file for complete search history.

(56) References Cited

U.S. PATENT DOCUMENTS

| 3,079,366 A | 2/1963 | Boyle et al. |
|---|---|---|
| 3,365,448 A | 1/1968 | Lesher |

(Continued)

FOREIGN PATENT DOCUMENTS

| BE | 793180 A | 6/1973 |
|---|---|---|
| DE | 2847050 | 5/1980 |

(Continued)

OTHER PUBLICATIONS

STN Registry database entry: CAS RN 88652-92-0 (Entered STN: Nov. 16, 1984). (Year: 1984).*

(Continued)

*Primary Examiner* — Joseph R Kosack
*Assistant Examiner* — Sagar Patel
(74) *Attorney, Agent, or Firm* — Klarquist Sparkman, LLP

(57) ABSTRACT

The present invention describes compounds and uses thereof in applications relating to absorption of electromagnetic energy. Preferred compounds are double bond-containing compounds capable of absorbing electromagnetic radiation energy and having improved properties.

17 Claims, 8 Drawing Sheets

(51) Int. Cl.

| | | |
|---|---|---|
| C08K 5/16 | (2006.01) | |
| C07C 255/58 | (2006.01) | |
| A61K 8/70 | (2006.01) | |
| A61K 8/58 | (2006.01) | |
| C09D 7/48 | (2018.01) | |
| C07D 243/12 | (2006.01) | |
| A61K 8/49 | (2006.01) | |
| C07D 233/16 | (2006.01) | |
| A61K 8/46 | (2006.01) | |
| C07F 7/18 | (2006.01) | |
| C07D 209/08 | (2006.01) | |
| C07D 215/06 | (2006.01) | |
| C07D 217/04 | (2006.01) | |
| C07D 295/108 | (2006.01) | |
| C08K 5/17 | (2006.01) | |
| C08K 5/18 | (2006.01) | |
| C08K 5/3412 | (2006.01) | |
| C08K 5/3415 | (2006.01) | |
| C08K 5/3417 | (2006.01) | |
| C08K 5/3432 | (2006.01) | |
| C08K 5/3435 | (2006.01) | |
| C08K 5/3437 | (2006.01) | |
| C08K 5/3442 | (2006.01) | |
| C08K 5/3462 | (2006.01) | |
| C08K 5/3465 | (2006.01) | |
| C08K 5/357 | (2006.01) | |
| C09D 133/12 | (2006.01) | |
| G02B 1/04 | (2006.01) | |
| G02C 7/10 | (2006.01) | |
| C08K 5/00 | (2006.01) | |

(56) References Cited

U.S. PATENT DOCUMENTS

| | | |
|---|---|---|
| 4,175,087 A | 11/1979 | Abdulla et al. |
| 4,178,449 A | 12/1979 | Dusza et al. |
| 4,273,776 A | 6/1981 | Hoehn |
| 4,364,956 A | 12/1982 | Clark et al. |
| 4,663,156 A | 5/1987 | Clum et al. |
| 5,637,718 A | 6/1997 | Bird et al. |
| 5,731,133 A | 3/1998 | Hubsch et al. |
| 6,042,814 A * | 3/2000 | Koch ............... A61K 8/49 424/400 |
| 2004/0102436 A1 | 5/2004 | Asaki et al. |

FOREIGN PATENT DOCUMENTS

| | | | |
|---|---|---|---|
| DE | 3825382 | 2/1989 | |
| DE | 197 12 033 | 9/1998 | |
| EP | 0123319 A2 * | 10/1984 | ............ C07D 249/08 |
| GB | 1551409 | 8/1979 | |
| JP | 09-052815 | 2/1997 | |
| JP | 2003-186140 A | 7/2003 | |
| JP | 2006257079 A | 9/2006 | |
| WO | WO 02/076946 A2 | 10/2002 | |
| WO | WO 2003/092643 | 11/2003 | |
| WO | WO 2014/082124 | 6/2014 | |
| WO | WO 2015/006803 | 1/2015 | |

OTHER PUBLICATIONS

STN Registry database entry: CAS RN 66521-60-6 (Entered STN: Nov. 16, 1984) (Year: 1984).*
STN Registry database entry: CAS RN 344557-57-9 (Entered STN: Jul. 5, 2001) (Year: 2001).*
Dörwald, F. Zaragoza. Side Reactions in Organic Synthesis: A Guide to Successful Synthesis Design (2005), Weinheim: Wiley-VCH Verlag GmbH & Co. KGaA, Preface. (Year: 2005).*
STN Registry database entry: CAS RN 329762-04-1 (Entered STN: Apr. 3, 2001). (Year: 2001).*
STN Registry database entry: CAS RN 329762-05-2 (Entered STN: Apr. 3, 2001) (Year: 2001).*
STN Caplus Abstract of the European Patent Publication EP-0123319-A2. (Year: 1984).*
Bennett, G., R. Mason, L. Alden and J. Roach, Jr., "Synthesis and antiinflammatory activity of trisubstituted pyrimidines and triazines", J. Med. Chem. (1978), 21(7), pp. 623-628. (Year: 1978).*
Bartnik, R., A. Bensadat, D. Cal, Z. Cebulska, A. Laurent, E. Laurent and C. Rizzon. "A new synthesis of Enaminoketones" Tetrahedron Letters, vol. 37, No. 48, pp. 8751-8754, 1996. (Year: 1996).*
Toome, Voldemar and Karen Manhart, "A simple simultaneous colorimetric determination of primary and secondary amines with fluorescamine", Analytical Letters (1975), 8(7), pp. 441-448. (Year: 1975).*
Arriortua et al., "(E)-3-Dimethylamino-1,2-diphenyl-2-propen-1-one: Structure of an Enaminone," Acta Crystallographica Section C: Crystal Structure, C48(3): 528-530, 1992.
CAS Registry No. RN185389-51-9; STN Entry Date Jan. 23, 1997.
CAS Registry No. RN185389-53-1; STN Entry Date Jan. 23, 1997.
CAS Registry No. RN213534-80-6; STN Entry Date Nov. 1, 1998.
CAS Registry No. RN36777-65-8; STN Entry Date Nov. 16, 1984.
CAS Registry No. RN88652-92-0; STN Entry Date Nov. 16, 1984.
Ciabatonni et al., "Cycloaddition Reaction of Diphenylcyclopropenone with Enamines," Journal of Organic Chemistry, 31(5): 1336-1339, 1966.
International Search Report and Written Opinion issued for International Application No. PCT/AU2016/051284 on Feb. 8, 2017, 16 pages.
CAS Registry Entry No. 102720-93-4, Jun. 14, 1986.
CAS Registry Entry No. 135057-12-4, entry date Jul. 26, 1991.
CAS Registry Entry No. 153495-91-1, entry date Mar. 8, 1994.
CAS Registry Entry No. 343568-15-0, entry date Jun. 27, 2001.
CAS Registry Entry No. 76312-34-0, entry date Nov. 16, 1984.
CAS Registry Entry No. 76312-35-1, entry date Nov. 16, 1984.
CAS Registry Entry No. 864851-39-8, entry date Oct. 10, 2005.
CAS Registry Entry No. 907551-80-8, Sep. 19, 2006.
CAS Registry Entry No. 954379-62-5, entry date Nov. 18, 2007.
Written Opinion issued by Singapore Patent Office for application No. 11201702781Y dated Aug. 21, 2020.
Extended European Search Report issued for EPC Application No. 16847622.4 dated Feb. 26, 2018.
Written Opinion issued for Singapore Application No. 11201702781Y dated Aug. 21, 2019.
CAS Registry No. 405904-60-1, entry date Apr. 18, 2002.
CAS Registry No. 392321-45-8, entry date Feb. 14, 2002.
Bargagna et al., "Reaction of sulfene and dichloroketene with open-chain N,N-Disubstituted α-aminomethyleneketones. Synthesis of N,N-Disubstituted 4-amino-3,4-dihydro-(5-methyl-6-phenyl)(5,6-diphenyl)-1,2-oxathiin 2,2-dioxides and of 4-amino-3-chloro-5-methyl-6-phenyl-2H-pyran-2-ones," vol. 17, pp. 1201-1208, Sep. 1980.
CAS Registry No. 3119-32-2, entry date Nov. 16, 1984.
CAS Registry No. 17059-74-4, entry date Nov. 16, 1984.
CAS Registry No. 72011-31-5, entry date Nov. 16, 1984.
CAS Registry No. 76511-94-9, entry date Nov. 16, 1984.
DUHAMEL et al., "β-lithioenamines. Part 2. Reaction with various electrophiles," J. Chem. Research, 5(9): 222-223, Sep. 1983.
Ostercamp, "Vinylogous Imides. II. Ultraviolet Spectra and the Application of Woodward's Rules," The Journal of Organic Chemistry, 35(5): 1632-1641, May 1970.
Prashad et al., "A convenient synthesis of 3-subsituted 1H-indoles," Synthetic Communications, 25(1): 95-100, Jan. 1995.
Wasserman et al., "Reaction of singlet oxygen with enamino carbonyl systems. A general method for the synthesis of alpha-keto derivatives of lactones, esters, amides, lactams, and ketones," J. Org. Chem., 50(19): 3573-3580, Sep. 1, 1985.
Xiao et al., "Enamines as novel antibacterials and their structure-activity relationships," Eur. J. Med. Chem., vol. 43, pp. 1828-1836, Dec. 8, 2007.

(56) References Cited

OTHER PUBLICATIONS

Yang et al., "Water as an additive for selective synthesis of saturated 1,4-diketones and tetrasubstituted furans directly from 1,4-enediones," *Tetrahedron*, vol. 70, pp. 6733-6741, Jul. 24, 2014.
Zhuo et al., "O NMR spectroscopic study of tertiary enaminones," *Magnetic Resonance in Chemistry*, vol. 34, pp. 595-602, Aug. 1996.
CAS 185389-55-3, entry date Jan. 23, 1997.
CAS 199390-19-7, entry date Jan. 6, 1998.
CAS 213534-80-6, entry date Nov. 1, 1998.
CAS 1346254-65-6, entry date Nov. 23, 2011.
CAS 1346254-67-8, entry date Nov. 23, 2011.
Office Action issued by the Chinese National Intellectual Property Administration for Chinese Application No. 201680004884 dated Apr. 23, 2021 (with English translation).

\* cited by examiner

US 11,512,042 B2

ENAMINE COMPOUNDS FOR ABSORBANCE OF ELECTROMAGNETIC ENERGY

CROSS REFERENCE TO RELATED APPLICATIONS

This is the U.S. National Stage of International Application No. PCT/AU2016/051284, filed Dec. 23, 2016, which was published in English under PCT Article 21(2), which in turn claims the benefit of Australian Application No. 2015905371, filed Dec. 23, 2015 and Australian Application No. 2016903778, filed Sep. 20, 2016.

FIELD OF THE INVENTION

The invention relates to compounds capable of absorbing energy to thereby provide a protective effect. More particularly, this invention relates to compounds for absorbing electromagnetic radiation, uses thereof and compositions comprising said compounds.

BACKGROUND TO THE INVENTION

Any reference to background art herein is not to be construed as an admission that such art constitutes common general knowledge in Australia or elsewhere.

Ultraviolet light (UV) and visible light absorbing or screening compounds have found use in a range of applications where protection from the sun's harmful UV rays is desirable. This includes their use in glass and lens coatings, paints, packaging, household cleaning formulations and materials including fabrics as well as, perhaps most notably, in sun screen formulations to protect the skin of the user from damage caused by UV radiation.

Compounds suitable for absorbing UV light, and therefore offering a protective function, were described in WO 2015/006803 in the name of the present applicant. The compounds disclosed therein displayed a cyclic enaminoketone core with a range of substitutions designed to provide a useful variance in absorption characteristics to provide for coverage throughout the UV range. While effective for their primary purpose the stability of the compounds to exposure to electromagnetic radiation was not considered or discussed in any form.

Inorganic sunscreens, such as zinc oxide, protect from UV primarily by light scattering. Conversely organic sunscreen agents, such as those described in WO 2015/006803, absorb the UV light and must then emit this energy in order to return to the ground state. Such energy loss can occur by any or all of a variety of pathways such as fluorescence, phosphorescence, transfer to another molecule, isomerisation, heat generation or fragmentation. If destructive pathways such as fragmentation, and some isomerisations, predominate then the ability of the molecule to continue to absorb UV or visible light is destroyed. While protective compounds are not required to be indefinitely photostable it is important that they provide for a useful lifetime and so resist fast degradation.

It would therefore be desirable to provide for compounds which can absorb energy from a variety of ranges within the electromagnetic spectrum or which provide for a variety of molar extinction coefficients or mass extinction coefficients or which can demonstrate improved stability to this exposure to provide for a greater operational lifespan.

Further, there is an ongoing need for compounds, whether preferentially photostabilised or not, which provide for improved physical stability. For example, the incorporation of absorbing compounds into lenses and other solid phase polymeric products requires a high level of stability of the compound to the initiating and curing conditions of the polymer.

SUMMARY OF THE INVENTION

It has been found that certain non-cyclic enamine core compounds provide for absorbance across a useful range of the electromagnetic spectrum with a useful variation in molar extinction coefficients or mass extinction coefficients or $\lambda_{max}$ or $\lambda_{crit}$ values; and this variance can, to a significant degree, be tailored based on the choice of functional groups extending from the enamine core. Further, these compounds have been advantageously found to demonstrate both a useful degree of photostability and an improved physical stability or general robustness to a range of conditions, including incorporation into lenses. Finally, while providing these advantages the compounds of the invention, due at least in part to their non-cyclic core, are also easily accessible in a synthetic sense and can be prepared in a short number of steps from readily available building blocks.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

DETAILED DESCRIPTION

Figure 1:
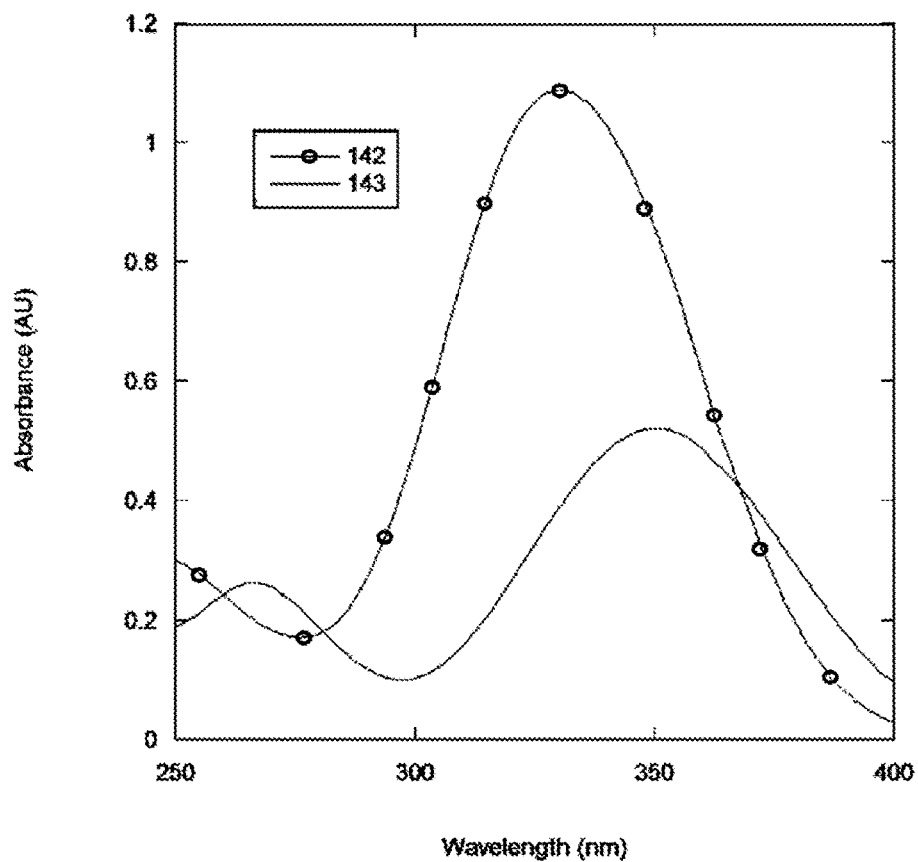
FIG. 1 is a graphical representation of the absorbance of compounds 142 and 143 measured in a 10 mm cuvette as 0.001% solutions in methanol (142 is the uppermost trace at peak point of approximately 330 nm)

The present invention is predicated, at least in part, on the finding that non-cyclic enamine structures provide for effective absorption of electromagnetic radiation across a wide range of the spectrum while at the same time offering a surprising level of stability both in the physical and photostability senses. The use of cyclic enaminoketones in UV absorption is known from WO 2015/006803, in the name of the present applicant, and from older publications such as *International Journal of Cosmetic Science* 20, 41-51 (1998) (Dunlap et al). Dunlap, in one of the earliest disclosures of these MAA compounds stated that the most promising approach to address instability problems with the enaminoketone core was to incorporate the enamine function, i.e. both the double bond and enamine nitrogen atom, into the ring structure itself. Dunlap stated that this modification proved effective in preventing hydrolytic cleavage of the enaminone chromophore. It has thus been accepted wisdom that the enamine core of such compounds had to be built within the ring to achieve both effective absorption and sufficient stability to allow them to be used in absorbing applications. Surprisingly, the present inventors have found that not only is this not the case but in fact many of the present non-cyclic enamine compounds actually show significantly improved stability over related cyclic compounds.

It will be appreciated then that, while to a degree, the present compounds might be viewed as ring-opened forms of the cyclic enamine compounds they in fact show significantly different and advantageous properties which could not be predicted from a comparison with the closest cyclic analogue. That is, there has been demonstrated to be a lack of predictability that deconstructing the enamine ring structure would result in compounds which still absorb electromagnetic radiation effectively and, particularly, which show useful and in some cases greatly improved stability.

The present compounds may have an electron withdrawing group adjacent the carbonyl group. While it is known that electron withdrawing groups can reduce electron density around adjacent functional groups and thereby decrease chemical reactivity, it is important to realise that chemical reactivity is not the same as, and is certainly not predictive of, photostability. The underlying mechanisms of chemical reactivity and photostability (or release of excitation energy upon irradiation) are different with a variety of different considerations. It could therefore not reasonably be predicted with any degree of certainty that a compound which has reduced chemical reactivity due to the presence of an electron withdrawing group would also demonstrate improved photostability and would, at the same time, prove to be an effective absorber of electromagnetic radiation, such as UV and visible light.

According to a first aspect of the present invention, there is provided a compound of formula I, or a salt or isomer thereof:

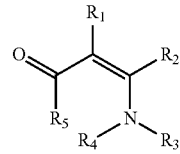

formula I wherein, $R_1$ is selected from the group consisting of $C_1$ to $C_{20}$ alkyl, $C_2$ to $C_{20}$ alkenyl, $C_2$ to $C_{20}$ alkynyl, aryl, heteroaryl, aroyl, $C_5$ to $C_7$ cycloalkenyl and heterocyclic, each of which groups may be substituted or unsubstituted;

$R_2$ is selected from the group consisting of hydrogen, $C_1$ to $C_{12}$ alkyl, $C_2$ to $C_{12}$ alkenyl, aryl, heteroaryl, aroyl, $C_5$ to $C_7$ cycloalkenyl and heterocyclic, each of which groups may be substituted or unsubstituted;

$R_3$ and $R_4$ are independently selected from the group consisting of $C_1$ to $C_{20}$ alkyl, $C_2$ to $C_{20}$ alkenyl, $C_2$ to $C_{20}$ alkynyl, $C_1$ to $C_{20}$ alkylamine, aryl, heteroaryl, aroyl, $C_5$ to $C_7$ cycloalkyl, $C_3$ to $C_8$ cycloalkenyl, $C_2$ to $C_{12}$ alkanoyloxy, haloalkyl, and heterocyclic, all of which groups may be substituted or unsubstituted, or $R_3$ and $R_4$ may together form a cyclic structure which includes the nitrogen atom to which they are attached, said cyclic structure being optionally substituted; and $R_5$ is selected from the group consisting of $C_1$ to $C_{20}$ haloalkyl, $C_1$ to $C_{20}$ haloalkenyl, a fluorine-containing group, $C_1$ to $C_{20}$ alkyl, $C_2$ to $C_{20}$ alkenyl, $C_1$ to $C_{20}$ alkoxy, ester, amide, $C_1$ to $C_{20}$ alkanoyl, $C_1$ to $C_{20}$ alkenoyl, aryl, $C_5$ to $C_7$ cycloalkenyl and heterocyclic, each of which groups may be substituted or unsubstituted.

In any embodiment of the compound of formula I, $R_1$ is selected from the group consisting of $C_2$ to $C_{12}$ alkenyl, $C_2$ to $C_{12}$ alkynyl, $C_5$ or $C_6$ aryl, $C_5$ or $C_6$ heteroaryl, $C_5$ or $C_6$ aroyl, $C_5$ or $C_6$ cycloalkenyl, fused aryl-heterocyclic and $C_5$ or $C_6$ heterocyclic, each of which groups may be substituted or unsubstituted.

In any embodiment of the compound of formula I, $R_1$ is selected from the group consisting of phenyl, pyridyl, pyran, thiopyran, diazine, oxazine, thiazine, dioxine, dithiine, pyrrole, furan, thiophene, imidazole, pyrazole, oxazole, isoxazole, thiazole, isothiazole, indole and isoindole, each of which groups may be substituted or unsubstituted.

Preferably, $R_1$ is phenyl or substituted phenyl.

In any of the above embodiments of $R_1$, $R_1$ may be substituted with a moiety selected from the group consisting of halo, $C_1$ to $C_{12}$ alkyl, $C_1$ to $C_{12}$ alkoxy, $C_2$ to $C_{12}$ alkenyl and enamine to form a divalent presentation of a further compound of formula I, each of which groups may themselves be substituted or unsubstituted. Preferably $R_1$ is phenyl optionally substituted with $C_1$ to $C_6$ alkyl or $C_1$ to $C_6$ alkoxy.

In any of the embodiments of formula I, $R_1$ may be selected from the group consisting of:

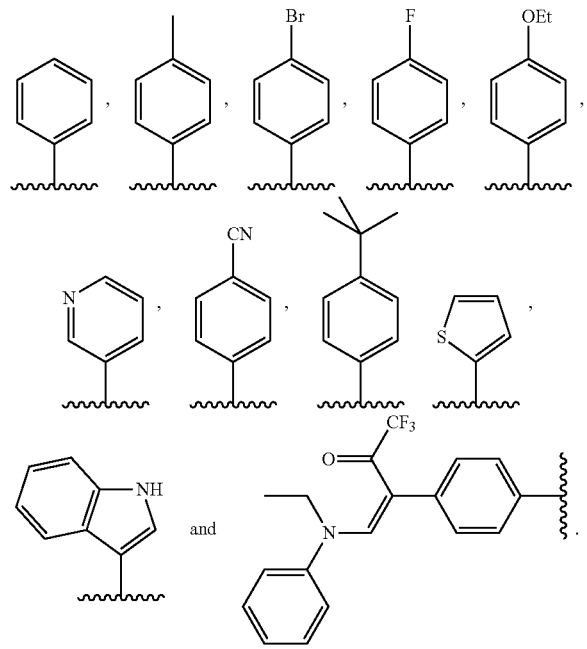

In any embodiment of the compound of formula I, $R_2$ is selected from the group consisting of hydrogen, $C_1$ to $C_6$ alkyl, $C_2$ to $C_6$ alkenyl, $C_5$ or $C_6$ aryl, $C_5$ or $C_6$ heteroaryl, $C_5$ or $C_6$ aroyl, $C_5$ or $C_6$ cycloalkenyl and $C_5$ or $C_6$ heterocyclic each of which groups may be substituted or unsubstituted.

In any embodiment of the compound of formula I, $R_2$ is selected from the group consisting of hydrogen, $C_1$ to $C_6$ alkyl, $C_2$ to $C_6$ alkenyl, $C_5$ or $C_6$ aryl, $C_5$ or $C_6$ heteroaryl and $C_5$ or $C_6$ heterocyclic each of which groups may be substituted or unsubstituted.

In preferred embodiments of the compound of formula I, $R_2$ may be selected from the group consisting of hydrogen, methyl, ethyl, propyl, isopropyl, n-butyl, sec-butyl, isobutyl, tert-butyl, pentyl and optionally substituted phenyl.

When $R_2$ is phenyl then it may be substituted with a moiety selected from the group consisting of $C_1$ to $C_6$ alkyl, $C_1$ to $C_6$ alkoxy, halo and $C_1$ to $C_6$ haloalkyl.

Preferably, $R_2$ is hydrogen or phenyl.

In any embodiment of the compound of formula I, $R_3$ and $R_4$ may be independently selected from the group consisting of $C_1$ to $C_{12}$ alkyl, $C_2$ to $C_{12}$ alkenyl, $C_2$ to $C_{12}$ alkynyl, $C_1$ to $C_{12}$ alkylamine, $C_5$ to $C_7$ aryl, biaryl, bicyclic, $C_5$ to $C_7$ heteroaryl, $C_5$ to $C_7$ aroyl, $C_4$ to $C_7$ cycloalkenyl, and $C_5$ to $C_7$ heterocyclic, all of which groups may be substituted or unsubstituted, or $R_3$ and $R_4$ may together form a cyclic structure which includes the nitrogen atom to which they are attached, said cyclic structure being selected from $C_5$ to $C_7$ saturated nitrogen heterocycles and $C_5$ to $C_7$ unsaturated nitrogen heterocycles each of which may be optionally substituted.

In any embodiment of the compound of formula I, $R_3$ and $R_4$ may be independently selected from the group consisting of $C_1$ to $C_9$ alkyl, $C_2$ to $C_9$ alkenyl, $C_1$ to $C_9$ alkylamine, phenyl, napthyl, triazine, $C_5$, $C_6$ or $C_7$ nitrogen heterocycle and a divalent presentation of a further compound of formula I, II, or III, all of which groups may be substituted or unsubstituted, or $R_3$ and $R_4$ may together form a cyclic structure which includes the nitrogen atom to which they are attached, said cyclic structure being selected from pyrrolidine, piperidine, azepane, homopiperazine, piperazine, each of which may be substituted or unsubstituted or may be fused with one or more of $C_5$ or $C_6$ aryl, $C_5$ or $C_6$ cycloalkyl, $C_5$ or $C_6$ heteroaryl or $C_5$ or $C_6$ heterocyclic rings each of which may themselves be substituted or unsubstituted.

In certain embodiments, $R_3$ and $R_4$ may be independently selected from $C_3$ to $C_{20}$ alkyl.

Preferably, $R_3$ and $R_4$ may be independently selected from $C_6$ aryl or biaryl, $C_1$ to $C_6$ alkyl, $C_1$ to $C_{12}$ alkylamine, each of which groups may be substituted or unsubstituted, and $C_5$, $C_6$ or $C_7$ nitrogen heterocycle each of which heterocycles may be optionally fused with a substituted or unsubstituted benzene ring.

Preferably, when $R_3$ and $R_4$ together form a $C_5$ nitrogen heterocycle fused with a benzene ring then the structure formed is an indoline which is optionally substituted.

In embodiments, when $R_3$ and $R_4$ together form a $C_5$ nitrogen heterocycle fused with a benzene ring then the benzene ring may be substituted with a —C(O)—O—$R_{23}$ group wherein $R_{23}$ is selected from $C_1$ to $C_{20}$ alkyl or a polymeric tag including PEG and PDMS.

In any embodiment of the compound of formula I, the structure(s) formed by $R_3$ and $R_4$ may be substituted with a moiety selected from the group consisting of halo, nitro, cyano, $C_1$ to $C_{12}$ alkyl, $C_2$ to $C_{12}$ alkenyl, $C_1$ to $C_{12}$ haloalkyl, —N-alkyl, $C_1$ to $C_{12}$ alkoxy, $C_1$ to $C_{12}$ alkylalkanoate, $C_1$ to $C_6$ haloalkyl, $C_5$ or $C_6$ aryl, $C_5$ or $C_6$ heteroaryl, $C_5$ or $C_6$ heterocyclic and enamine, to form a divalent presentation of a further compound of formula I, each of which groups may themselves be substituted or unsubstituted, when $R_3$ and $R_4$ together form a $C_5$, $C_6$ or $C_7$ nitrogen heterocycle fused with a benzene ring then the benzene ring may be optionally substituted with optionally substituted $C_1$ to $C_{12}$ alkylalkanoate, carboxymethyl ester and trifluoroalkyl.

In any embodiment of the compound of formula I, $R_3$ and $R_4$ may be independently selected from the group consisting of:

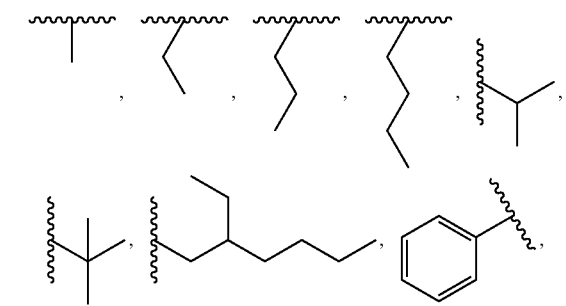

-continued
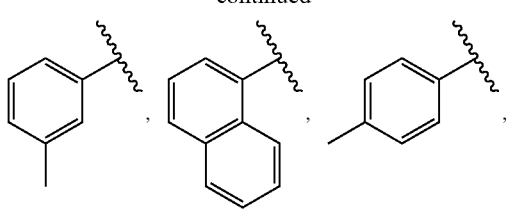
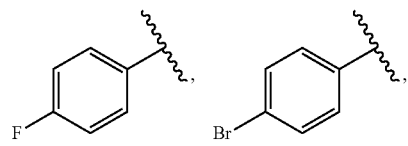
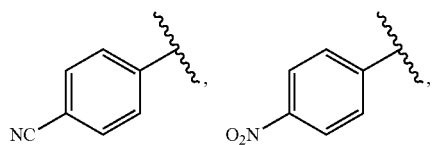
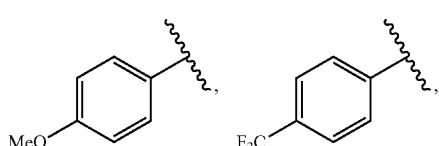
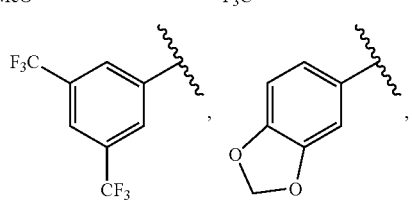
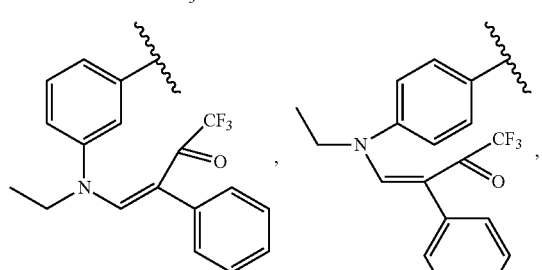
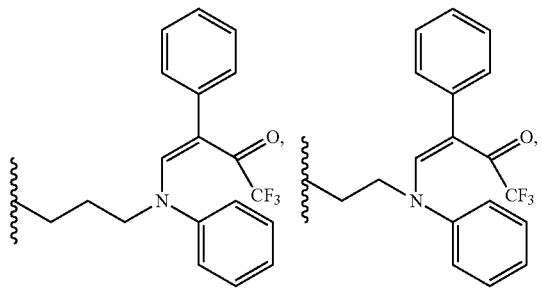
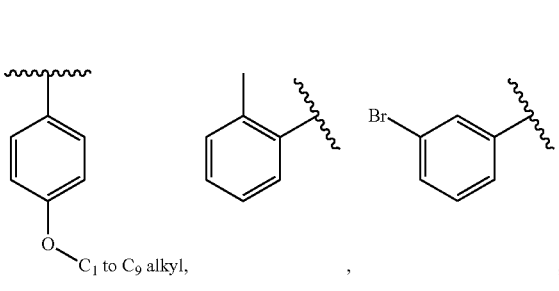
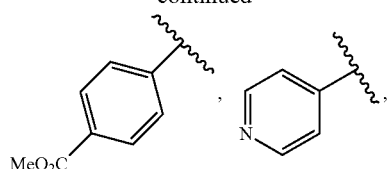
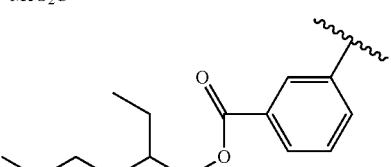
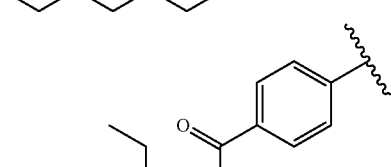
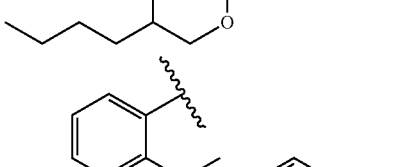
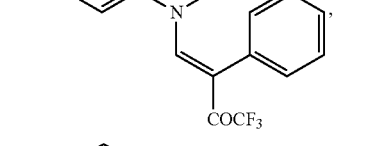
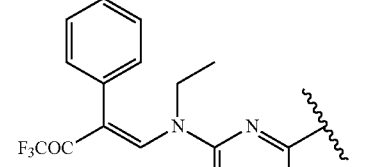
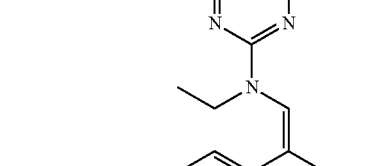
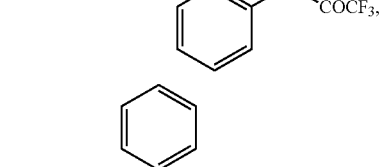
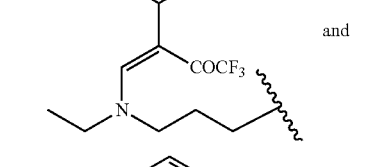, and
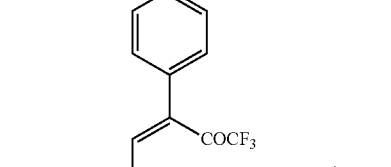

9
-continued
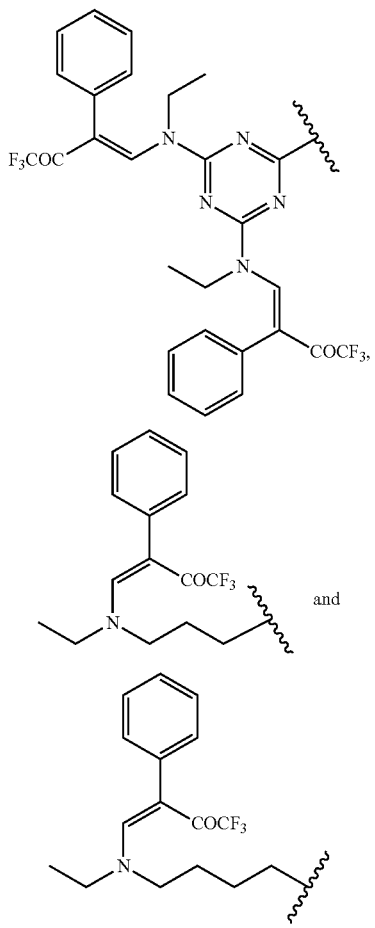
or R₃ and R₄ may together form a cyclic structure which includes the nitrogen atom to which they are attached, said cyclic structure being selected from the group consisting of:
10
-continued
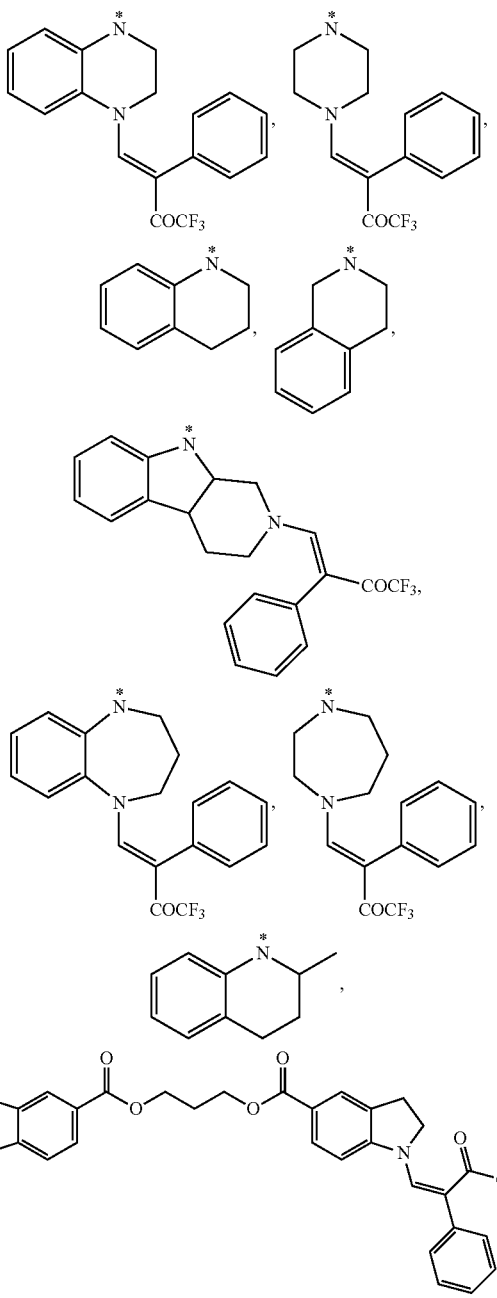
and
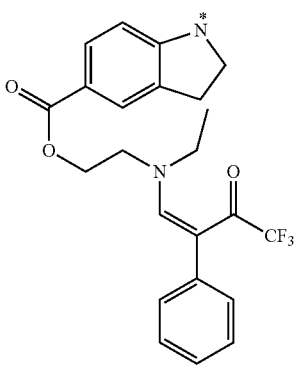

wherein, the asterisk indicates the enamine nitrogen atom to which $R_3$ and $R_4$ are directly attached; and $R_7$ and $R_8$ are selected from the group consisting of hydrogen, F, Br, Cl, $C_1$ to $C_{20}$ alkyl, $C_1$ to $C_6$ fluoroalkyl, nitro, $C_1$ to $C_6$ alkoxy, —C(O)O—$C_1$ to $C_9$ alkyl, —C(O)O—$C_1$ to $C_4$ alkyl-carbamate, carboxymethyl, carboxyethyl, a multivalent presentation of another compound of formula I, —C(O)O-PEG and —C(O)O-PDMS, each of which may be optionally substituted.

In any embodiment of the structural formulae of the first aspect presented herein, while $R_7$ and $R_8$ may often be exemplified as carboxymethyl, it should be appreciated that it is envisaged that the length of this ester alkyl chain may be extended to alter the solubility properties of the compound rather than to change the absorbvance, as such. Therefore, it is envisaged that any compound shown herein with a carboxymethyl group extending from the $R_3/R_4$ substituent could have the methyl moiety of the carboxymethyl replaced with a $C_2$ to $C_{20}$ alkyl or alkenyl chain which may be branched or unbranched. A $C_2$ to $C_{16}$ alkyl or alkenyl chain, $C_2$ to $C_{12}$ alkyl or alkenyl chain, or a $C_2$ to $C_8$ alkyl or alkenyl chain may be preferred.

To achieve optimal absorbance and to improve photostability, it is preferred that the compounds of the first aspect do not have both $R_3$ and $R_4$ as alkyl. Particularly, it is preferred that $R_3$ and $R_4$ are not both methyl.

In any embodiment of the compound of formula I, $R_5$ may be selected from the group consisting of $C_1$ to $C_{12}$ haloalkyl, $C_2$ to $C_{12}$ haloalkenyl, $C_5$ or $C_6$ aryl, $C_1$ to $C_{12}$ perhaloalkyl, $C_1$ to $C_{12}$ alkyl, $C_1$ to $C_{12}$ alkenyl, $C_1$ to $C_{12}$ alkoxy, $C_1$ to $C_{12}$ alkanoyl, phenyl, ester, amide, $C_5$ to $C_7$ heterocyclic and an enamine as a divalent presentation of a further compound of formula I, all of which groups may be substituted or unsubstituted.

In one embodiment, the $C_5$ or $C_6$ aryl is $C_5$ or $C_6$ halo-substituted aryl.

Suitably, the halo groups of the $R_5$ substituent are fluorine.

In any embodiment of the compound of formula I, $R_5$ may be selected from the group consisting of $C_1$ to $C_6$ fluoroalkyl, $C_2$ to $C_6$ fluoroalkenyl, $C_5$ or $C_6$ fluoro aryl, $C_1$ to $C_6$ perfluoroalkyl, $C_1$ to $C_6$ alkyl, $C_1$ to $C_9$ alkenyl, $C_1$ to $C_6$ alkoxy, $C_1$ to $C_9$ alkanoyl, $C_1$ to $C_6$ cyanoalkyl, phenyl, $C_1$ to $C_9$ ester, $C_1$ to $C_9$ amide, $C_5$ to $C_7$ heterocyclic and an enamine as a divalent presentation of a further compound of formula I, all of which groups may be substituted or unsubstituted.

When $R_5$ is amide then the nitrogen of the amide may form part of a nitrogen heterocycle. Preferably, the nitrogen heterocycle is 5- or 6-membered heterocycle which may be substituted or fused with an aryl ring. In certain embodiments the nitrogen heterocycle is indoline which may be substituted or unsubstituted.

In embodiments of $R_5$ wherein $R_5$ comprises an ester group then the structure may be:

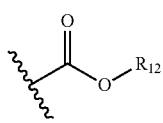

wherein $R_{12}$ is selected from the group consisting of $C_1$ to $C_{12}$ alkyl, $C_2$ to $C_6$ alkylalkanoate, $C_5$ or $C_6$ aryl, $C_5$ to $C_7$ cycloalkyl and alkylaryl.

The $C_1$ to $C_{12}$ alkyl may be a tertiary alkyl group.

In embodiments wherein $R_5$ is substituted $C_5$ or $C_6$ aryl, including phenyl, then the substituent(s) may be selected from the group consisting of $C_1$ to $C_6$ alkyl, $C_1$ to $C_6$ alkoxy, hydroxyl, nitro, cyano, halo and —S(O)$_2$—N—$R_{13}R_{14}$ wherein $R_{13}$ and $R_{14}$ of the sulphonamide group are independently selected from the group consisting of hydrogen and $C_1$ to $C_6$ alkyl.

In one embodiment, $R_5$ is fluoro-substituted phenyl or fluoroalkyl or perfluoroalkyl selected from $C_1$ to $C_9$ fluoroalkyl, $C_1$ to $C_6$ fluoroalkyl, $C_1$ to $C_4$ fluoroalkyl, $C_1$ to $C_9$ perfluoroalkyl, $C_1$ to $C_6$ perfluoroalkyl and $C_1$ to $C_4$ perfluoroalkyl.

In one embodiment, $R_5$ is polyfluoro-substituted phenyl, that is, the phenyl group is substituted with at least 2 fluorine atoms.

In any one or more embodiments of formula I, $R_5$ may be selected from the group consisting of:

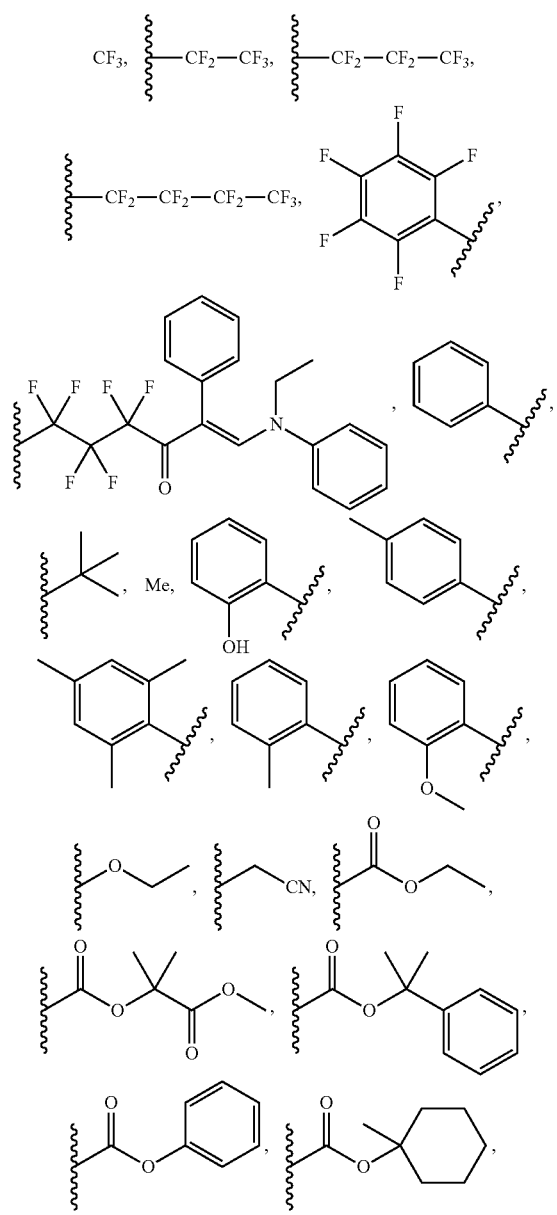

-continued

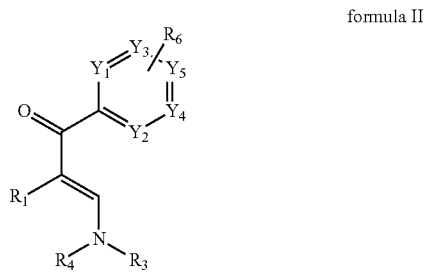

In any embodiment of the compound of the first aspect, wherein $R_5$ is phenyl then it is not unsubstituted phenyl. It has been found that substitution of the phenyl group in this position greatly improves photostability.

In one embodiment of the first aspect, there is provided a compound of formula II, or a salt or isomer thereof:

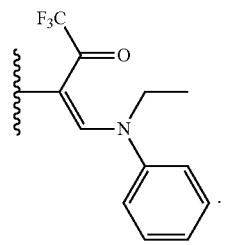 [SMILES: */C(=C/N(CC)c1ccccc1)C(=O)C(F)(F)F]

formula II wherein, $R_1$, $R_3$ and $R_4$ are independently as described for any embodiment of formula I;

$Y_1$, $Y_2$, $Y_3$, $Y_4$ and $Y_5$ are independently selected from a nitrogen or a carbon atom; and each incidence of $R_6$ is independently selected from the group consisting of hydrogen, hydroxyl, halo, nitro, cyano, $C_1$ to $C_{12}$ alkyl, $C_1$ to $C_{12}$ alcohol, $C_2$ to $C_{12}$ alkenyl, $C_1$ to $C_{12}$ alkoxy, alkoxysilane, $C_1$ to $C_6$ amide, sulphonamide, and $C_1$ to $C_{12}$ haloalkyl, each of which may be substituted or unsubstituted.

In any embodiment of the compound of formula II, each incidence of $R_6$ is independently selected from the group consisting of hydrogen, hydroxyl, Br, F, Cl, nitro, cyano, $C_1$ to $C_9$ alkyl, $C_1$ to $C_9$ alcohol, $C_2$ to $C_9$ alkenyl, $C_1$ to $C_9$ alkoxy, sulphonamide, and $C_1$ to $C_9$ haloalkyl, each of which may be substituted or unsubstituted.

In any embodiment of the compound of formula II, each incidence of $R_6$ is independently selected from the group consisting of hydrogen, hydroxyl, Br, F, $C_1$ to $C_6$ alkyl, $C_1$ to $C_6$ alcohol, $C_1$ to $C_6$ alkoxy, —S(O)$_2$N($C_1$ to $C_4$ alkyl)$_2$, and $C_1$ to $C_6$ haloalkyl, each of which may be substituted or unsubstituted.

In embodiments of formula II, $R_6$ forms one or more of a 2-, 4-, and 6-substitution pattern with any one or more of the above listed groups.

A 4-, or a 2,4,6-substitution pattern of the phenyl group may be preferred in certain embodiments of formula I or II.

In any embodiment of the compound of formula II, each incidence of $R_6$ is independently selected from the following:

H, hydroxyl, Br, OMe, OEt, F, methyl, ethyl, propyl, —S(O)$_2$NMe$_2$, and

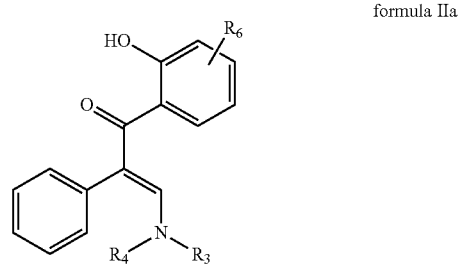

In any embodiment of the compound of formula II, either (i) $Y_1$ and $Y_2$; or (ii) $Y_3$ and $Y_4$; or (iii) $Y_5$ are a nitrogen atom. Those which are not nitrogen atoms will be carbon atoms.

In certain embodiments, all of $Y_1$, $Y_2$, $Y_3$, $Y_4$ and $Y_5$ are carbon atoms.

In preferred embodiments of the compound of formula II, $R_1$ is phenyl or substituted phenyl.

In one particular embodiment of the compound of formula II, there is provided a compound of formula IIa, or a salt or isomer thereof:

formula IIa wherein, $R_3$, $R_4$ and $R_6$ are independently as described for any embodiment of formula I and/or formula II.

In embodiments, each incidence of $R_6$ is independently selected from the group consisting of hydrogen, hydroxyl, Br, F, $C_1$ to $C_4$ alkyl, $C_1$ to $C_4$ alcohol, $C_1$ to $C_4$ alkoxy, and $C_1$ to $C_4$ haloalkyl, each of which may be substituted or unsubstituted.

Suitably, $R_6$ may be hydrogen.

In one embodiment of the first aspect, there is provided a compound of formula III, or a salt or isomer thereof:

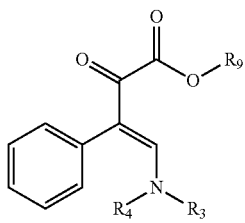

formula III wherein, $R_3$ and $R_4$ are independently as described for any embodiment of formula I, II, and IIa; and $R_9$ is selected from aryl, $C_1$ to $C_{12}$ alkyl, $C_1$ to $C_{12}$ alkyl aryl, $C_5$ to $C_7$ cycloalkyl, $C_5$ or $C_6$ heterocycle and $C_2$ to $C_{12}$ alkylalkanoate, each of which may be substituted or unsubstituted.

The $C_1$ to $C_{12}$ alkyl may be a tertiary alkyl group.

In embodiments of the compound of formula III, $R_9$ is selected from $C_5$ or $C_6$ aryl, $C_1$ to $C_9$ alkyl, $C_1$ to $C_6$ alkyl aryl, $C_5$ or $C_6$ cycloalkyl, $C_5$ or $C_6$ nitrogen heterocycle and $C_2$ to $C_9$ alkylalkanoate, each of which may be substituted or unsubstituted.

In embodiments of the compound of formula III, $R_9$ is selected from phenyl, $C_1$ to $C_9$ alkyl, $C_1$ to $C_4$ alkyl aryl, $C_6$ cycloalkyl, indoline and $C_2$ to $C_6$ alkylalkanoate, each of which may be substituted or unsubstituted.

In preferred embodiments of the compound of formula III, $R_9$ is selected from optionally substituted phenyl and a tertiary alkyl.

The tertiary alkyl may be tert-butyl.

In one embodiment of the first aspect, there is provided a compound of formula IV, or a salt or isomer thereof:

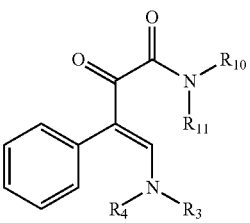

formula IV wherein, $R_3$ and $R_4$ are independently as described for any embodiment of formula I, II, IIa and III; and $R_{10}$ and $R_{11}$ are independently selected from the group consisting of hydrogen, $C_1$ to $C_{20}$ alkyl, $C_2$ to $C_{20}$ alkenyl, $C_2$ to $C_{20}$ alkynyl, $C_1$ to $C_{20}$ alkylamine, aryl, heteroaryl, aroyl, $C_5$ to $C_7$ cycloalkyl, $C_3$ to $C_8$ cycloalkenyl, $C_2$ to $C_{12}$ alkanoyloxy, haloalkyl, and heterocyclic, all of which groups may be substituted or unsubstituted, or $R_{10}$ and $R_{11}$ may together form a cyclic structure which includes the nitrogen atom to which they are attached, said cyclic structure being optionally substituted.

In any embodiment of the compound of formula IV, $R_{10}$ and $R_{11}$ may be independently selected from the group consisting of hydrogen, $C_1$ to $C_{12}$ alkyl, $C_2$ to $C_{12}$ alkenyl, $C_2$ to $C_{12}$ alkynyl, $C_1$ to $C_{12}$ alkylamine, $C_5$ to $C_7$ aryl, biaryl, bicyclic, $C_5$ to $C_7$ heteroaryl, $C_5$ to $C_7$ aroyl, $C_4$ to $C_7$ cycloalkenyl, and $C_5$ to $C_7$ heterocyclic, all of which groups may be substituted or unsubstituted, or $R_{10}$ and $R_{11}$ may together form a cyclic structure which includes the nitrogen atom to which they are attached, said cyclic structure being selected from $C_5$ to $C_7$ saturated nitrogen heterocycles and $C_5$ to $C_7$ unsaturated nitrogen heterocycles each of which may be optionally substituted.

In any embodiment of the compound of formula IV, $R_{10}$ and $R_{11}$ may be independently selected from the group consisting of hydrogen, $C_1$ to $C_9$ alkyl, $C_2$ to $C_9$ alkenyl, $C_1$ to $C_9$ alkylamine, phenyl, napthyl, triazine, $C_5$, $C_6$ or $C_7$ nitrogen heterocycle and a divalent presentation of a further compound of formula I, II, or Ill, all of which groups may be substituted or unsubstituted, or $R_{10}$ and $R_{11}$ may together form a cyclic structure which includes the nitrogen atom to which they are attached, said cyclic structure being selected from pyrrolidine, piperidine, azepane, homopiperazine, piperazine, each of which may be substituted or unsubstituted or may be fused with one or more of $C_5$ or $C_6$ aryl, $C_5$ or $C_6$ cycloalkyl, $C_5$ or $C_6$ heteroaryl or $C_5$ or $C_6$ heterocyclic rings each of which may themselves be substituted or unsubstituted.

Preferably, $R_{10}$ and $R_{11}$ may be independently selected from hydrogen, $C_6$ aryl or biaryl, $C_1$ to $C_6$ alkyl, $C_1$ to $C_{12}$ alkylamine, each of which groups may be substituted or unsubstituted, and $C_5$, $C_6$ or $C_7$ nitrogen heterocycle each of which heterocycles may be optionally fused with a substituted or unsubstituted benzene ring.

Preferably, when $R_{10}$ and $R_{11}$ together form a $C_5$ nitrogen heterocycle fused with a benzene ring then the structure formed is an indoline which is optionally substituted.

In one embodiment of the first aspect, there is provided a compound of formula V, or a salt or isomer thereof:

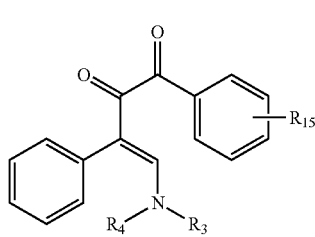

formula V wherein, $R_3$ and $R_4$ are independently as described for any embodiment of formula I, II, IIa, III and IV; and each incidence of $R_{15}$ is independently selected from those groups described for $R_6$.

In embodiments of the compound of formula V, each incidence of $R_{15}$ is independently selected from the group consisting of hydrogen, hydroxyl, halo, nitro, cyano, $C_1$ to $C_{12}$ alkyl, $C_1$ to $C_{12}$ alcohol, $C_2$ to $C_{12}$ alkenyl, $C_1$ to $C_{12}$ alkoxy, sulphonamide, and $C_1$ to $C_{12}$ haloalkyl, each of which may be substituted or unsubstituted.

In any embodiment of the compound of formula V, each incidence of $R_{15}$ is independently selected from the group consisting of hydrogen, hydroxyl, Br, F, Cl, nitro, cyano, $C_1$ to $C_9$ alkyl, $C_1$ to $C_9$ alcohol, $C_2$ to $C_9$ alkenyl, $C_1$ to $C_9$ alkoxy, sulphonamide, and $C_1$ to $C_9$ haloalkyl, each of which may be substituted or unsubstituted.

In any embodiment of the compound of formula V, each incidence of $R_{15}$ is independently selected from the group consisting of hydrogen, hydroxyl, Br, F, $C_1$ to $C_6$ alkyl, $C_1$ to $C_6$ alcohol, $C_1$ to $C_6$ alkoxy, —S(O)$_2$N($C_1$ to $C_4$ alkyl)$_2$, and $C_1$ to $C_6$ haloalkyl, each of which may be substituted or unsubstituted.

In preferred embodiments, each incidence of $R_{15}$ may be selected from hydrogen and optionally substituted $C_1$ to $C_9$ alkyl.

In one embodiment of the first aspect, there is provided a compound of formula VI, or a salt or isomer thereof:

formula VI

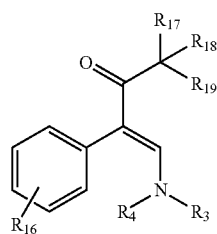

wherein, $R_3$ and $R_4$ are independently selected from those groups as described for any embodiment of formula I, II, IIa, III, IV and V;

$R_{17}$, $R_{18}$ and $R_{19}$ are independently selected from methyl, ethyl and propyl; and each incidence of $R_{16}$ is independently selected from those groups described for $R_6$.

Preferably, $R_{17}$, $R_{18}$ and $R_{19}$ are methyl.

In embodiments of the compound of formula VI, each incidence of $R_{16}$ is independently selected from the group consisting of hydrogen, hydroxyl, halo, nitro, cyano, $C_1$ to $C_{12}$ alkyl, $C_1$ to $C_{12}$ alcohol, $C_2$ to $C_{12}$ alkenyl, $C_1$ to $C_{12}$ alkoxy, sulphonamide, and $C_1$ to $C_{12}$ haloalkyl, each of which may be substituted or unsubstituted.

In any embodiment of the compound of formula VI, each incidence of $R_{16}$ is independently selected from the group consisting of hydrogen, hydroxyl, Br, F, Cl, nitro, cyano, $C_1$ to $C_9$ alkyl, $C_1$ to $C_9$ alcohol, $C_2$ to $C_9$ alkenyl, $C_1$ to $C_9$ alkoxy, sulphonamide, and $C_1$ to $C_9$ haloalkyl, each of which may be substituted or unsubstituted.

In any embodiment of the compound of formula VI, each incidence of $R_{16}$ is independently selected from the group consisting of hydrogen, hydroxyl, Br, F, $C_1$ to $C_6$ alkyl, $C_1$ to $C_6$ alcohol, $C_1$ to $C_6$ alkoxy, —S(O)$_2$N($C_1$ to $C_4$ alkyl)$_2$, and $C_1$ to $C_6$ haloalkyl, each of which may be substituted or unsubstituted.

In embodiments, each incidence of $R_{16}$ may be selected from hydrogen and optionally substituted $C_1$ to $C_9$ alkyl.

In certain embodiments of the compound of formula VI, $R_{16}$ is hydrogen and $R_3$ and $R_4$ together form an optionally substituted indoline ring system.

The benzene ring of the indoline is suitably substituted with a group selected from $C_1$ to $C_6$ alkyl, $C_1$ to $C_6$ alcohol, $C_1$ to $C_6$ alkoxy and carboalkoxy, optionally carbomethoxy and carboethoxy.

In particular embodiments of a compound of any one of formula I to VI, $R_3$ and $R_4$ may independently be selected from the group consisting of $C_1$ to $C_6$ alkyl and $C_5$ or $C_6$ aryl, or may together form an indoline group, each of which groups may be substituted or unsubstituted.

In certain embodiments of a compound of any one of formula I to VI, $R_3$ and $R_4$ may independently be selected from optionally substituted phenyl and indoline.

When the indoline group is substituted it may be substituted at one or more of the 4-, 5-, and 6-positions.

Preferred indoline substitutions are with carboalkoxy with an alkyl chain of less than 6 carbons, optionally carbomethoxy or carboethoxy. One preferred example is 5-carbomethoxyindoline.

In one embodiment of the first aspect, there is provided a compound of formula VII, or a salt or isomer thereof:

formula VII

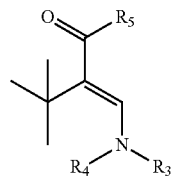

wherein, $R_3$, $R_4$ and $R_5$, as appropriate, are independently selected from those groups as described for any embodiment of formula I, II, IIa, III, IV, V and VI.

In one embodiment, $R_5$ is selected from $C_1$ to $C_6$ alkyl and optionally substituted phenyl.

In one embodiment, the $C_1$ to $C_6$ alkyl group is a tert-butyl group.

When the phenyl group is substituted then the substituent may be selected from any one or more of those groups described for $R_{15}$ and/or $R_{16}$.

The compounds of the first aspect may be effective absorbers in the UV-A, UV-B and visible regions of the spectrum. The benefits of protection from UV light for humans and various materials are well known. The dangers of exposure to visible light have received less attention but are of potentially equally serious consequence. Visible light sensitivity, for example, is an important phenomenon in diseases such as porphyria, solar urticaria, and other idiopathic photodermatoses, such as polymorphous light eruption. Patients who undergo photodynamic therapy treatments also become sensitive to visible light for a few days because of the accompanying topical medications. Protection against visible light might also be important for darker skinned patients who have pigmentary disorders. Finally, visible light is thought to be a causative agent in age-related macular degeneration of the eye and so lenses and glasses offering protection in this range would be advantageous. As is discussed further in the examples section, compounds of the first aspect have been shown to be stable enough to survive the relatively harsh and demanding lens casting conditions and to be photostable when within the lens to thereby offer a practical solution to the difficulty of achieving effective protection in such lenses.

Organic sunscreen agents typically offer no protection against visible light, as their absorption spectrum is limited to UVB and UVA wavebands. Inorganic sunscreen agents, such as iron oxide, titanium dioxide, and zinc oxide can offer some visible light protection. However, the spectral protection of these agents varies according to their particle size. It is an advantage of the present invention that the variation in compound substitutions provides for a range of absorptions and so a number of compounds presented herein represent effective absorbers in the visible light region. It is expected that the perceived importance of such absorbing compounds in an effective sunscreen, or otherwise light protective formulation, will only increase with realisation by the general public of the risks. Compounds of the present invention, or combinations thereof, can provide an effective solution.

Therefore, in one embodiment of the first aspect, there is provided a compound of formula VIII, or a salt or isomer thereof:

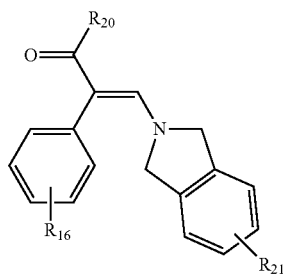

formula VIII wherein, each incidence of $R_{16}$ is independently selected from those groups described for $R_6$;

$R_{20}$ is selected from $C_1$ to $C_6$ haloalkyl, optionally substituted phenyl, or $R_{20}$ comprises an ester group having the following structure:

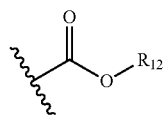

wherein $R_{12}$ is selected from the group consisting of $C_1$ to $C_{12}$ alkyl, $C_2$ to $C_6$ alkylalkanoate and $C_5$ or $C_6$ aryl; and $R_{21}$ is selected from hydrogen, —C(O)O—$C_1$ to $C_{20}$ alkyl inclusive of carboxymethyl, and a divalent presentation of a compound of the first aspect.

The compounds of formula VIII have been found to be particularly effective as absorbing compounds in the UV-A and visible regions of the spectrum and so may find applications, as discussed above, as visible light energy absorbing compounds.

In embodiments, the $R_{12}C_1$ to $C_{12}$ alkyl may be a tertiary alkyl group.

Preferably, $R_{12}$ is a $C_1$ to $C_6$ alkyl group with optional $C_1$ to $C_4$ alkyl branches.

In embodiments, $R_{16}$ is hydrogen.

Suitably, $R_{20}$ is selected from $C_1$ to $C_3$ fluoroalkyl, phenyl or $R_{20}$ comprises an ester group having the following structure:

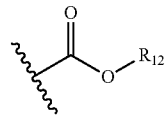

wherein $R_{12}$ is $C_1$ to $C_6$ alkyl.

In certain embodiments of the compounds of any one of formula I to VIII, as appropriate, $R_1$, $R_3$, $R_4$, and $R_5$ may form a 'divalent presentation' of another compound of any one of formula I to VIII. By this it is meant that the divalent presentation is made up of the first compound of any one of formula I to VIII and a second compound of any one of formula I to VIII which extends from one of the R groups mentioned. The second compound of any one of formula I to VIII may be connected to the first directly as the appropriate R group or may be joined via a linking group. This linking group may take the form of an aryl, alkylaryl, alkoxy or alkoxyaryl group or a short (i.e. 1 to 6 carbons) carbon chain which may itself be substituted. In certain embodiments a propyl chain is the preferred linking group. In one embodiment, the carbon linking chain comprises at least one carbon-fluorine bond. In certain embodiments at least two carbons in the chain have at least one carbon-fluorine bond. The second compound may be a repeat of the first compound to thereby form a symmetrical divalent presentation.

In one embodiment, the compound of any one of formula I to VIII, as appropriate, is selected from the group consisting of:

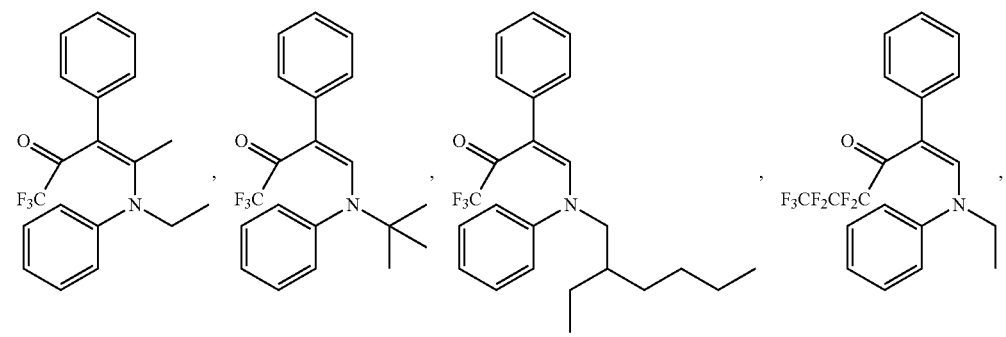

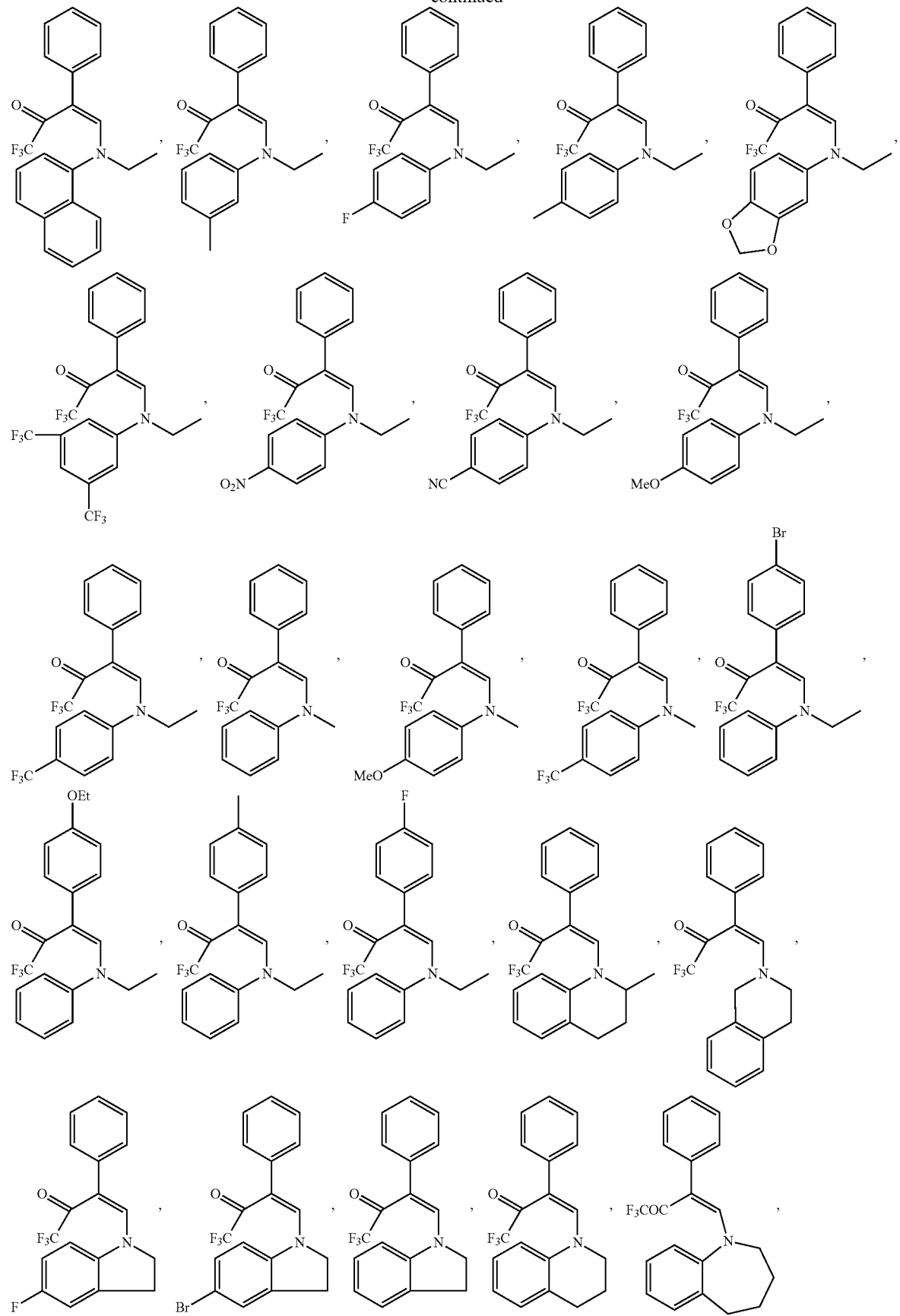

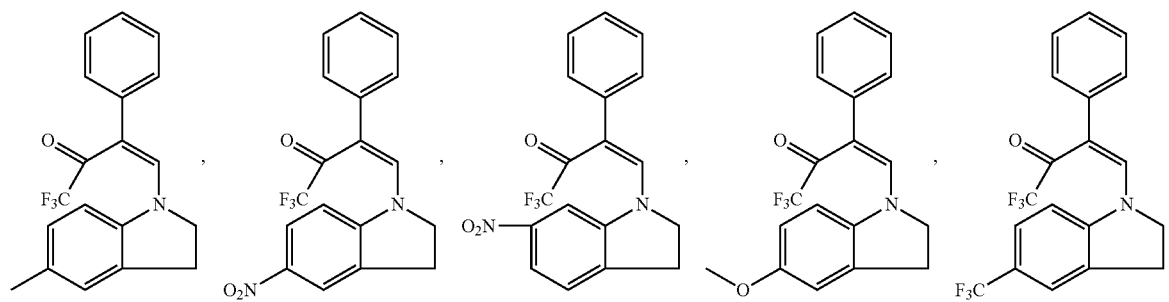
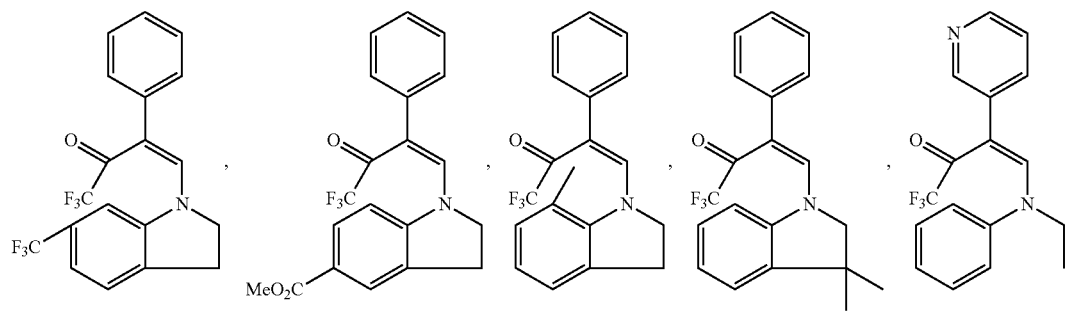
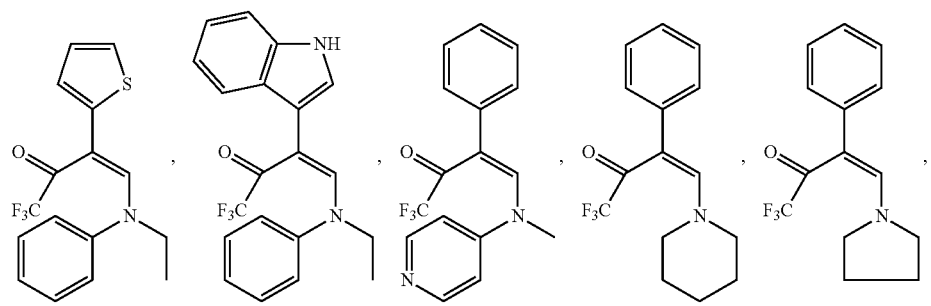
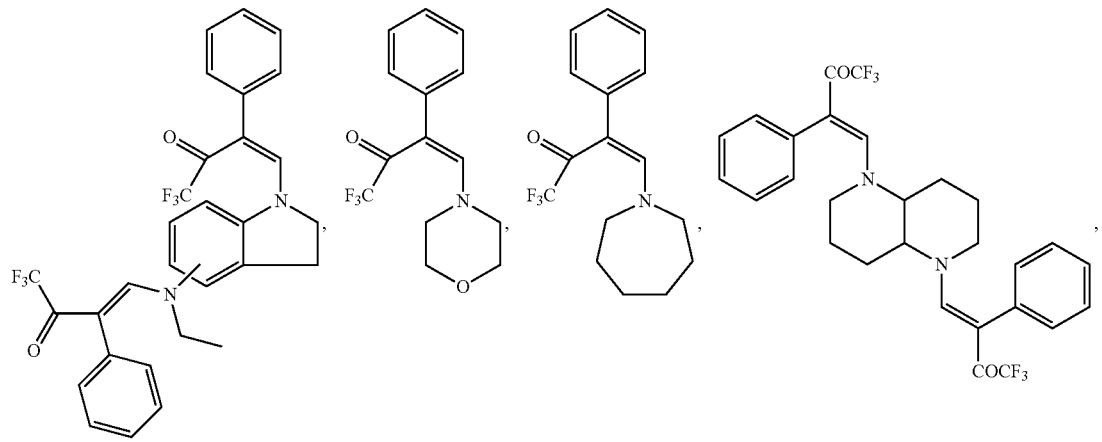

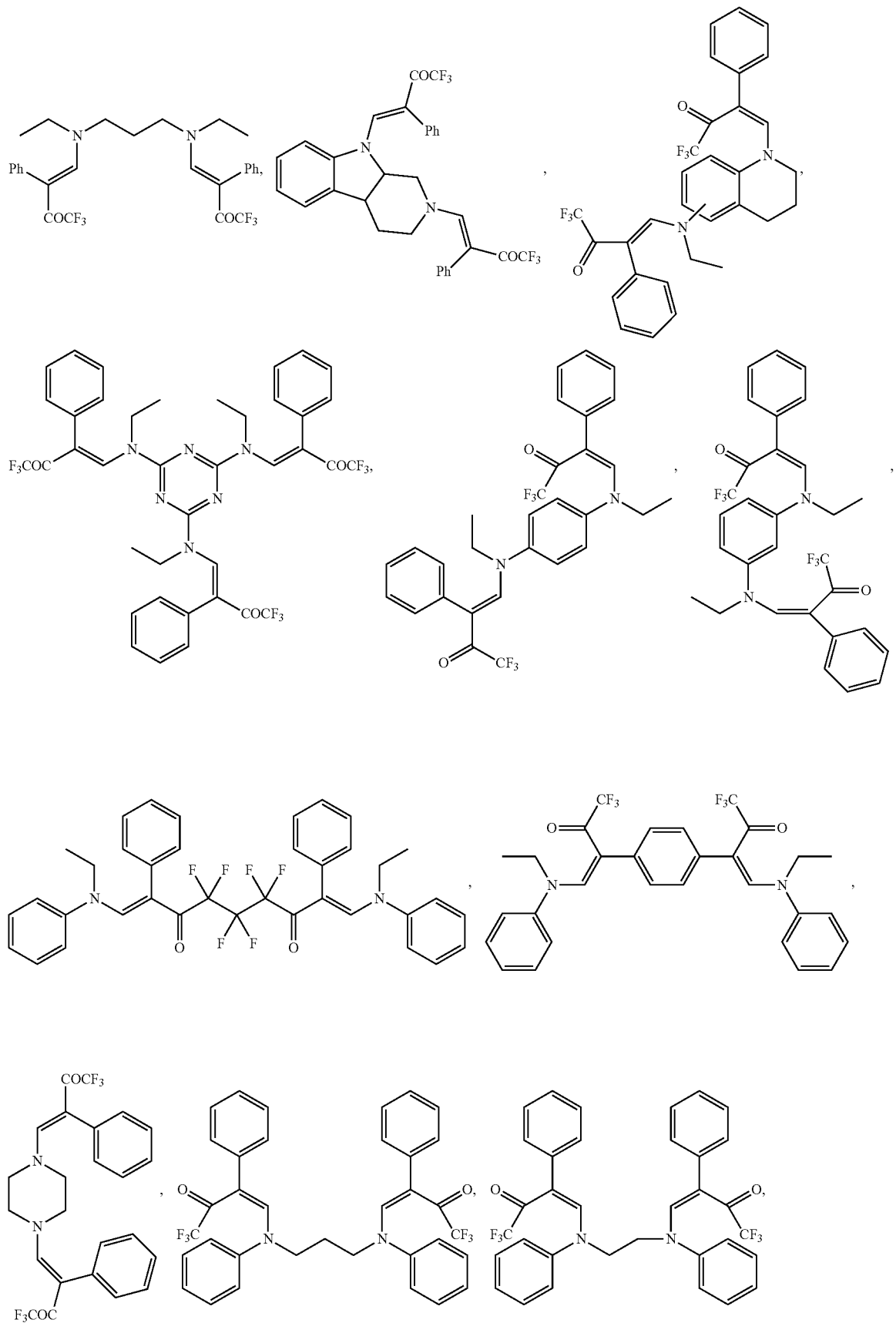

-continued
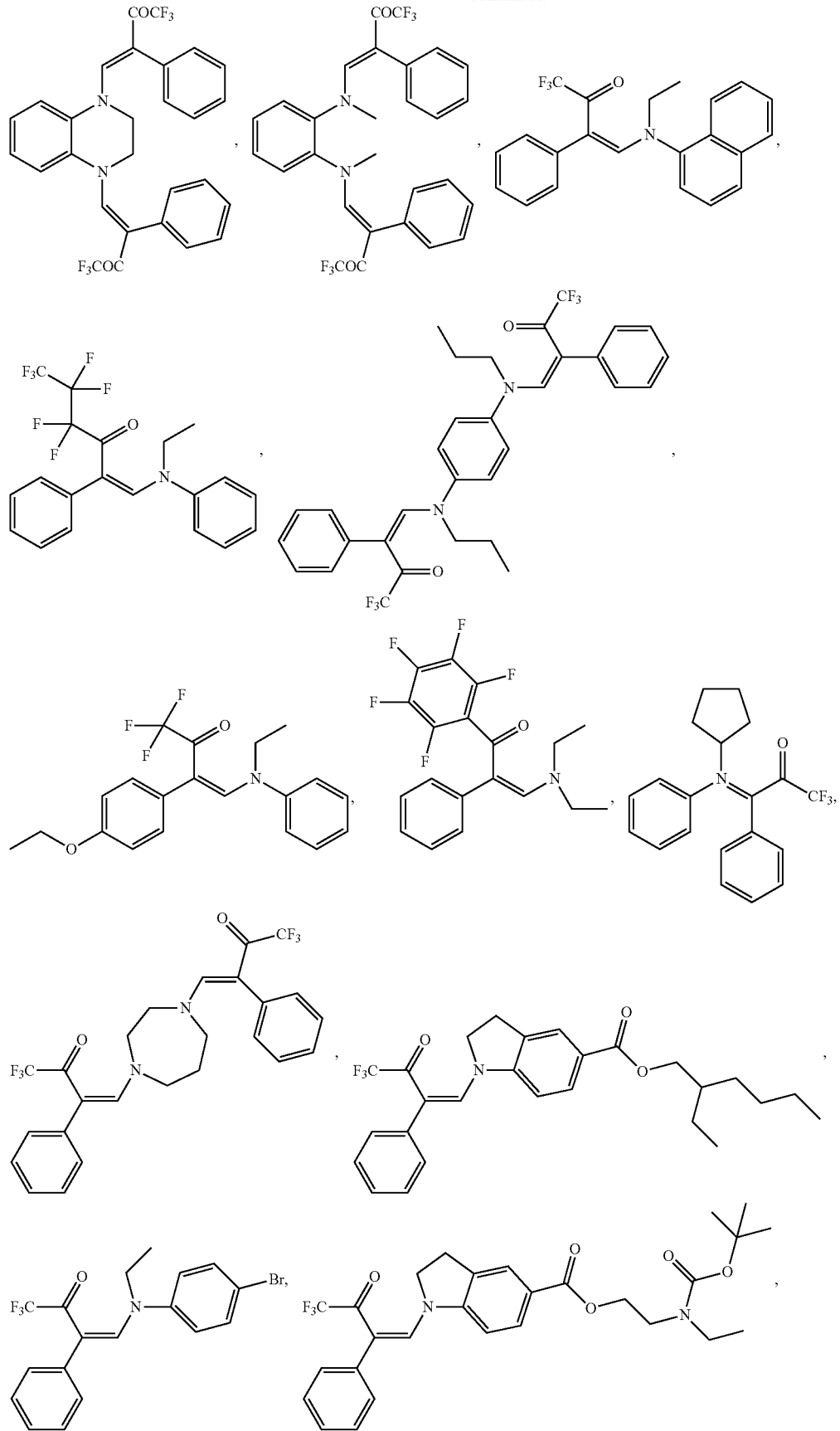

-continued
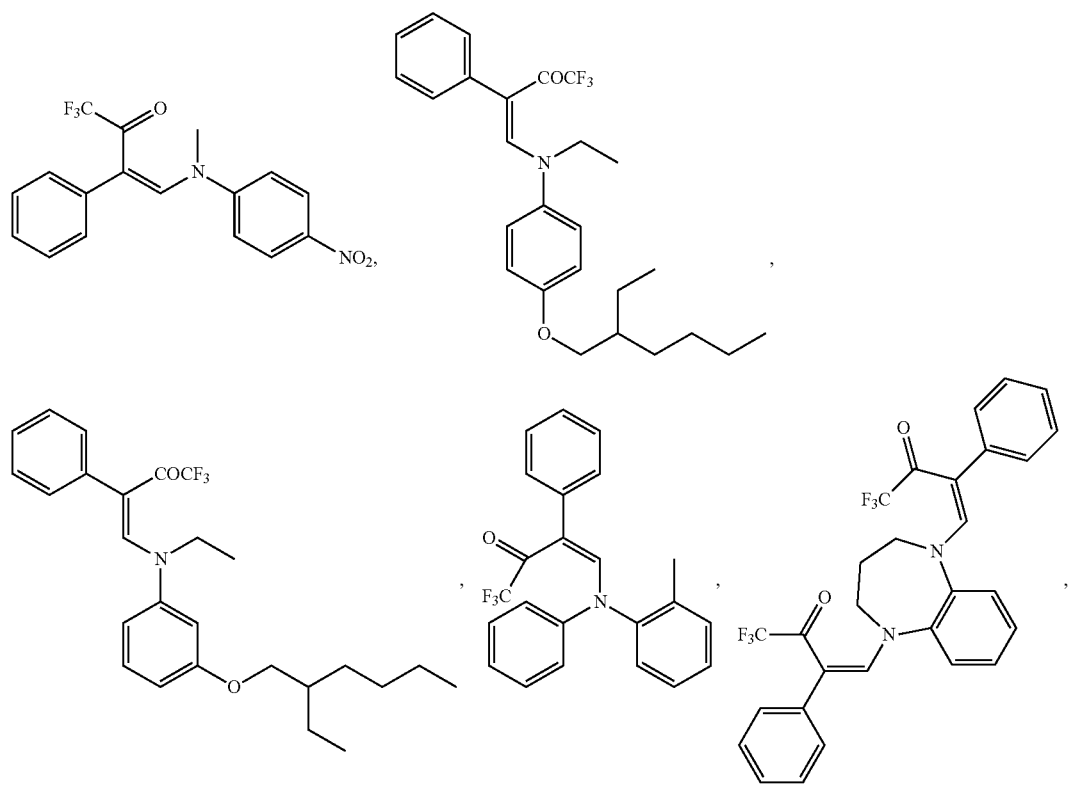
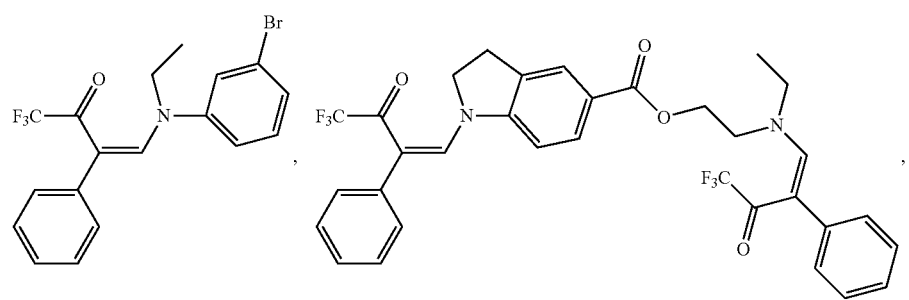
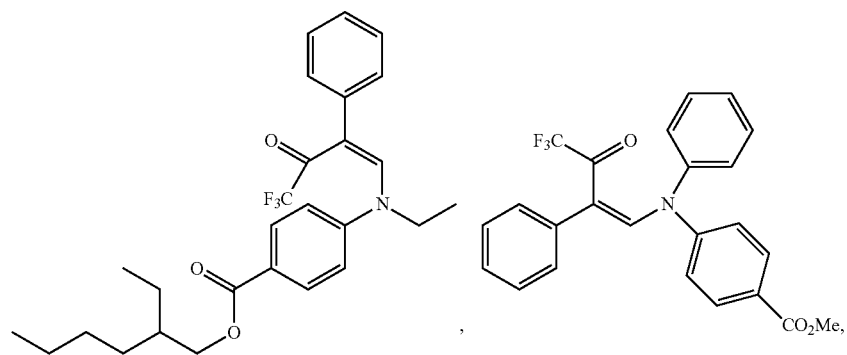

-continued
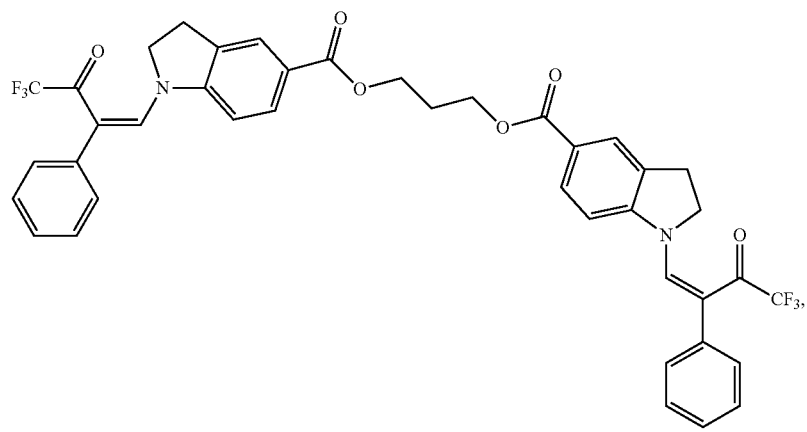
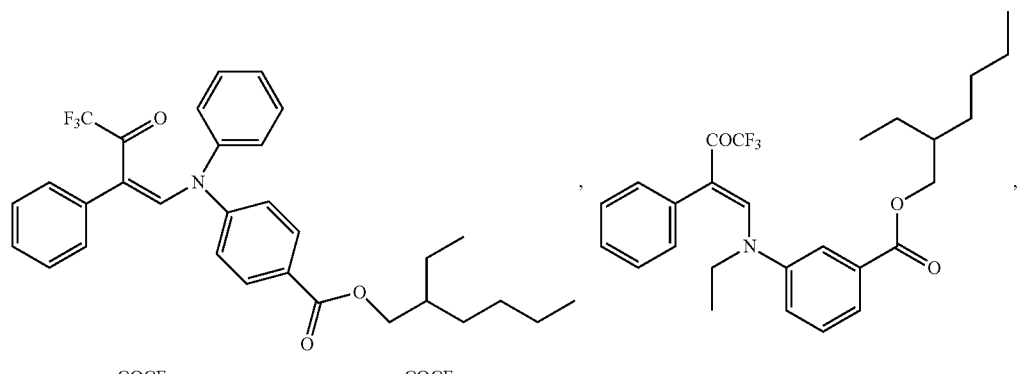
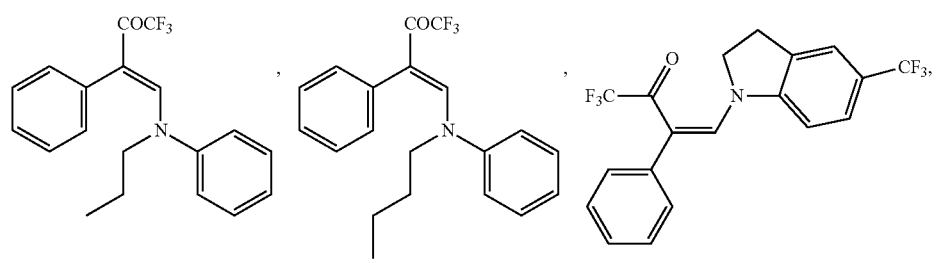
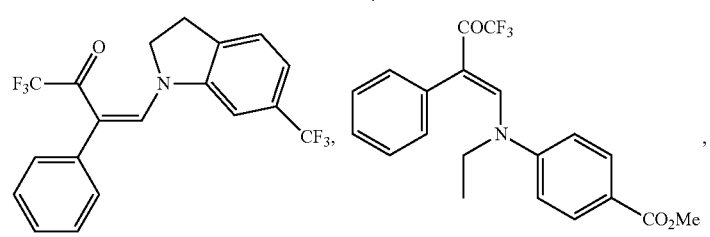
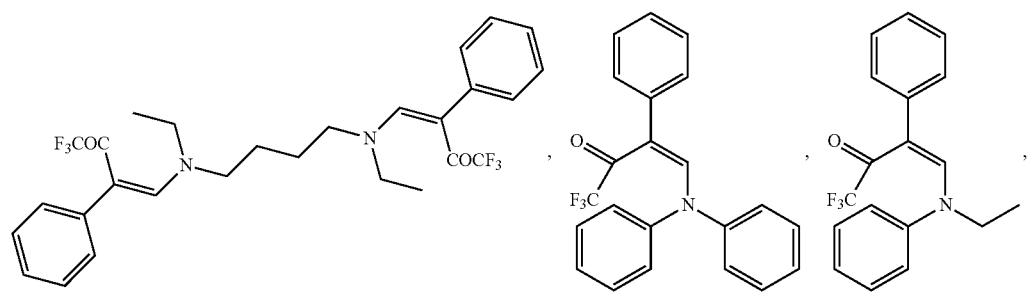

-continued
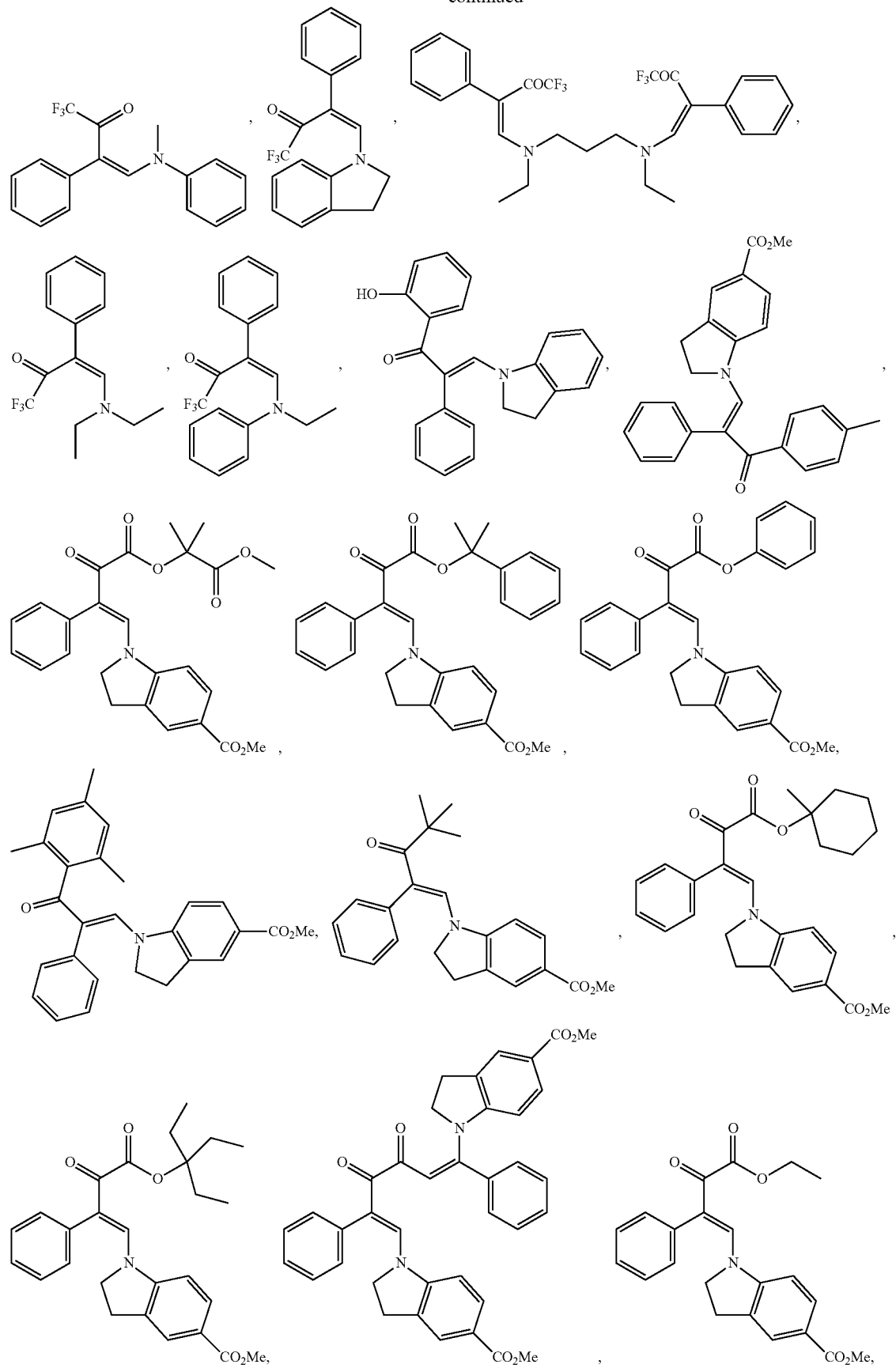

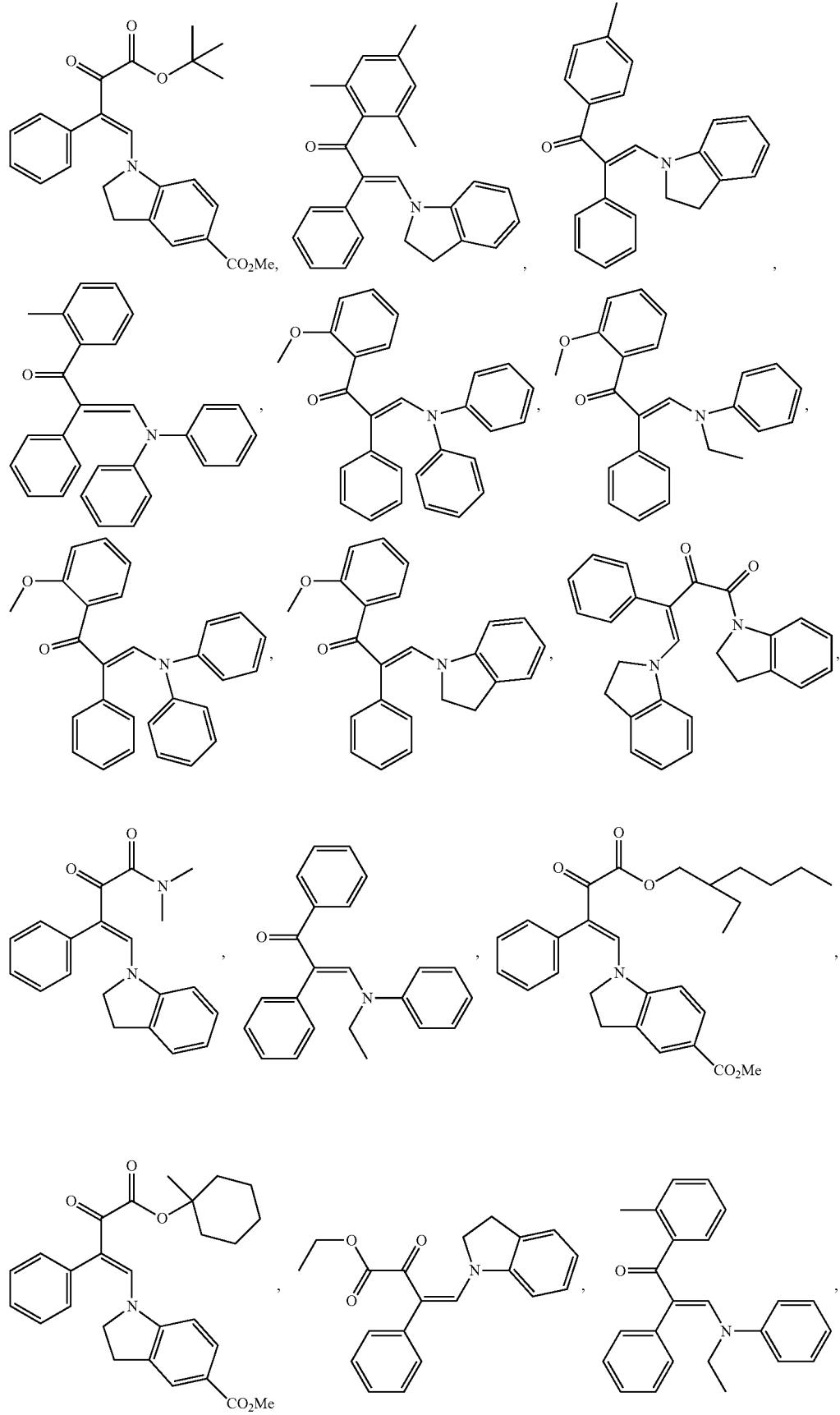

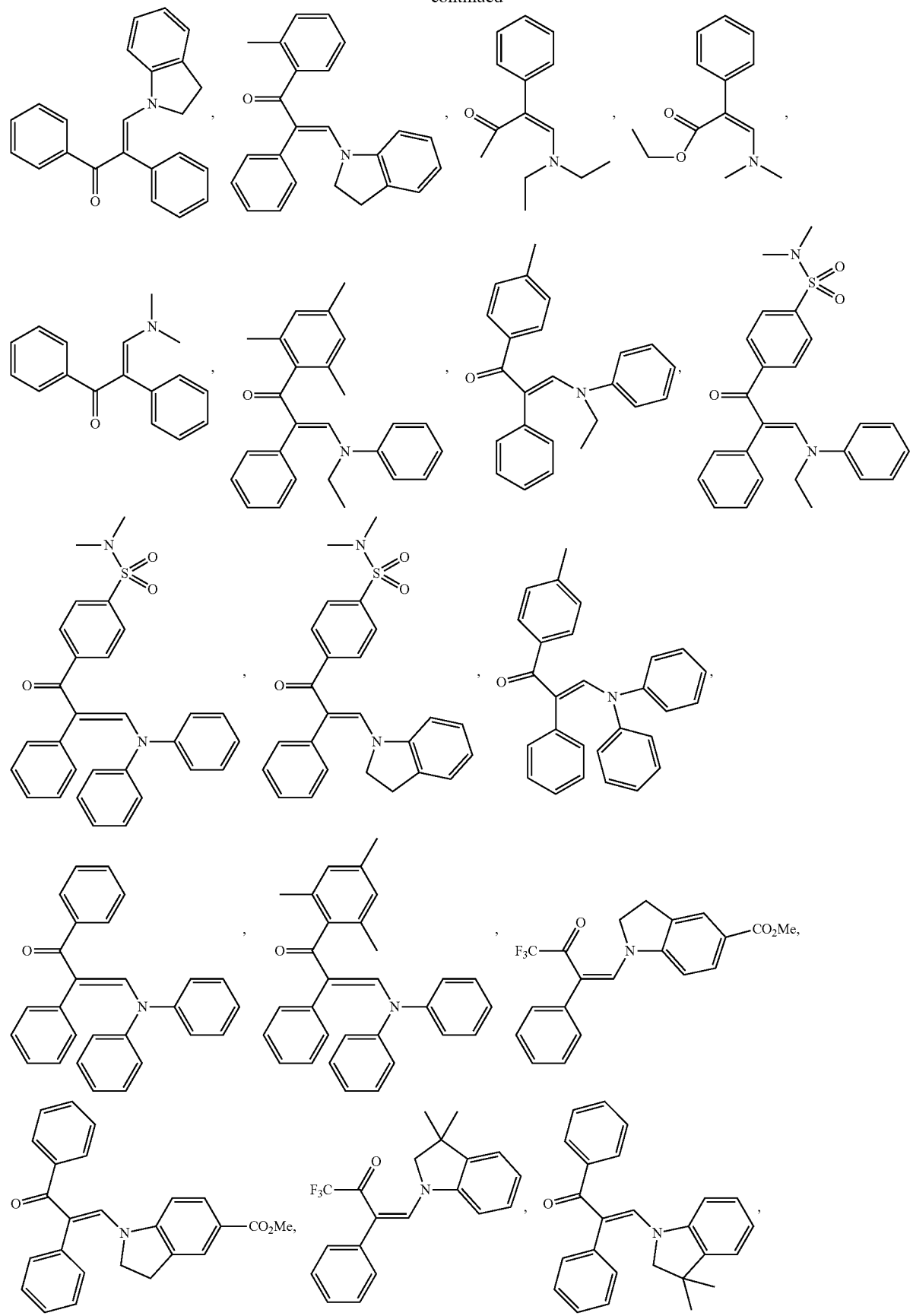

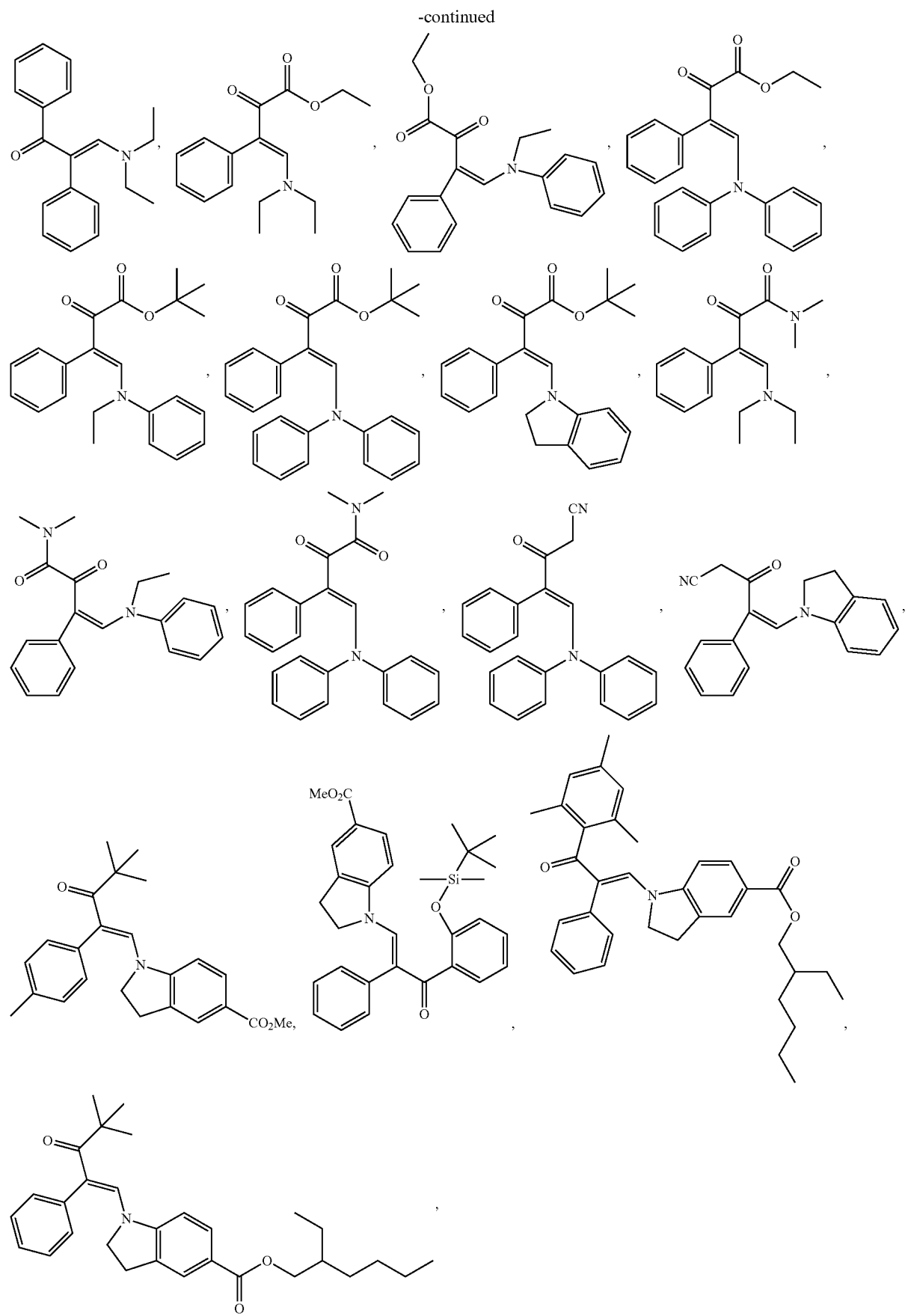

-continued
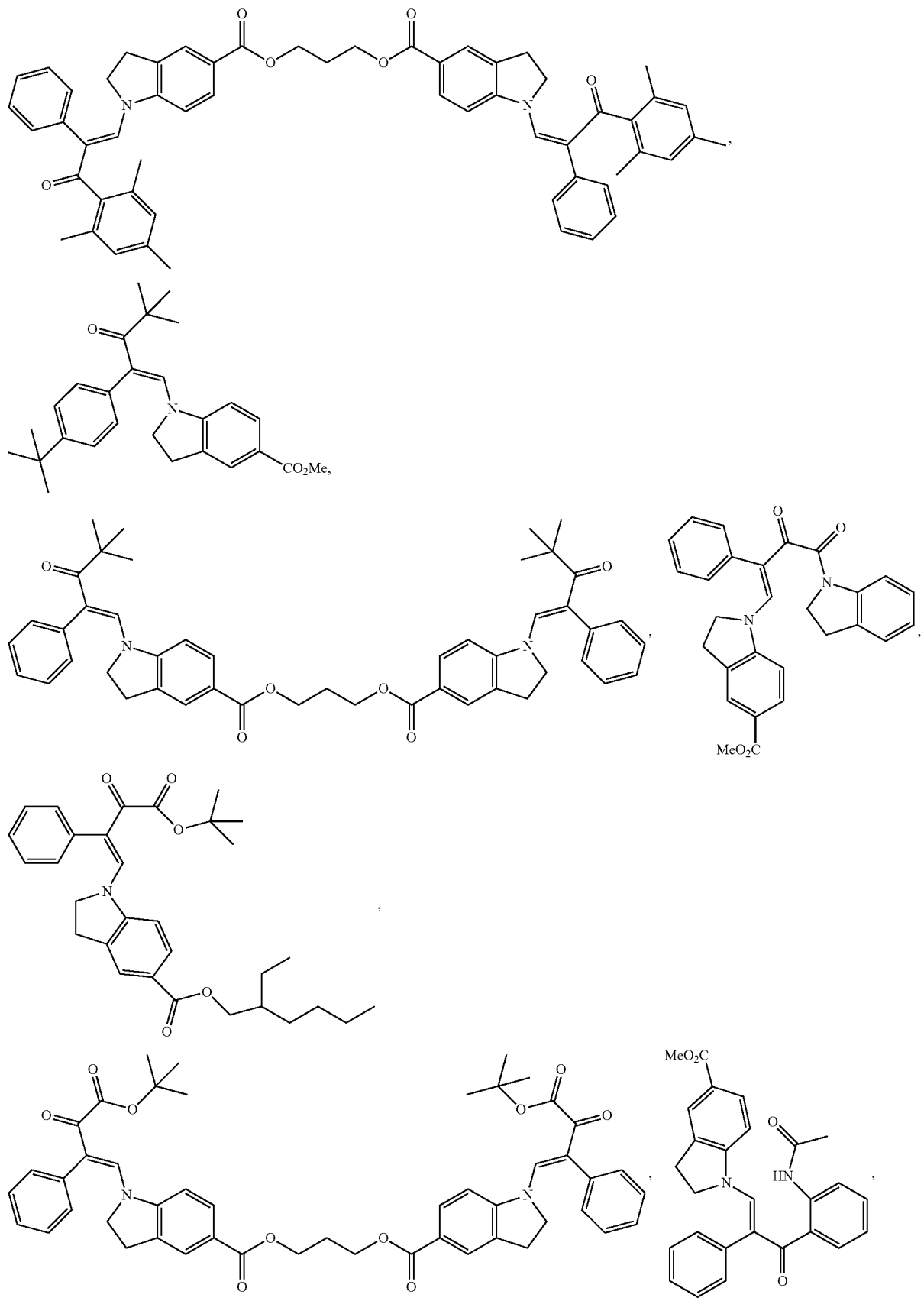

-continued
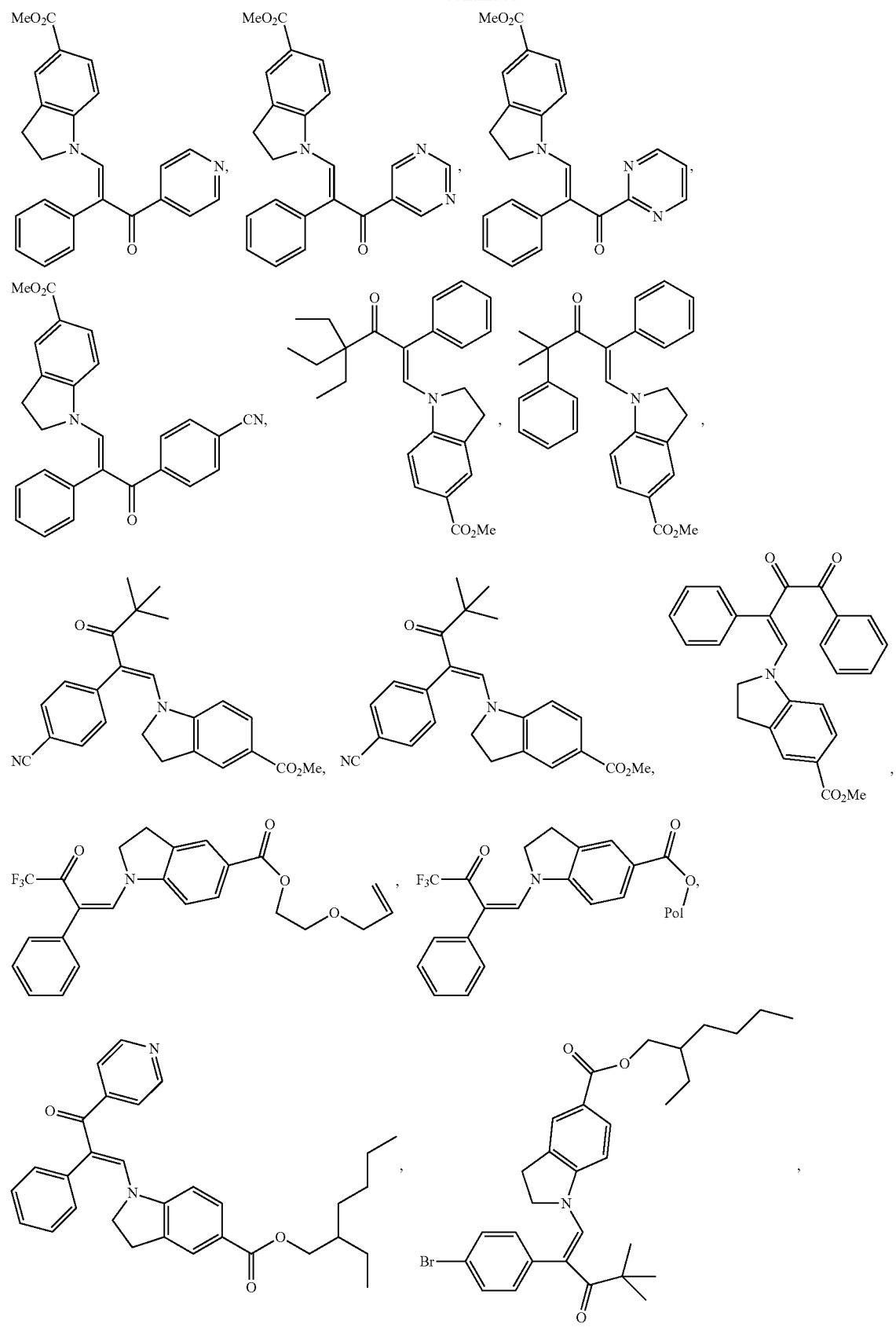

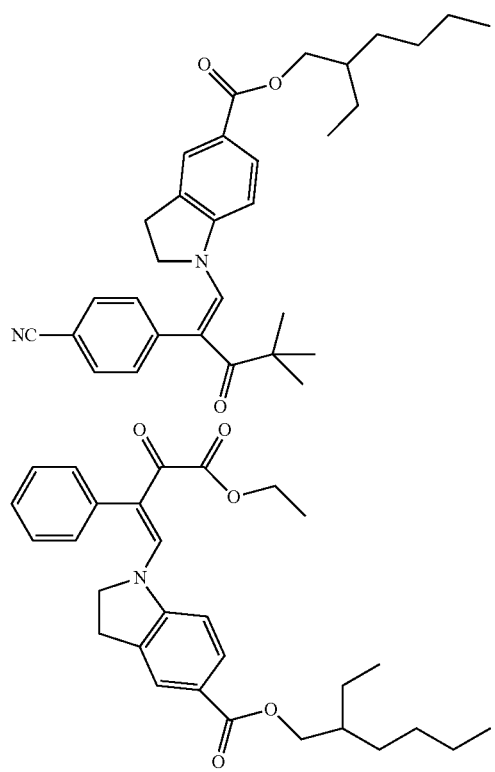

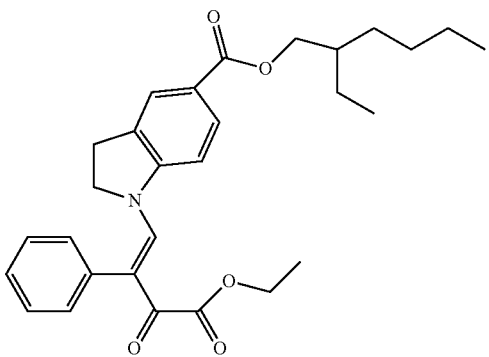

and salts and/or isomers thereof, wherein 'Pol' may be PEG, PDMS or $C_6$ to $C_{20}$ alkyl and wherein a bond extending from within a ring structure indicates that bond may be connected directly to any of the ring atoms of that structure, as appropriate.

The compounds of any one of formula I to VIII may demonstrate one or more advantages over the prior art including but not limited to one or more of improved or otherwise desirable; absorbance, physical stability, photostability, $\lambda_{max}$, $\lambda_{crit}$, molar extinction coefficient, mass extinction coefficient, steepness and/or breakthrough (as defined herein), solubility, increased molecular weight, c log P, ease of synthesis, low cost of synthesis relative to cyclic analogues, and effective absorbance in an alternate region of the electromagnetic spectrum i.e. they may provide access to a region of the spectrum not provided for by prior art compounds.

Referring now to terminology used generically herein, the term "alkyl" means a straight-chain or branched alkyl substituent containing from, for example, 1 to about 12 carbon atoms, preferably 1 to about 9 carbon atoms, more preferably 1 to about 6 carbon atoms, even more preferably from 1 to about 4 carbon atoms, still yet more preferably from 1 to 2 carbon atoms. Examples of such substituents considered to be included within these ranges include methyl, ethyl, propyl, isopropyl, n-butyl, sec-butyl, isobutyl, tert-butyl, pentyl, isoamyl, hexyl, and the like. The number of carbons referred to relates to the carbon backbone and carbon branching but does not include carbon atoms belonging to any substituents, for example the carbon atoms of an alkoxy substituent branching off the main carbon chain. In certain embodiments, the reference to an alkyl group may be reference to a tertiary alkyl group.

The term "alkyl aryl" refers to a carbon chain which terminates in an aryl group. Both 'alkyl' and 'aryl' may be any such group as defined herein. In certain embodiments the alkyl chain may be a $C_1$ to $C_6$ alkyl chain and the aryl group may be a phenyl, each of which may be substituted or unsubstituted.

The term "alkenyl," as used herein, means a linear alkenyl substituent containing at least one carbon-carbon double bond and from, for example, 2 to 6 carbon atoms (branched alkenyls are 3 to 6 carbons atoms), preferably from 2 to 5 carbon atoms (branched alkenyls are preferably from 3 to 5 carbon atoms), more preferably from 3 to 4 carbon atoms. Examples of such substituents considered to be included within these ranges include vinyl, propenyl, isopropenyl, n-butenyl, sec-butenyl, isobutenyl, tert-butenyl, pentenyl, isopentenyl, hexenyl, and the like.

The term "alkynyl," as used herein, means a linear alkynyl substituent containing at least one carbon-carbon triple bond and from, for example, 2 to 6 carbon atoms (branched alkynyls are 3 to 6 carbons atoms), preferably from 2 to 5 carbon atoms (branched alkynyls are preferably from 3 to 5 carbon atoms), more preferably from 3 to 4 carbon atoms. Examples of such substituents considered to be included within these ranges include ethynyl, propynyl, isopropynyl, n-butynyl, sec-butynyl, isobutynyl, tert-butynyl, pentynyl, isopentynyl, hexynyl, and the like.

The term "alkylalkanoate" may be used herein interchangeably with the term 'ester' and refers to an ester moiety being one that comprises up to 20 carbon atoms, preferably 12, more preferably 9, even more preferably 6 carbon atoms as a backbone and wherein the carbonyloxy component may be located anywhere along the 20 carbon backbone. The backbone may be substituted particularly with $C_1$ to $C_6$ alkyl or $C_1$ to $C_6$ alkoxy. In certain embodiments the group referred to may be one with an alkyl chain only at the terminal end of the group, such as carbomethoxy. In certain embodiments, the terms may be used to refer to a group comprising an alkyl chain both before the carbonyl carbon and then following the ether oxygen. In embodiments, the term "ester" may also include an aryl group following the ether oxygen.

The term "cycloalkyl" refers to optionally substituted saturated mono-cyclic, bicyclic or tricyclic carbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

The term "cycloalkenyl" refers to optionally substituted mono-cyclic, bicyclic or tricyclic carbon groups having at least one double bond. Where appropriate, the cycloalkenyl group may have a specified number of carbon atoms, for example, $C_3$-$C_6$ cycloalkenyl is a carbocyclic group having 3, 4, 5 or 6 carbon atoms. Non-limiting examples may include cyclopentenyl, cyclohexenyl, cyclohexadienyl and the like.

The term "aryl" refers to an unsubstituted or substituted aromatic carbocyclic substituent, as commonly understood in the art. It is understood that the term aryl applies to cyclic substituents that are planar and comprise $4n+2\pi$ electrons, according to Hückel's Rule. Phenyl is a preferred aryl group.

The term "heteroaryl" refers to an aryl group containing from one or more (particularly one to four) non-carbon atom(s) (particularly N, O or S) or a combination thereof, which heteroaryl group is optionally substituted at one or more carbon or nitrogen atom(s). Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms such as triazines (e.g., 1,3,5-triazine); and 6-membered heteroaryls with four heteroatoms. "Substituted heteroaryl" means a heteroaryl having one or more non-interfering groups as substituents.

"Heterocyclic" or "heterocycle" refers to an aromatic or non-aromatic ring having 5 to 7 atoms in the ring and of those atoms 1 to 4 are heteroatoms, said ring being isolated or fused to a second ring wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated. Preferred heterocyclic rings are nitrogen heterocycles. Non-limiting examples of heterocyclic include indoline, pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

"Alkanoyl" means alkanoyl groups of a straight or branched configuration and of the specified number of carbon atoms. By way of non-limiting example, alkanoyl may be selected from acetyl, propionoyl, butyryl, isobutyryl, pentanoyl and hexanoyl.

Whenever a range of the number of atoms in a structure is indicated (e.g., a $C_1$-$C_{20}$, $C_1$-$C_{12}$, $C_1$-$C_{10}$, $C_1$-$C_9$, $C_1$-$C_6$, $C_1$-$C_4$, or $C_2$-$C_{20}$, $C_2$-$C_{12}$, $C_2$-$C_{10}$, $C_2$-$C_9$, $C_2$-$C_8$, $C_2$-$C_6$, $C_2$-$C_4$ alkyl, alkenyl, alkynyl, alkoxy, alkylalkanoate, haloalkyl, alkanoyl etc.), it is specifically contemplated that any sub-range or individual number of carbon atoms falling within the indicated range also can be used. Thus, for instance, the recitation of a range of 1-20 carbon atoms (e.g., $C_1$-$C_{20}$), 1-12 carbon atoms (e.g., $C_1$-$C_{12}$), 1-10 carbon atoms (e.g., $C_1$-$C_{10}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkanoyl, etc.) referenced herein encompasses and specifically describes 1, 2, 3, 4, 5, 6, 7, 8, 9, 10, 11, 12, 13, 14, 15, 16, 17, 18, 19 and/or 20 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 1-18 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 2-18 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In any of the embodiments described the term "substituted" (such as is referred to in 'substituted or unsubstituted, or 'optionally substituted' and the like) may refer to substitution of that moiety with a group selected from the group consisting of alkyl, alkenyl, alkylalkanoate, aryl, alkylaryl, heteroaryl, heterocyclyl, alkynyl, aroyl, alkanone, cycloalkyl, cycloalkanone, cycloalkenyl, alkanoyl, alkanoyloxy, alkoxycarbonyl, carbamoyl, carboxyl, halo, cyano, nitro, haloalkyl, N-alkyl, N-aryl and N-heterocyclyl. Each of these groups may themselves be substituted with the same or different groups. The carbon chains may be $C_1$ to $C_{20}$ or $C_2$ to $C_{20}$, as appropriate and these ranges include all sub-ranges of $C_1$ to $C_{12}$ or $C_2$ to $C_{12}$, $C_1$ to $C_9$ or $C_2$ to $C_9$, $C_1$ to $C_6$ or $C_2$ to $C_6$ and $C_1$ to $C_4$ or $C_2$ to $C_4$. Each cyclic structure listed above may be $C_4$ to $C_7$, preferably $C_5$ or $C_6$ and may be fused with one or more other cyclic structures.

It will be appreciated by the person of skill in the art that the compounds of the first aspect will, due to the enamine core double bond, present as geometric isomers, such as cis/trans and E/Z isomers. While drawn in one configuration herein for the sake of convenience, it should be appreciated that all compounds of the first aspect may be in the E or Z form and every structure drawn herein is explicitly considered to be represented in both the E and Z isomeric forms. Synthesis of the compounds of the first aspect may result in substantially pure forms of E or Z isomer or a mixture of E and Z forms, which forms may be used in any of the methods and applications described herein in that particular form. Similarly, it will be appreciated that in any aspect of the present invention when compounds of the first aspect are provided in a composition or formulation then each compound may be present in either substantially the E or substantially the Z isomeric form or may be present as a mixture of both.

Certain of the compounds of the first aspect may contain chiral centers, which may be either of the (R) or (S) configuration, or which may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention.

Compound Synthesis and Strategies
Fluorinated Compounds

The compounds of the first aspect may, in one embodiment, be synthesised in a one-pot procedure without the need for isolation of the intermediate enamines (Y and Z in the below scheme 1). In the example synthesis of compounds 142 and 143 shown in scheme 1 below, phenylacetaldehyde was chosen to allow ease of enamine formation by conjugation with the aromatic ring. The starting materials are both cheap and readily available on a large scale. A generalised approach is also outlined in scheme 1 whereby it can be seen how variation can be introduced to the synthesised compounds through use of a range of R, R' and R'' groups including alkyl, aryl and hydrogen. It should be noted that yields shown throughout the synthetic schemes shown herein have generally not been optimised, for example often only precipitated product was collected and remaining compound within liquors was not pursued, as the purpose was simply to obtain sufficient product for subsequent testing.

Scheme 1: Synthetic route to compounds 142 and 143 and generalised scheme.

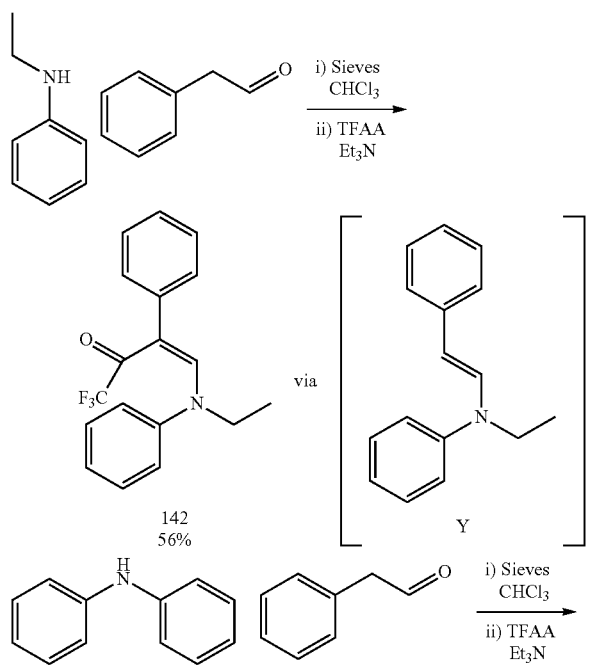

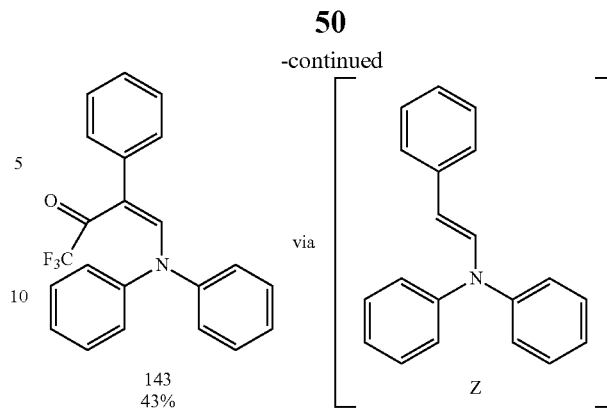

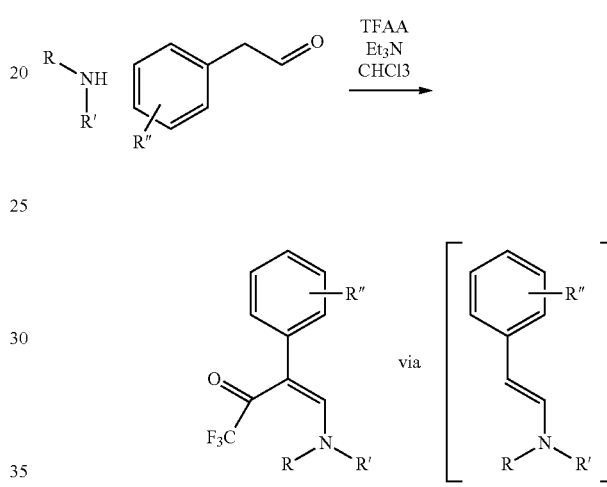

This general approach allowed access to a wide range of non-cyclic enamine compounds with varying substituents based on choice of reagents. Modifications of the scheme and use of the intermediates to access a variety of products provides for a means to tailor the final product in terms of lipophilicity, stability and absorbance maximum. It is noted that alterations can be made at the $R_2$ position by, in one embodiment, starting with 2-phenylacetophenone to place a phenyl group at $R_2$. It will be appreciated that analogous starting materials can provide variation at the $R_2$ position. Further, for formation of enamines where reactivity of the substrates may be low then slightly altered and more forcing conditions (for example, but not limited to, heating under dehydrating conditions including Dean-Stark conditions or molecular sieves and use of catalytic acid which may be a Bronsted or Lewis acid) and the separation of the two steps (so as to form the enamine isolate and then acylate this with TFAA separately) may be useful. These approaches and reaction conditions are known generally in the art and may be accessed in standard texts and journal articles including but not limited to J. AM. CHEM. SOC. 2006, 128, 11774-11775, Highly Efficient Rh(I)-Catalyzed Asymmetric Hydrogenation of Enamines Using Monodente Spiro Phosphonite Ligands and particularly the associated supporting information.

By way of selected examples only, alternative synthetic pathways to access a number of compounds of the invention are shown in scheme 2, below, leading to the numbered compounds.

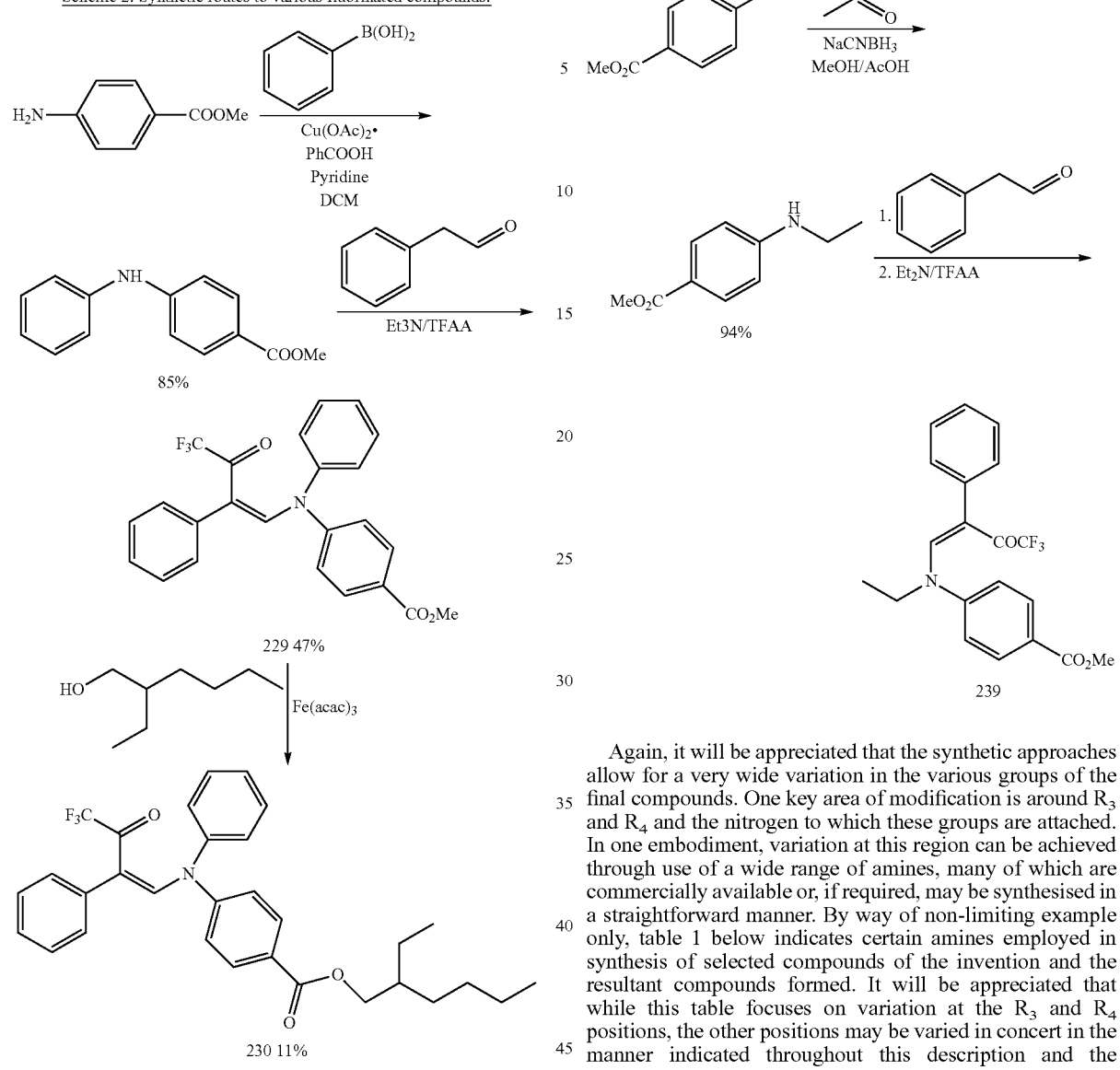

Again, it will be appreciated that the synthetic approaches allow for a very wide variation in the various groups of the final compounds. One key area of modification is around $R_3$ and $R_4$ and the nitrogen to which these groups are attached. In one embodiment, variation at this region can be achieved through use of a wide range of amines, many of which are commercially available or, if required, may be synthesised in a straightforward manner. By way of non-limiting example only, table 1 below indicates certain amines employed in synthesis of selected compounds of the invention and the resultant compounds formed. It will be appreciated that while this table focuses on variation at the $R_3$ and $R_4$ positions, the other positions may be varied in concert in the manner indicated throughout this description and the examples.

TABLE 1

Exemplary amine reactant variations.

TABLE 1-continued
Exemplary amine reactant variations.
| Amine | Product No. | Product |
|---|---|---|
| 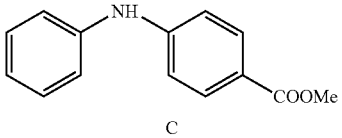 C | 230 | 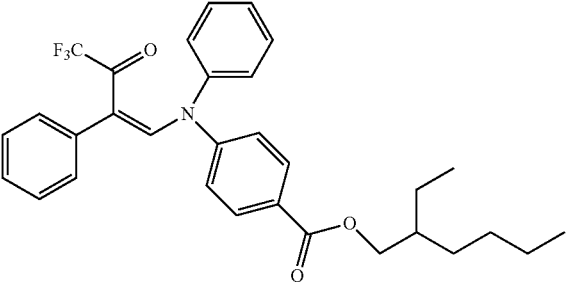 [SMILES: CCCCC(CC)COC(=O)c1ccc(N(/C=C(\C(=O)C(F)(F)F)c2ccccc2)c2ccccc2)cc1] |
| 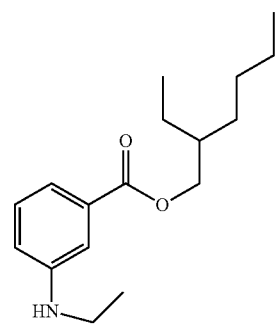 F | 232 | 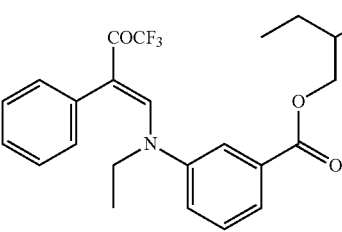 |
| 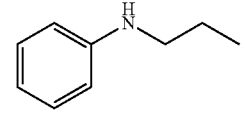 G | 233 | 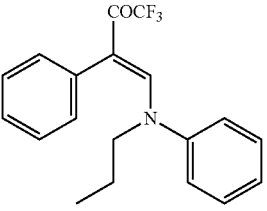 |
| 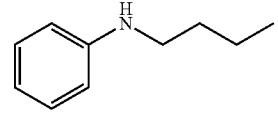 H | 234 | 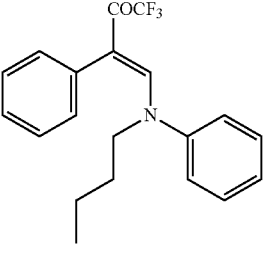 |
| 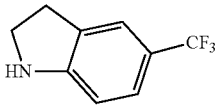 | 235 | 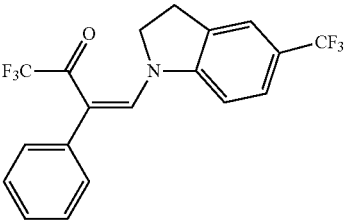 [SMILES: O=C(/C(=C\N1CCc2cc(C(F)(F)F)ccc21)c1ccccc1)C(F)(F)F] |

TABLE 1-continued

Exemplary amine reactant variations.

| Amine | Product No. | Product |
|---|---|---|
| (indoline-CF3), HN | 236 | F3C-C(=O)-C(Ph)=CH-N(indoline-CF3) |
| MeO2C-C6H4-NH-Et, I | 239 | COCF3, Ph, N(Et)-C6H4-CO2Me |
| Et-NH-(CH2)4-NH-Et, Q | 241 | F3COC-C(Ph)=CH-N(Et)-(CH2)4-N(Et)-CH=C(Ph)-COCF3 |
| Et-NH-(CH2)6-NH-Et, R | 242 | COCF3-C(Ph)=CH-N(Et)-(CH2)6-N(Et)-CH=C(Ph)-COCF3 |

Benzoyl and Alkanoyl Compounds

In certain embodiments, the compounds of the first aspect may display a benzoyl or alkanoyl moiety, that is, $R_5$ may comprise a phenyl group or a short chain alkyl group. Such compounds may be synthesised by a number of approaches and non-limiting examples are shown in the following schemes.

In scheme 3, the corresponding phenylacetophenone, S was reacted with N,N-dimethylformamide dimethyl acetal (DMFDMA) to give the dimethlyenamine intermediate 240. This could then undergo a transamination process to give the desired final compounds. Whilst transamination in the presence of p-toluenesulphonic acid worked satisfactorily for compound 243, it was found that the presence of acetic acid instead gave better results for compounds 244 and 245.

Scheme 3: Synthetic routes to benzoyl compounds.

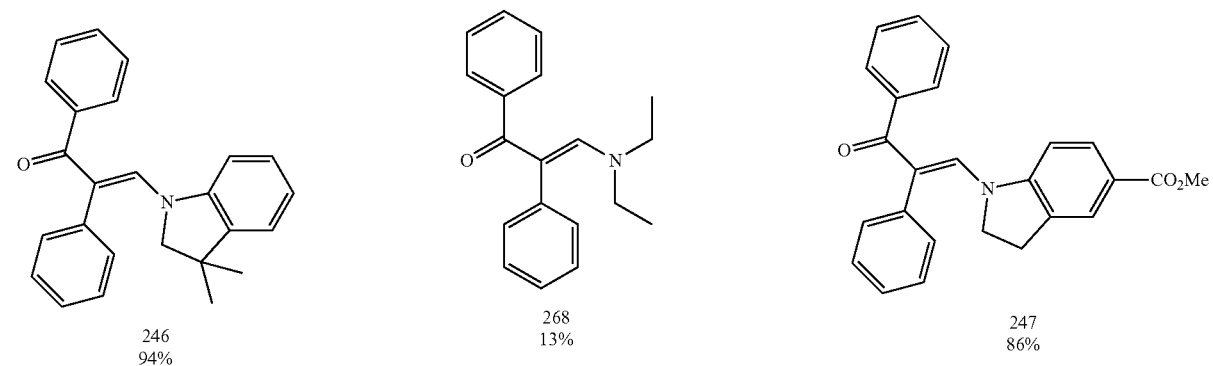

246
94%

268
13%

247
86%

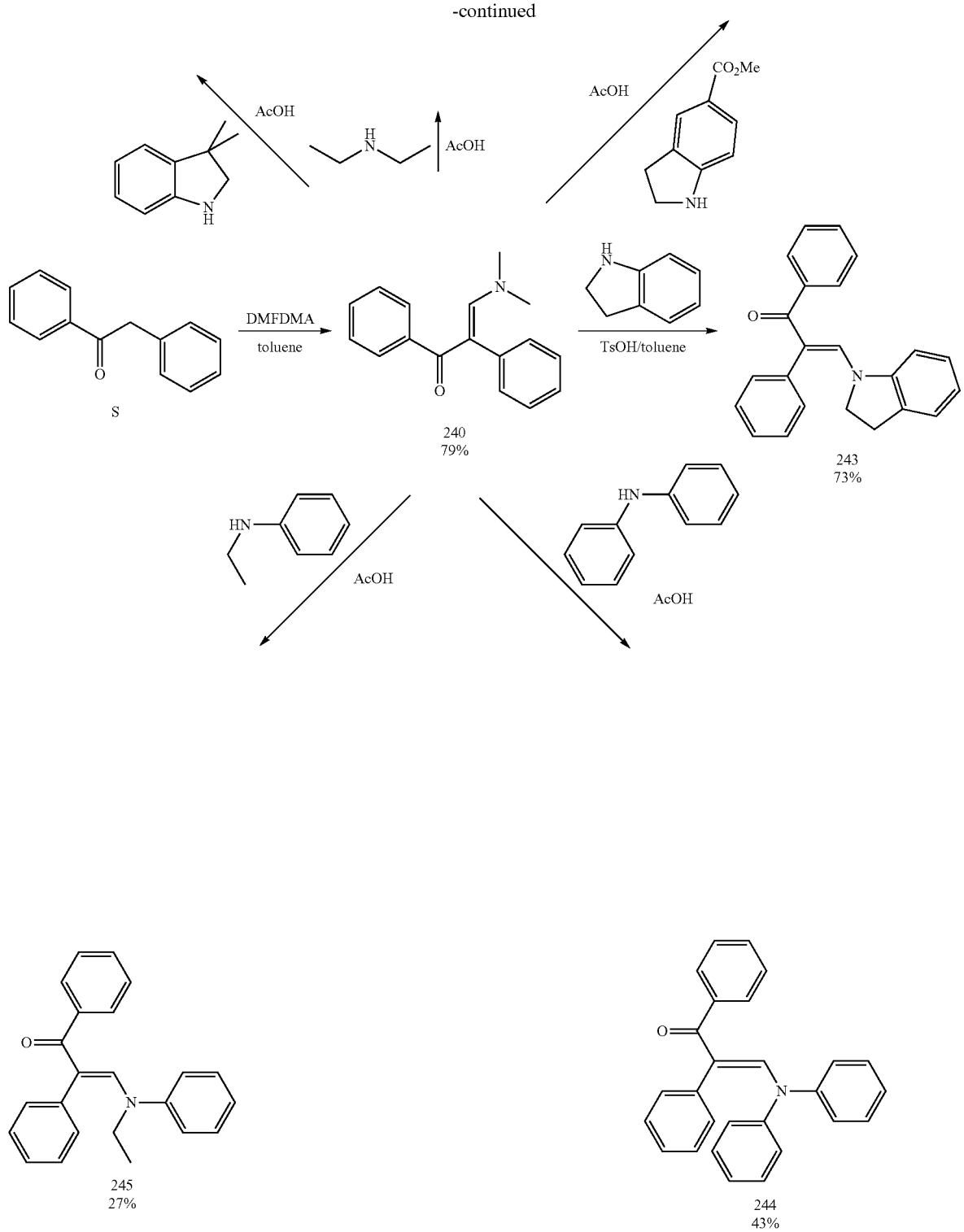

Schemes 4 to 7 exemplify a similar approach for the synthesis of the related 2-methyl, 4 methyl, 2,4,6-trimethyl and methoxy benzoyl compound derivatives. For these compounds, the corresponding phenylacetophenone was not commercially available and so was prepared via a coupling of benzylmagnesium chloride and the substituted benzaldehyde followed by oxidation of the intermediate alcohol. From a review of the schemes it will be appreciated that choice of the substitution on the benzaldehyde, from a wide range of both commercially available and easily synthesised alternatives, and subsequent selection of the reagent to introduce the nitrogen-containing group can result in the generation of significant compound diversity.

Scheme 4: Synthetic of 2-methylbenzoyl compounds.
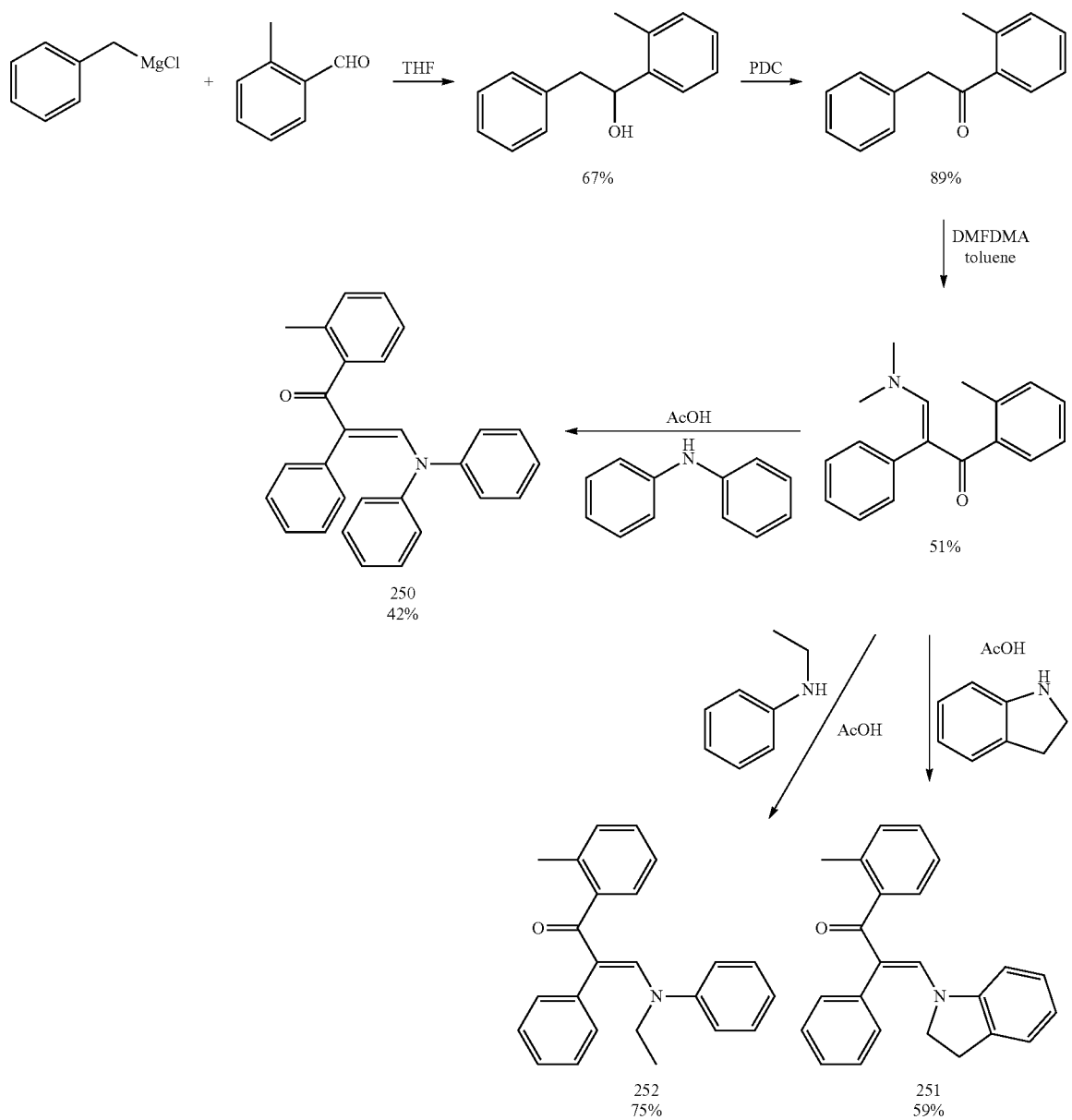
Scheme 5: Synthetic of 2,4,6-trimethylbenzoyl compounds.
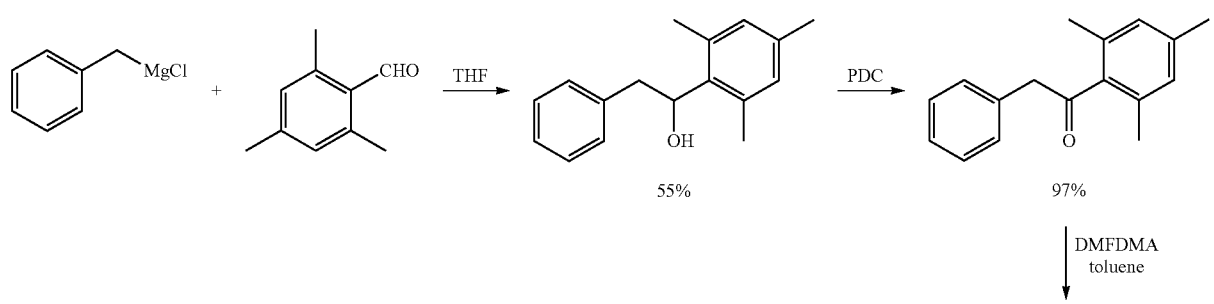

-continued
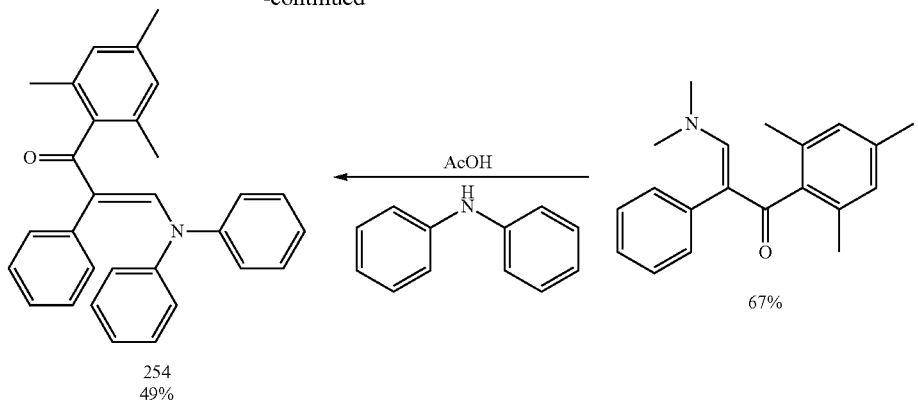
254
49%
67%
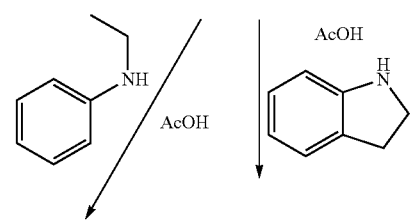
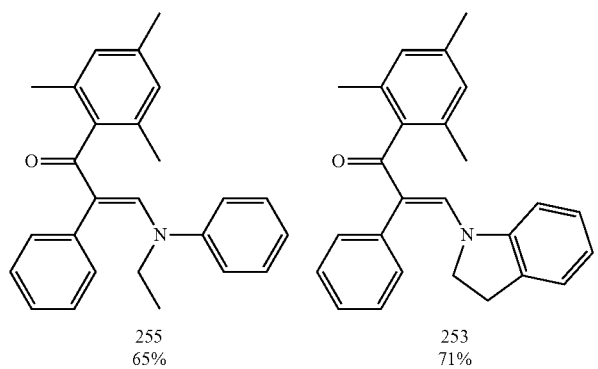
255
65%
253
71%
Scheme 6: Synthetic of 4-methylbenzoyl compounds.
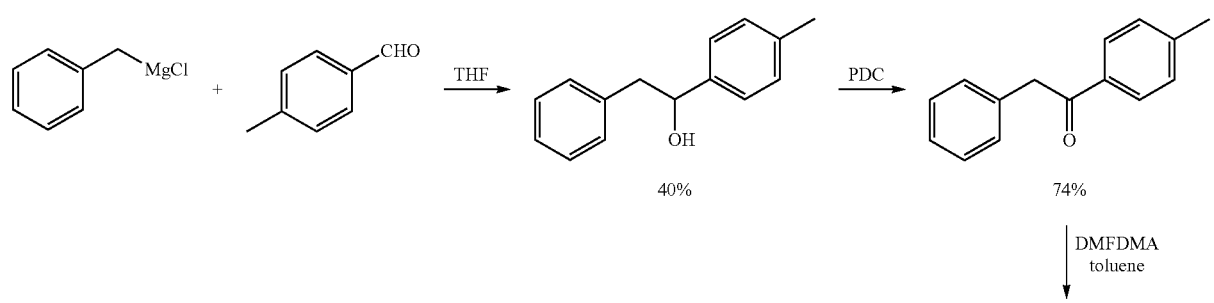
40%
74%
DMFDMA
toluene -continued
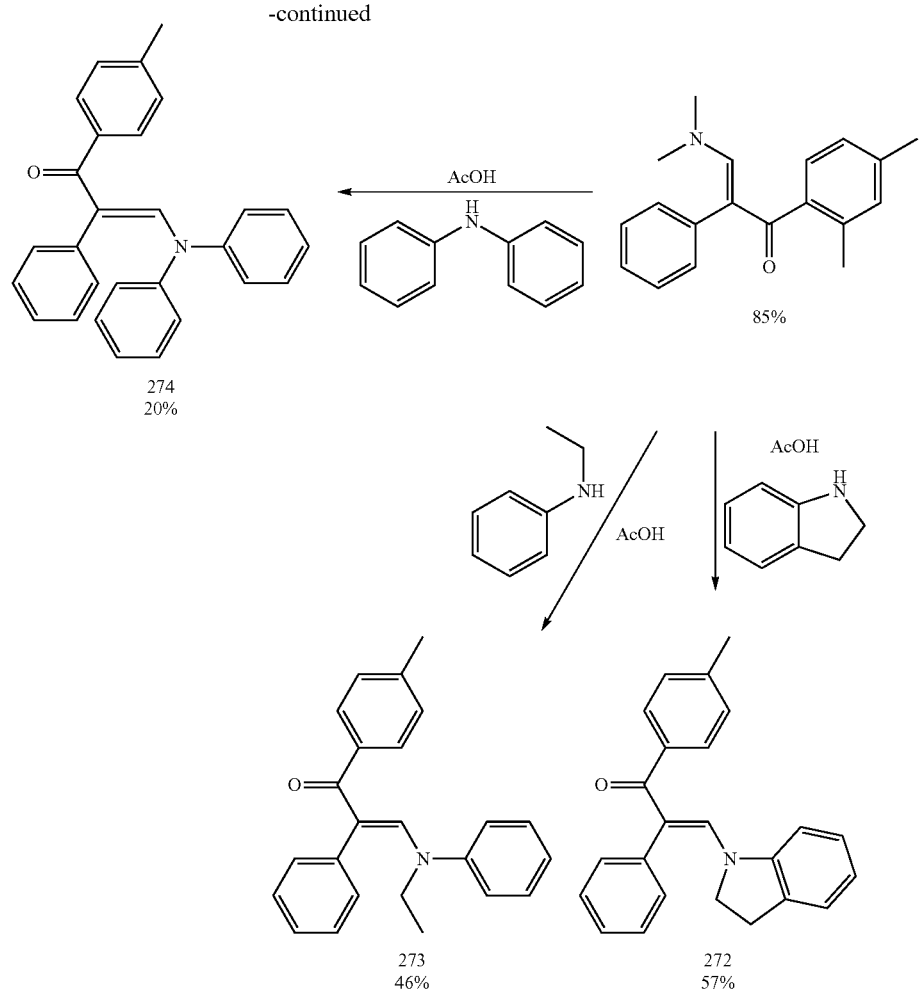
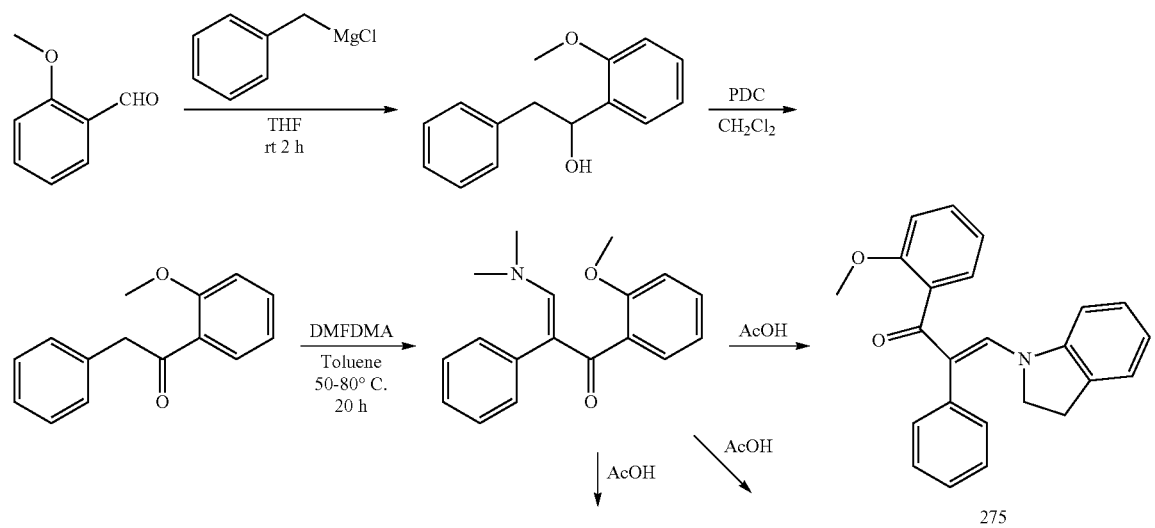
Scheme 7: Synthetic of 2-methoxybenzoyl compounds.

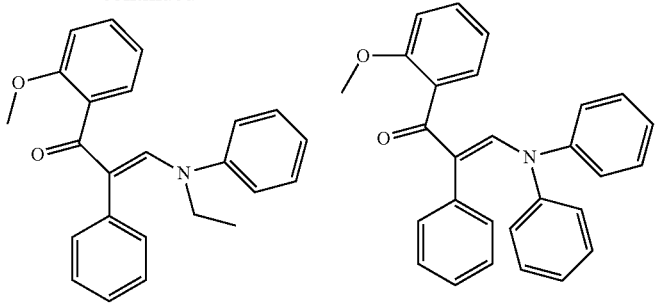

276

Yet a further approach is shown in scheme 8, below, to yield compounds displaying sulfonyl groups. Substituted phenylacetophenone, T was obtained via reduction of the corresponding Weinreb amide. Once T was in hand then standard enamine formation and transamination pathways as described were followed to access compounds 264-266.

Scheme 8: Synthesis of substituted phenylacetophenone T and corresponding compounds.

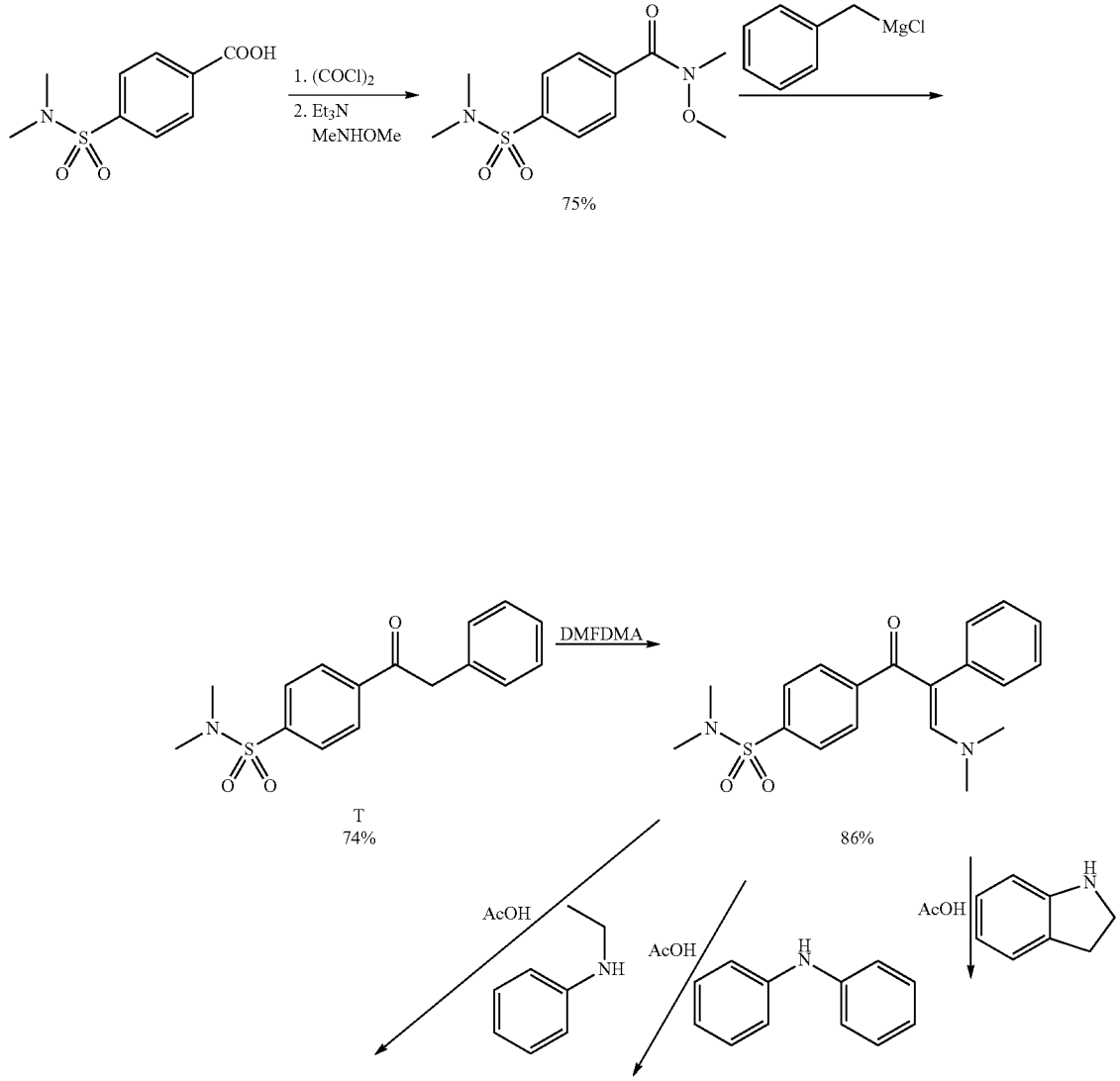

-continued

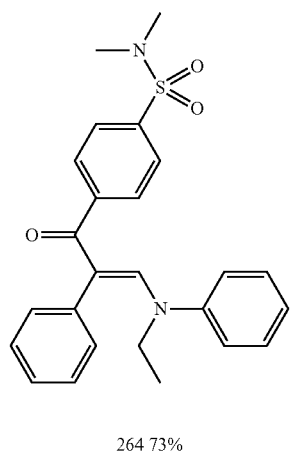

264 73%

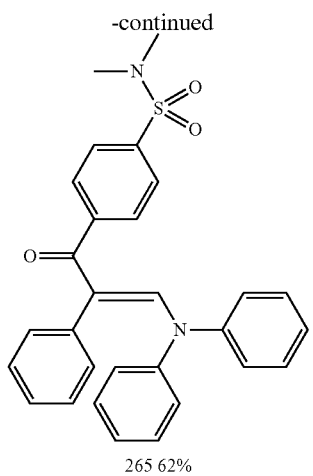

265 62%

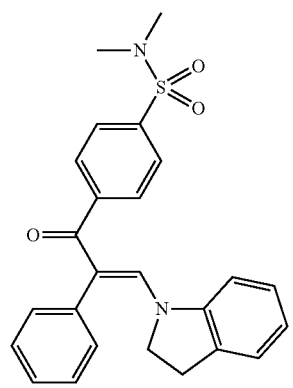

266 80%

The synthesised benzoyl functionalised compounds and their spectroscopic properties can be seen in table 2 wherein; breakthrough denotes the value in nm where transmittance increases beyond 1%; steepness refers to the distance in nm over which transmittance increases from 1 to 80% (a higher value indicates a less steep transition from absorbing to transmitting and is generally unfavourable); and [a] denotes an average of multiple measurements. As a general comment, it can be noted that the benzoyl substituted compounds gave similar absorbance maxima to the corresponding trifluoroacetyl derivative.

TABLE 2

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 142 | 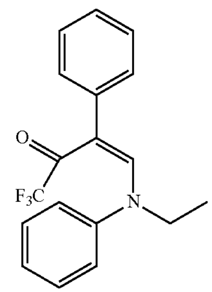 [SMILES: CCN(/C=C(\C(=O)C(F)(F)F)c1ccccc1)c1ccccc1] | 318 | 331 | 365 | 34708 | 1088 | 381 | 29 | 99 |
| 245 | 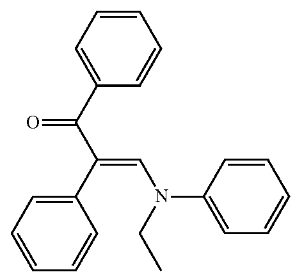 [SMILES: CCN(/C=C(/C(=O)c1ccccc1)c1ccccc1)c1ccccc1] | 327 | 333 | 374 | 20292 | 621 | 384 | 40 | 55 |
| 252 | 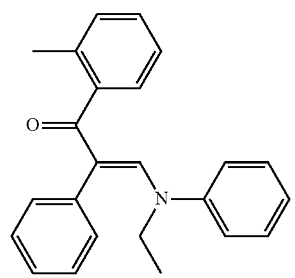 [SMILES: CCN(/C=C(/C(=O)c1ccccc1C)c1ccccc1)c1ccccc1] | 341 | 323 | 359 | 26295 | 771 | 373 | 39 | 48 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 255 | 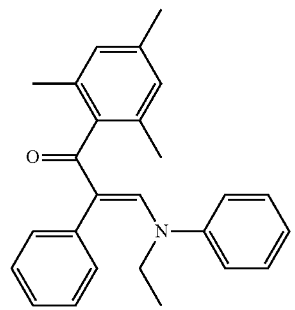 [SMILES: CCN(/C=C(/C(=O)c1c(C)cc(C)cc1C)c1ccccc1)c1ccccc1] | 369 | 323 | 351 | 29450 | 798 | 364 | 34 | 83[a] |
| 273 | 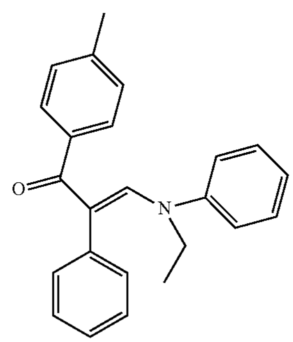 [SMILES: CCN(/C=C(/C(=O)c1ccc(C)cc1)c1ccccc1)c1ccccc1] | 341 | 336 | 376 | 20922 | 614 | 394 | 37 | 73 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 264 | 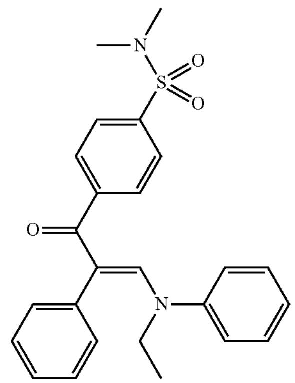 [SMILES: CCN(/C=C(/C(=O)c1ccc(S(=O)(=O)N(C)C)cc1)c1ccccc1)c1ccccc1] | 434 | 340 | 381 | 18791 | 433 | 403 | 46 | 20 |
| 143 | 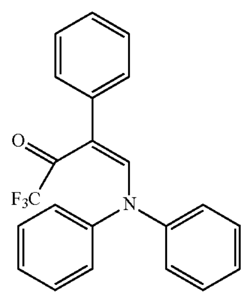 [SMILES: O=C(/C(=C\N(c1ccccc1)c1ccccc1)c1ccccc1)C(F)(F)F] | 367 | 351 | 381 | 27893 | 760 | 402 | 32 | Not soluble Assumed >98 |
| 244 | 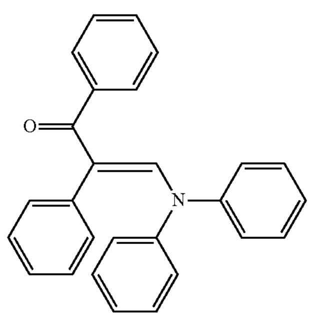 [SMILES: O=C(/C(=C/N(c1ccccc1)c1ccccc1)c1ccccc1)c1ccccc1] | 375 | 352 | 383 | 20114 | 536 | 407 | 43 | 58 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 250 | 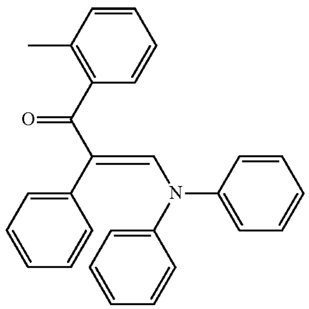 [SMILES: Cc1ccccc1C(=O)/C(=C/N(c1ccccc1)c1ccccc1)c1ccccc1] | 389 | 341 | 373 | 28714 | 738 | 389 | 37 | 60 |
| 254 | 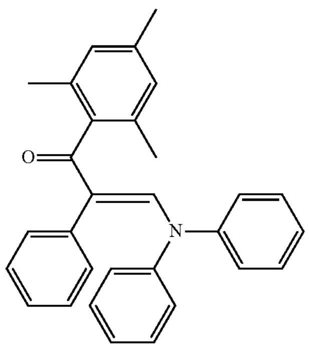 [SMILES: Cc1cc(C)c(C(=O)/C(=C/N(c2ccccc2)c2ccccc2)c2ccccc2)c(C)c1] | 417 | 341 | 369 | 27592 | 661 | 383 | 32 | 88[a] |
| 274 | 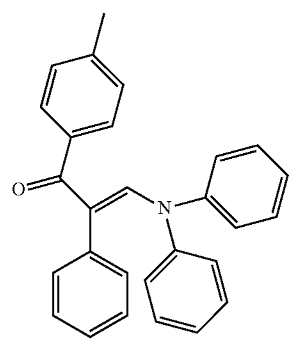 [SMILES: Cc1ccc(C(=O)/C(=C/N(c2ccccc2)c2ccccc2)c2ccccc2)cc1] | 389 | 353 | 384 | 16369 | 420 | 411 | 42 | 76 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 265 | 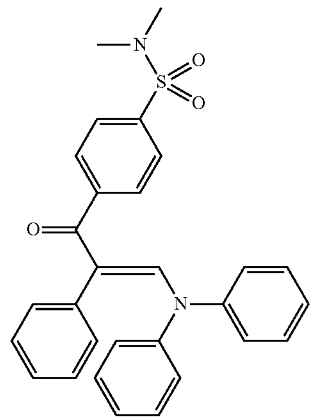 [SMILES: CN(C)S(=O)(=O)c1ccc(C(=O)/C(=C/N(c2ccccc2)c2ccccc2)c2ccccc2)cc1] | 482 | 360 | 387 | 15775 | 327 | 418 | 48 | N/A |
| 164 | 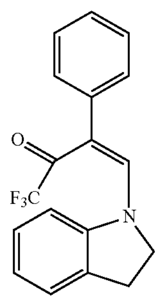 | 317 | 367 | 389 | 35741 | 1127 | 418 | 20 | 99 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 243 | | 325 | 361 | 386 | 29026 | 893 | 420 | 37 | 70 |
| 251 | | 339 | 355 | 378 | 33598 | 991 | 399 | 30 | 52 |
| 253 | | 367 | 355 | 375 | 34122 | 929 | 392 | 26 | 78 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 272 | 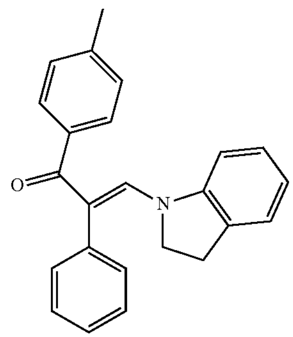 [SMILES: Cc1ccc(C(=O)/C(=C/N2CCc3ccccc32)c2ccccc2)cc1] | 339 | 362 | 386 | 30075 | 887 | 421 | 35 | 80 |
| 266 | 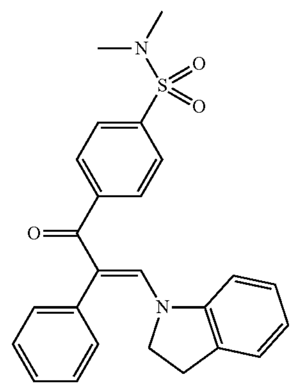 [SMILES: CN(C)S(=O)(=O)c1ccc(C(=O)/C(=C/N2CCc3ccccc32)c2ccccc2)cc1] | 432 | 368 | 390 | 23870 | 552 | 429 | 46 | N/A |
| 201 | 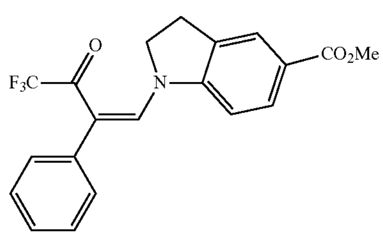 [SMILES: COC(=O)c1ccc2c(c1)CCN2/C=C(\C(=O)C(F)(F)F)c1ccccc1] | 375 | 373 | 391 | 46134 | 1230 | 420 | 18 | 97 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 247 | 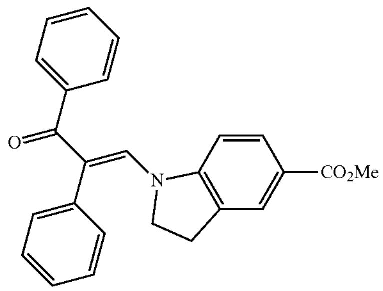 [SMILES: COC(=O)c1ccc2c(c1)CCN2/C=C(/C(=O)c1ccccc1)c1ccccc1] | 383 | 371 | 389 | 41977 | 1096 | 422 | 34 | 76 |
| 213 | 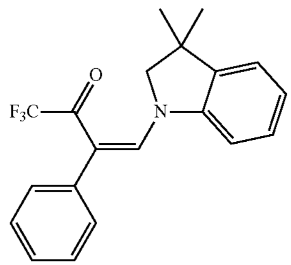 [SMILES: CC1(C)CN(/C=C(\C(=O)C(F)(F)F)c2ccccc2)c2ccccc21] | 345 | 366 | 389 | 29690 | 860 | 413 | 22 | |
| 246 | 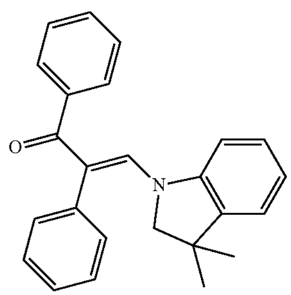 [SMILES: CC1(C)CN(/C=C(/C(=O)c2ccccc2)c2ccccc2)c2ccccc21] | 353 | 357 | 385 | 15933 | 451 | 405 | 43 | 53 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 144 | 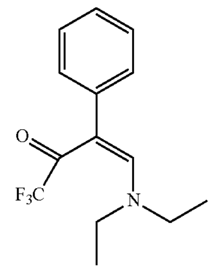 [SMILES: CCN(/C=C(\C(=O)C(F)(F)F)c1ccccc1)CC] | 271 | 319 | 350 | 23306 | 860 | | | 97 |
| 240 | 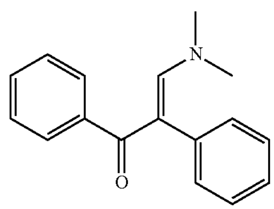 [SMILES: CN(C)/C=C(/C(=O)c1ccccc1)c1ccccc1] | 251 | 313 | 361 | 19475 | 776 | 379 | 40 | 10 |
| 268 | 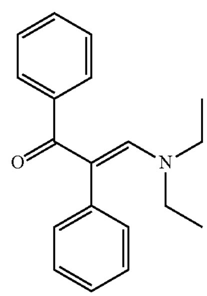 [SMILES: CCN(/C=C(/C(=O)c1ccccc1)c1ccccc1)CC] | 279 | 312 | 360 | 18293 | 656 | 374 | 48 | 10 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 286 | (structure with CO2Me, indoline, 3-methylphenyl benzoyl, phenyl) | 397 | 370 | 389 | 47867 | 1205 | 423 | 46 | N/A |
| 287 | (structure with CO2Me, indoline, 4-tert-butylphenyl benzoyl, phenyl) | 439 | 373 | 389 | 44238 | 1007 | 425 | 35 | 76 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 302 | 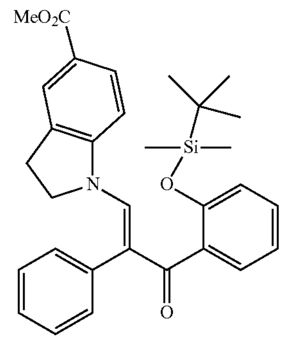 [SMILES: COC(=O)c1ccc2c(c1)CCN2/C=C(/C(=O)c1ccccc1O[Si](C)(C)C(C)(C)C)c1ccccc1] | 513 | 369 | 384 | 55852 | 1089 | 01 | 26 | 45 |
| 303 | 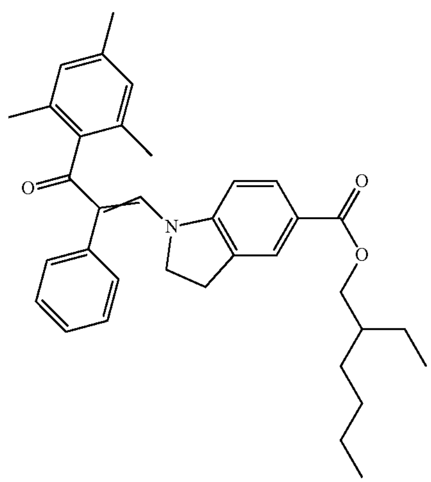 [SMILES: CCCCC(CC)COC(=O)c1ccc2c(c1)CCN2C=C(C(=O)c1c(C)cc(C)cc1C)c1ccccc1] | 523 | 369 | 382 | 60921 | 1164 | 399 | 24 | 94, 93 |

TABLE 2-continued

Properties of compounds displaying a benzoyl group and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 307 | *enlarged structure shown below | 862 | 370 | 384 | 107885 | 1251 | 402 | 22 | 98, 98 |
| 308 | 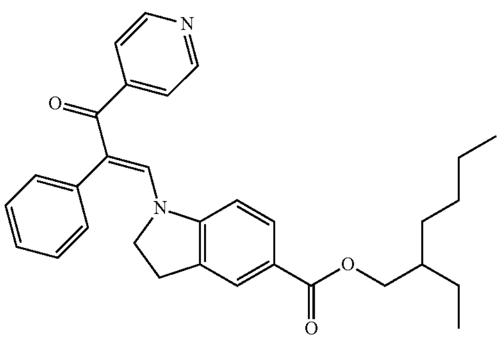 [SMILES: CCCCC(CC)COC(=O)c1ccc2c(c1)CCN2/C=C(/C(=O)c1ccncc1)c1ccccc1] | 482 | 374 | 391 | 38378 | 796 | 431 | 41 | 79 |

*Compound 307 structure-

In order to further test the effect of substitution on photostability in the benzoyl series the ortho-methoxy substituted analogues 275 and 276 were prepared. The methoxy derivatives were intermediate between the unsubstituted benzoyl and the ortho-methyl derivatives in terms of both $\lambda_{max}$ and $\lambda_{crit}$. Strength of absorbance was greater than that seen for the unsubstituted benzoyls and similar to the methyl derivatives. The photostability of compound 276 was found to be very similar to the o-methyl derivative with a useful value of 56% while compound 275 came in at 90 and 95% on two separate tests. These results are indicated in table 3 along with previously exemplified compounds, for comparison's sake.

Therefore, in one embodiment of the compound of the first aspect, when $R_5$ is aryl, such that a benzoyl compound is formed, it is preferred that the aromatic ring of the benzoyl (phenyl) is substituted.

TABLE 3

Properties of methoxy benzoyl compounds and comparators.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 245 | 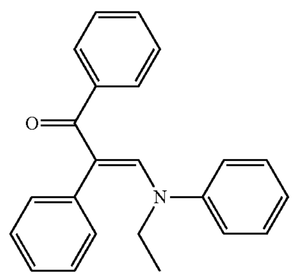 [SMILES: CCN(/C=C(/C(=O)c1ccccc1)c1ccccc1)c1ccccc1] | 327 | 5.9 | 333 | 374 | 20292 | 621 | >95 | Breakthrough 394 Steepness 40 Photostability 55 |
| 252 | 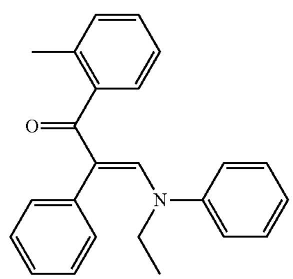 [SMILES: CCN(/C=C(/C(=O)c1ccccc1C)c1ccccc1)c1ccccc1] | 341 | 6.4 | 323 | 359 | 26295 | 771 | >95 | Breakthrough 372 Steepness 39 Photostability 48 |
| 276 | 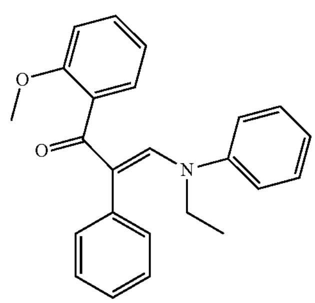 [SMILES: CCN(/C=C(/C(=O)c1ccccc1OC)c1ccccc1)c1ccccc1] | 357 | 6.2 | 327 | 366 | 25385 | 711 | >95 | Breakthrough 379 Steepness 40 |
| 243 | 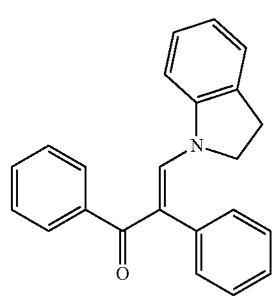 [SMILES: O=C(/C(=C/N1CCc2ccccc21)c1ccccc1)c1ccccc1] | 325 | 5.7 | 361 | 386 | 29026 | 893 | >95 | Breakthrough 420 Steepness 37 Photostability 70 |

TABLE 3-continued

Properties of methoxy benzoyl compounds and comparators.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 251 | 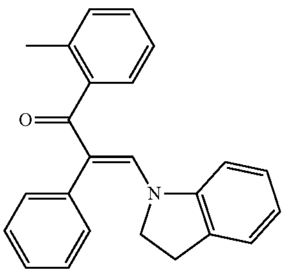 [SMILES: Cc1ccccc1C(=O)/C(=C/N1CCc2ccccc21)c1ccccc1] | 339 | 6.2 | 355 | 378 | 33598 | 991 | >95 | Breakthrough 399 Steepness 30 Photostability 52 |
| 275 | 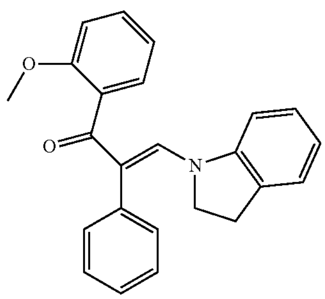 [SMILES: COc1ccccc1C(=O)/C(=C/N1CCc2ccccc21)c1ccccc1] | 355 | 5.8 | 358 | 383 | 38139 | 1074 | >95 | Breakthrough 406 Steepness 30 Photostability 56 |

All compounds were found to be soluble in most organic solvents.

It will also be appreciated by a skilled chemist that the methoxy compounds can be transformed into their hydroxyl analogues. One possible route is shown in scheme 9 below.

Scheme 9: Methoxy group transformation.

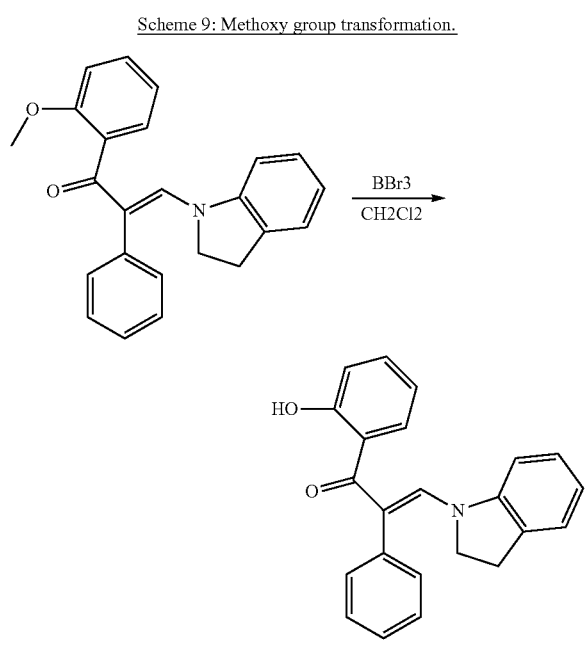

In order to further test the effect of substitution on photostability in the benzoyl series, the 5 carbomethoxy indoline derivatives, which can be seen to be the most photostable of the various amines used, of both the trimethyl benzoyl series 282 and the 4-methyl series 284 were prepared (scheme 13). The selected data is shown in table 4a. Both compounds are very strong absorbers with 282 showing a steep transmittance curve and a breakthrough of 402 nm to give a compound with similar UV-transmittance properties to compound 129. Compound 282 proved to have a critical wavelength of 382 nm and features a very steep drop off in absorbance at approximately 390 nm. The photostability was found to be 89 and 91% on two separate tests.

Compound 285 is the diphenylamine based derivative of the 2-methoxybenzoyl series. Compound 283 was synthesised to incorporate a tertiary alkyl group into the compound in place of the phenyl moiety. It possesses a very strong absorbance in conjunction with a very steep transmittance curve. This gave a compound with a breakthrough of 401 nm and a critical wavelength of 384 nm but which still gave a colourless solution at 0.1% by mass. The photostability was found to be 87 and 88% on two separate tests. As with compound 282, this compound compares very favourably with compound 129, as a comparator absorbing compound. The selected data for t-alkanoyl compounds is shown in table 4b.

TABLE 4a
Data for selected benzoyl compounds and comparators.
| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 129 | 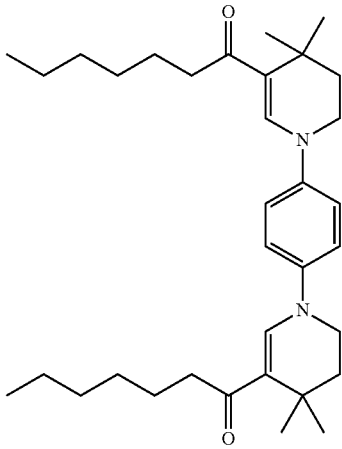 [SMILES: CCCCCCC(=O)C1=CN(c2ccc(N3C=C(C(=O)CCCCCC)C(C)(C)CC3)cc2)CCC1(C)C] | 520 | 10.51 | 359<br>359 | 378<br>378 | 60809<br>70222 | 1169<br>1350 | >90<br>>95 | Steepness 20<br>Breakthrough 397 |
| 253 | 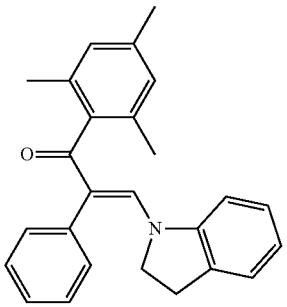 [SMILES: Cc1cc(C)c(C(=O)/C(=C/N2CCc3ccccc32)c2ccccc2)c(C)c1] | 367 | 7.2 | 355 | 375 | 34122 | 929 | >95 | Photostability 78%<br>Breakthrough 392<br>Steepness 26 |
| 282 | 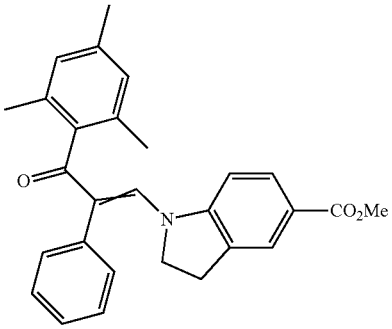 [SMILES: COC(=O)c1ccc2c(c1)CCN2C=C(C(=O)c1c(C)cc(C)cc1C)c1ccccc1] | 425 | 7.4 | 368 | 382 | 60650 | 1427 | >95 | Photostability 89, 91%<br>Breakthrough 402<br>Steepness 23 |
| 272 | 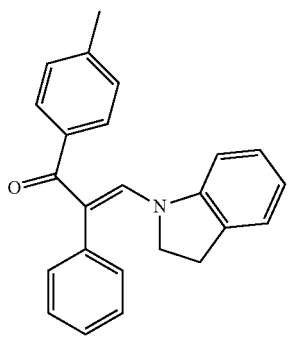 [SMILES: Cc1ccc(C(=O)/C(=C/N2CCc3ccccc32)c2ccccc2)cc1] | 339 | 6.2 | 362 | 386 | 30075 | 887 | >95 | Photostability 80%<br>Breakthrough 421<br>Steepness 35 |

TABLE 4a-continued

Data for selected benzoyl compounds and comparators.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 284 | 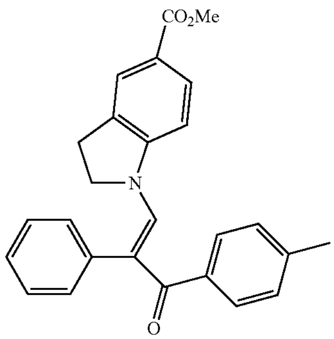 [SMILES: COC(=O)c1ccc2c(c1)CCN2/C=C(/C(=O)c1ccc(C)cc1)c1ccccc1] | 397 | 6.4 | 371 | 389 | 45689 | 1150 | >95 | Breakthrough 423 Steepness 30 |
| 250 | 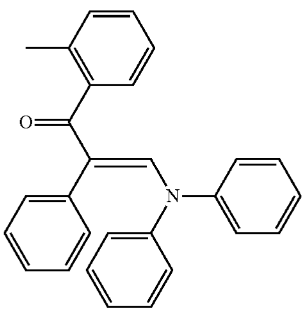 [SMILES: Cc1ccccc1C(=O)/C(=C/N(c1ccccc1)c1ccccc1)c1ccccc1] | 389 | 7.4 | 341 | 373 | 28714 | 738 | >95 | Photostability 60% Breakthrough 389 Steepness 37 |
| 285 | 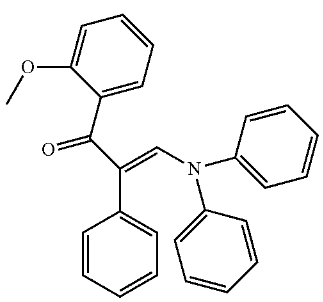 [SMILES: COc1ccccc1C(=O)/C(=C/N(c1ccccc1)c1ccccc1)c1ccccc1] | 406 | 6.7 | 345 | 378 | 27034 | 666 | >95 | Photostability 76% Breakthrough 398 Steepness 34 |

TABLE 4b

Data for selected t-alkanoyl compounds.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 295 | 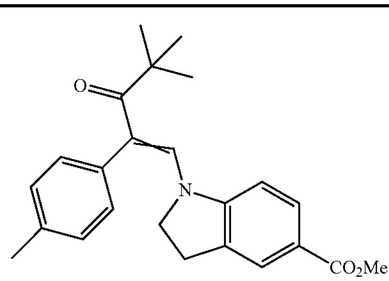 | 377 | 6.2 | 368 | 385 | 49288 | 1307 | >95 | Breakthrough 402 Steepness 16 Photostability 68 |

TABLE 4b-continued

Data for selected t-alkanoyl compounds.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 296 | 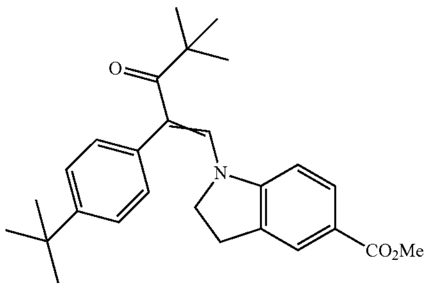 [SMILES: COC(=O)c1ccc2c(c1)CCN2C=C(C(=O)C(C)(C)C)c1ccc(C(C)(C)C)cc1] | 419 | 7.5 | 368 | 384 | 50838 | 1213 | >95 | Breakthrough 401 Steepness 16 Photostability 73 |
| 300 | 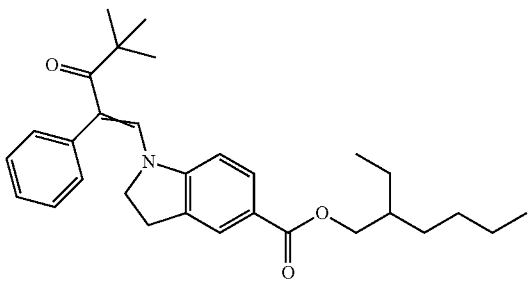 [SMILES: CCCCC(CC)COC(=O)c1ccc2c(c1)CCN2C=C(C(=O)C(C)(C)C)c1ccccc1] | 461 | 9.3 | 367 | 384 | 54826 | 1189 | >95 | Breakthrough 400 Steepness 16 Photostability 81, 83 |
| 304 | *enlarged structure below | 738 | 11.5 | 365 | 384 | 75535 | 1023 | >95 | Breakthrough 401 Steepness 19 Photostability 90, 92 |
| 283 | 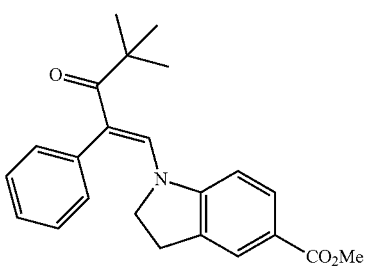 [SMILES: COC(=O)c1ccc2c(c1)CCN2/C=C(/C(=O)C(C)(C)C)c1ccccc1] | 363 | 5.7 | 367 | 384 | 48637 | 1339 | >95 | Photostability 87, 88% Breakthrough 401 Steepness 16 |
| 294 | 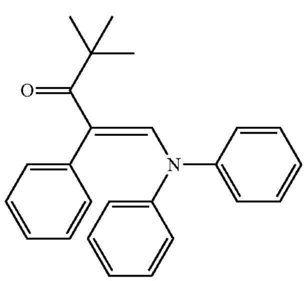 [SMILES: CC(C)(C)C(=O)/C(=C/N(c1ccccc1)c1ccccc1)c1ccccc1] | 355 | 6.6 | 344 | 373 | 17462 | 492 | >95 | Breakthrough 383 Steepness 28 |

TABLE 4b-continued

Data for selected t-alkanoyl compounds.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 309 | 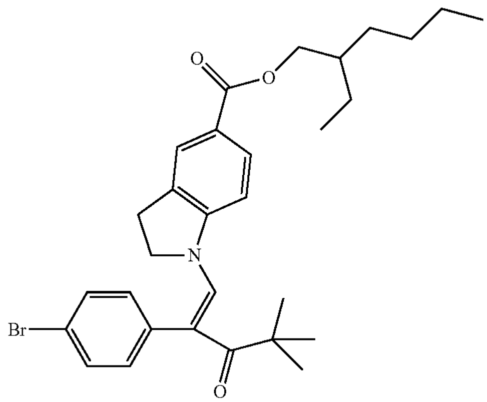 [SMILES: CCCCC(CC)COC(=O)c1ccc2c(c1)CCN2/C=C(/C(=O)C(C)(C)C)c1ccc(Br)cc1] | 539 | 10.1 | 366 | 384 | 42050 | 780 | >95 | Photostability 80 Steepness 19 Breakthrough 397 |
| 310 | 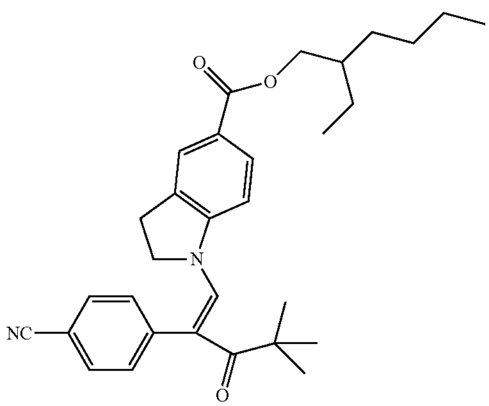 [SMILES: CCCCC(CC)COC(=O)c1ccc2c(c1)CCN2/C=C(/C(=O)C(C)(C)C)c1ccc(C#N)cc1] | 486 | 8.7 | 368 | 385 | 50502 | 1039 | >95 | Photostability 78, 81 Steepness 22 Breakthrough 402 |

* Compound 304 structure-

1,2-Dicarbonyl Compounds

A series of 1,2-dicarbonyl functionalised compounds was prepared with the synthesis generally performed using a modification of the standard synthetic procedure as shown in scheme 9.

Scheme 9: Synthesis of 1,2-dicarbonyl derivatives.

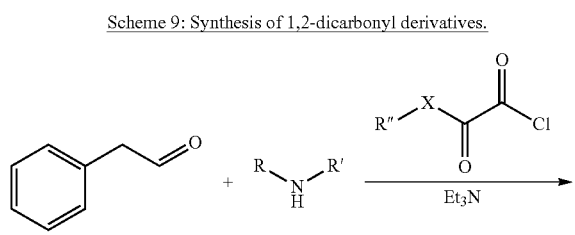

-continued

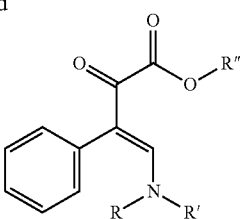

In the case of ethyl chlorooxoacetate (X=O, R″=Et) this reagent was commercially available. The corresponding t-butyl derivative (X=O, R″=tBu) could be prepared in almost quantitative yield from the reaction of oxalyl chloride and tert-butyl alcohol via a modification of a literature procedure. This meant a wide variation could be achieved at this position. In addition to these ester functionalised reagents, compounds with an amide functionality were also prepared. The products could be accessed through formation of the corresponding acid chloride.

Schemes 10 and 11, below, show selected exemplary pathways to a variety of 1,2-dicarbonyl compounds of the first aspect. Scheme 11 indicates that a variety of such compounds can be made with ester functionalities. Similarly, this approach can be used with a variation in reactant to instead generate an amide functionality, as per scheme 10.

Scheme 10: Synthesis of a 1,2-dicarbonyl compound displaying an amide functionality.

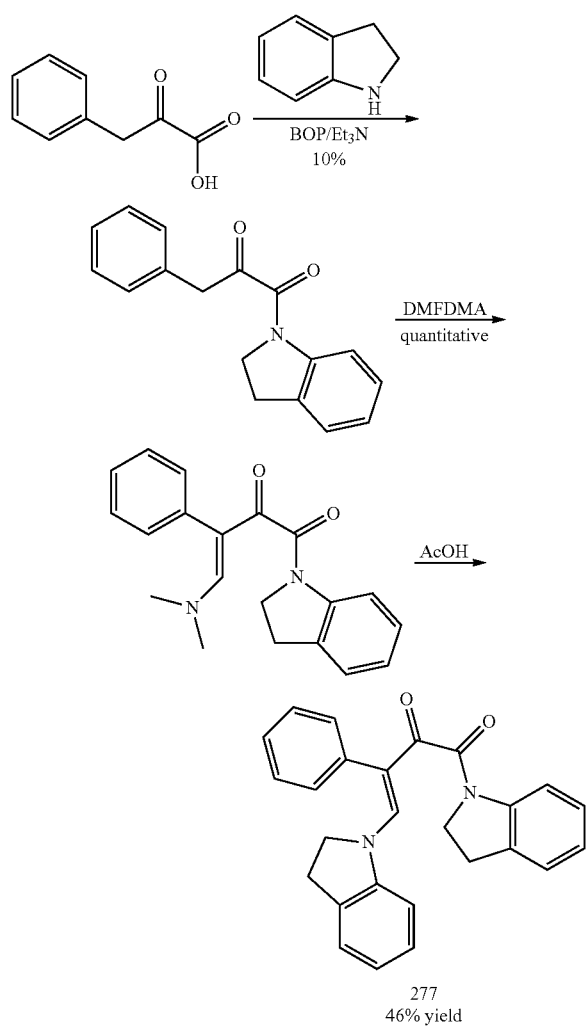

277
46% yield

Scheme 11: Synthesis of a 1,2-dicarbonyl compound displaying an ester functionality

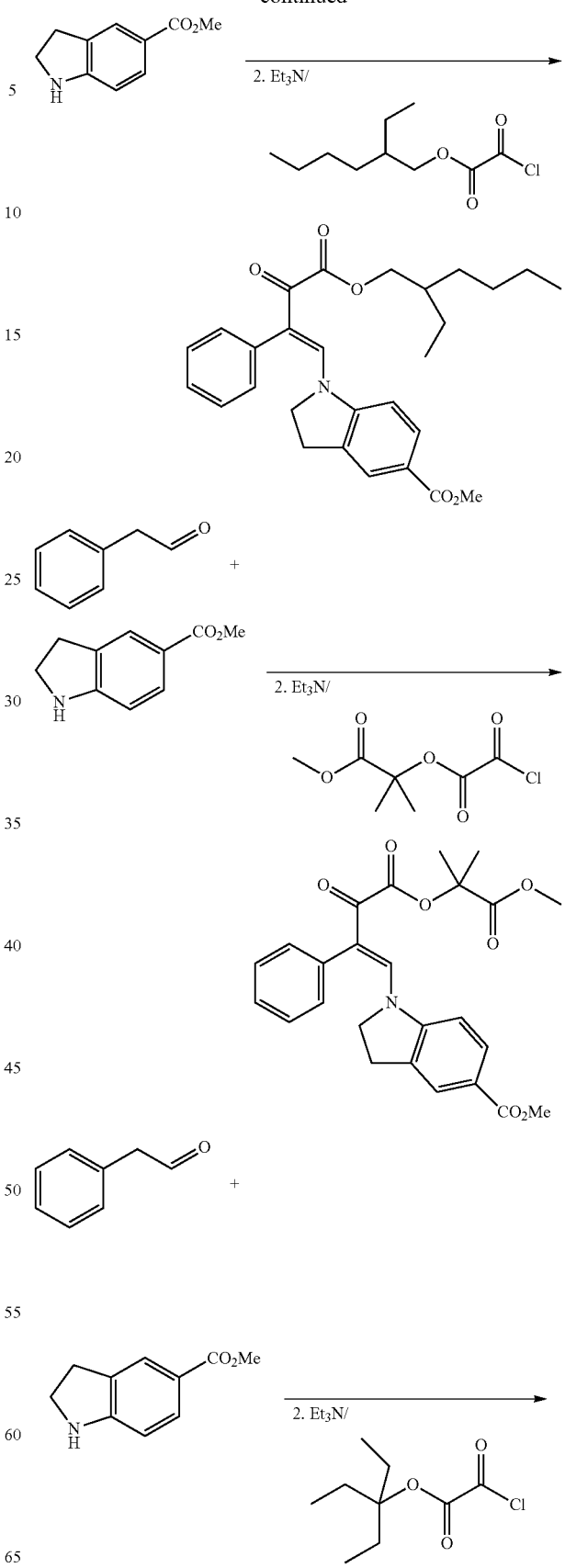

107

-continued

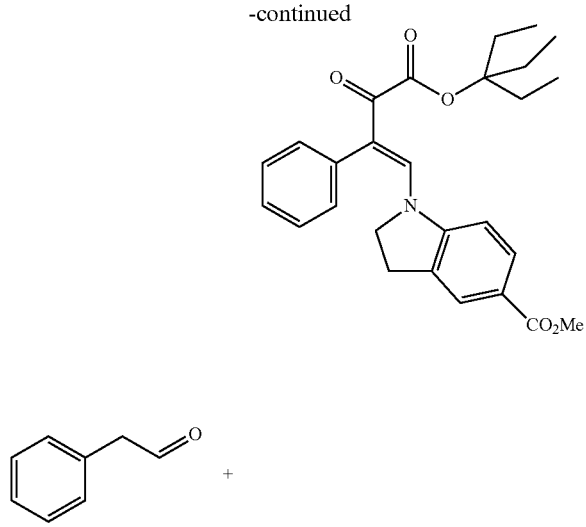

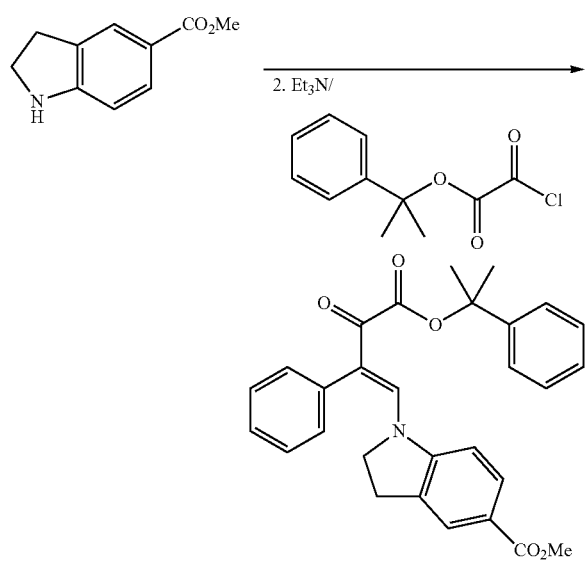

108

-continued

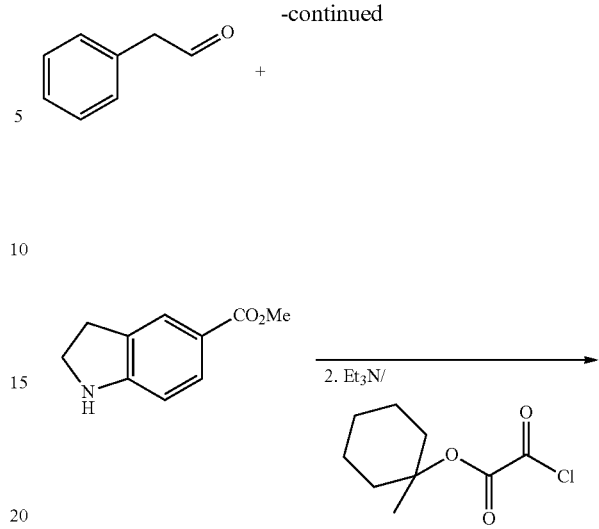

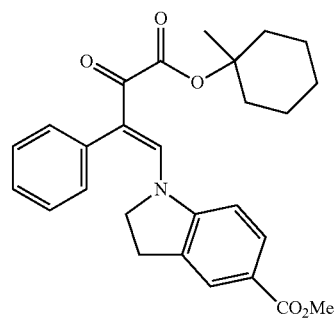

Table 5 indicates non-limiting examples of acylating agent and amine used in the generation of certain 1,2-dicarbonyl compounds of the first aspect. It will be appreciated that these examples could easily be expanded upon and further cross combinations of groups used to generate many more such compounds.

TABLE 5

| 1,2-Dicarbonyl analogues. | | | | |
|---|---|---|---|---|
| Acylating Agent | Amine | No. | Product | Yield (%) |
| ethyl oxalyl chloride | diethylamine | 260 | ethyl (E)-2-oxo-4-(diethylamino)-3-phenylbut-3-enoate | 80 |

TABLE 5-continued 1,2-Dicarbonyl analogues.

| Acylating Agent | Amine | No. | Product | Yield (%) |
|---|---|---|---|---|
| ethyl oxalyl chloride | N-ethylaniline | 248 | ethyl 2-oxo-4-(N-ethyl-N-phenylamino)-3-phenylbut-3-enoate | 15 |
| ethyl oxalyl chloride | diphenylamine | 237 | ethyl 2-oxo-4-(N,N-diphenylamino)-3-phenylbut-3-enoate | 48 |
| ethyl oxalyl chloride | indoline | 231 | ethyl 2-oxo-4-(indolin-1-yl)-3-phenylbut-3-enoate | 25 |
| ethyl oxalyl chloride | methyl indoline-5-carboxylate | 256 | ethyl 2-oxo-4-(5-methoxycarbonylindolin-1-yl)-3-phenylbut-3-enoate | 41 |
| tert-butyl oxalyl chloride | N-ethylaniline | 271 | tert-butyl 2-oxo-4-(N-ethyl-N-phenylamino)-3-phenylbut-3-enoate | 10 |

TABLE 5-continued 1,2-Dicarbonyl analogues.

| Acylating Agent | Amine | No. | Product | Yield (%) |
|---|---|---|---|---|
| tert-butyl oxalyl chloride | diphenylamine | 270 | | 22 |
| tert-butyl oxalyl chloride | indoline | 267 | | 21 |
| tert-butyl oxalyl chloride | methyl indoline-5-carboxylate | 269 | | 33 |
| N,N-dimethyl oxamoyl chloride | diethylamine | 261 | | 47 |
| N,N-dimethyl oxamoyl chloride | N-ethylaniline | 259 | | 28 |

TABLE 5-continued 1,2-Dicarbonyl analogues.

| Acylating Agent | Amine | No. | Product | Yield (%) |
|---|---|---|---|---|
| [dimethylamino-oxoacetyl chloride structure] | [N,N-diphenylamine structure] | 257 | [product structure] | 7 |
| [dimethylamino-oxoacetyl chloride structure] | [indoline structure] | 258 | [product structure] | 5 |

A number of 1,2-dicarbonyl compounds were tested and the results are shown in table 6. In general terms the 1,2-dicarbonyl substituted compounds gave similar absorbance maxima to the corresponding trifluoroacetyl analogues. Photostability followed a similar trend to that seen for the benzoyl analogues (albeit with higher values) with N-ethyl,N-phenyl derivative 248 showed good photostability with 78% remaining after irradiation. The highest photostability was seen for compounds derived from both N,N-diphenyl amine (237, 83% remains) and indoline (231, 80% remains). Broadly speaking this trend was continued with the other derivatives prepared. As also observed in the benzoyl series, the introduction of an ester moiety into the 5 position of the indoline ring, as in compound 256, resulted in a modest increase in photostability (85% from 80%), $\lambda_{max}$ and an increase in the efficiency of absorbance resulting in a compound with an E value of over 1200. An increase in steepness of the transmittance curve was also observed.

TABLE 6

Properties of select 1,2-dicarbonyl compounds and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 144 | [structure] | 271 | 319 | 350 | 23306 | 860 | 361 | 23 | 97 |

TABLE 6-continued

Properties of select 1,2-dicarbonyl compounds and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|-----|-----------|-----|------|------|------|------|------|------|------|
| 260 | 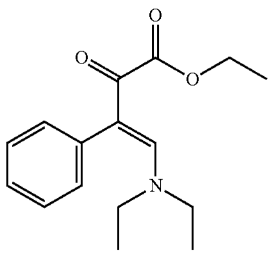 [SMILES: CCOC(=O)C(=O)/C(=C/N(CC)CC)c1ccccc1] | 275 | 313 | 352 | 19983 | 726 | 363 | 38 | 40 |
| 261 | 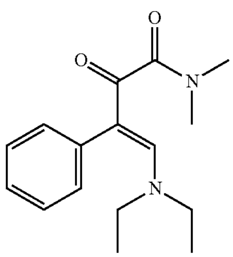 [SMILES: CCN(/C=C(/C(=O)C(=O)N(C)C)c1ccccc1)CC] | 274 | 310 | 342 | 23144 | 844 | 355 | 28 | 63 |
| 142 | 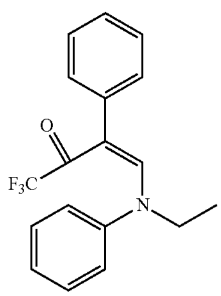 [SMILES: CCN(/C=C(\C(=O)C(F)(F)F)c1ccccc1)c1ccccc1] | 318 | 331 | 365 | 34708 | 1088 | 381 | 29 | 99 |
| 248 | 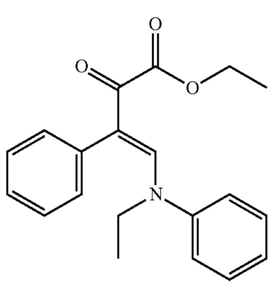 [SMILES: CCOC(=O)C(=O)/C(=C/N(CC)c1ccccc1)c1ccccc1] | 323 | 329 | 368 | 23523 | 728 | 383 | 38 | 78 |
| 271 | 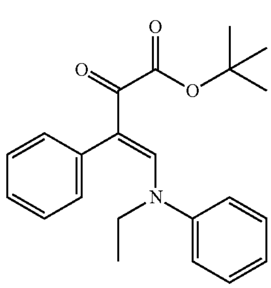 [SMILES: CCN(/C=C(/C(=O)C(=O)OC(C)(C)C)c1ccccc1)c1ccccc1] | 351 | 332 | 366 | 18592 | 530 | 381 | 36 | 75 |

TABLE 6-continued

Properties of select 1,2-dicarbonyl compounds and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 259 | 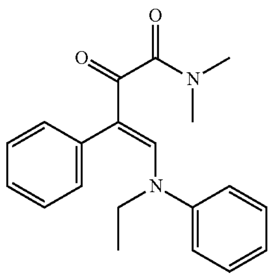 [SMILES: CCN(/C=C(/C(=O)C(=O)N(C)C)c1ccccc1)c1ccccc1] | 322 | 326 | 365 | 23336 | 724 | 378 | 34 | 66 |
| 143 | 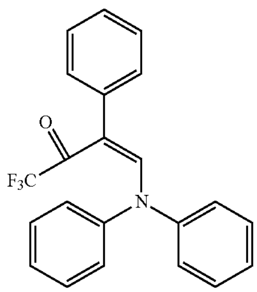 [SMILES: O=C(/C(=C\N(c1ccccc1)c1ccccc1)c1ccccc1)C(F)(F)F] | 367 | 351 | 381 | 27893 | 760 | 402 | 32 | Not soluble Assumed >98% |
| 237 | 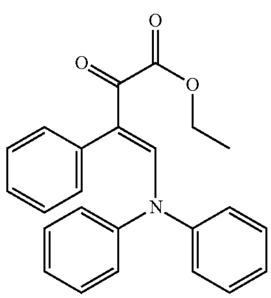 [SMILES: CCOC(=O)C(=O)/C(=C/N(c1ccccc1)c1ccccc1)c1ccccc1] | 371 | 348 | 380 | 28737 | 775 | 400 | 39 | 83 |
| 270 | 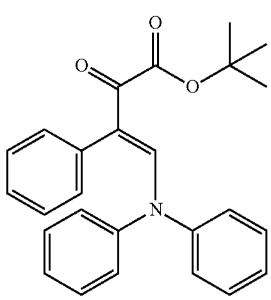 [SMILES: CC(C)(C)OC(=O)C(=O)/C(=C/N(c1ccccc1)c1ccccc1)c1ccccc1] | 399 | 349 | 381 | 22023 | 551 | 400 | 35 | 89 |
| 257 | 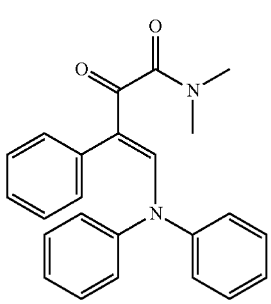 [SMILES: CN(C)C(=O)C(=O)/C(=C/N(c1ccccc1)c1ccccc1)c1ccccc1] | 370 | 346 | 378 | 14163 | 382 | 394 | 32 | 85 |

TABLE 6-continued

Properties of select 1,2-dicarbonyl compounds and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 164 | 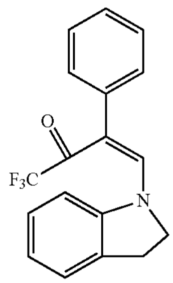 | 317 | 367 | 389 | 35741 | 1127 | 418 | 20 | 99 |
| 231 | 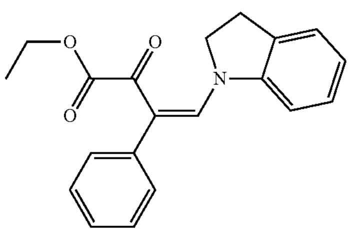 [SMILES: CCOC(=O)C(=O)/C(=C\N1CCc2ccccc21)c1ccccc1] | 321 | 363 | 388 | 31758 | 989 | 418 | 34 | 80 |
| 267 | 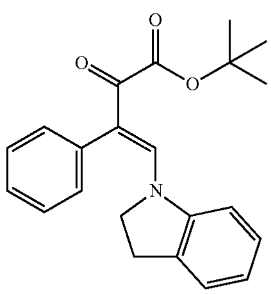 [SMILES: CC(C)(C)OC(=O)C(=O)/C(=C/N1CCc2ccccc21)c1ccccc1] | 349 | 366 | 389 | 32824 | 940 | 417 | 32 | 76 |
| 258 | 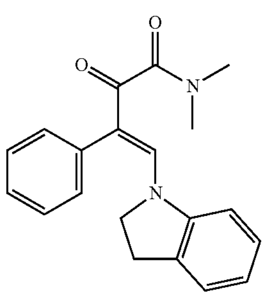 [SMILES: CN(C)C(=O)C(=O)/C(=C/N1CCc2ccccc21)c1ccccc1] | 320 | 359 | 384 | 33443 | 1045 | 409 | 23 | 63 |
| 201 | 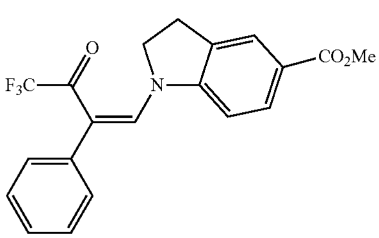 [SMILES: COC(=O)c1ccc2c(c1)CCN2/C=C(\C(=O)C(F)(F)F)c1ccccc1] | 375 | 373 | 391 | 46134 | 1230 | 420 | 18 | 97 |

TABLE 6-continued

Properties of select 1,2-dicarbonyl compounds and comparators.

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 256 | 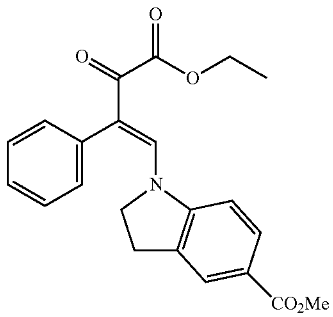 [SMILES: CCOC(=O)C(=O)/C(=C/N1CCc2cc(C(=O)OC)ccc21)c1ccccc1] | 379 | 372 | 391 | 48566 | 1228 | 421 | 28 | 85 |
| 269 | 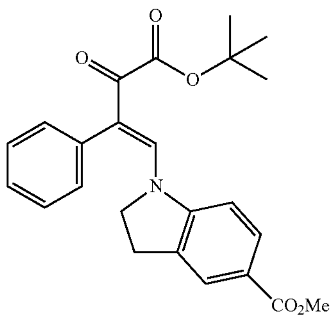 [SMILES: COC(=O)c1ccc2c(c1)CCN2/C=C(/C(=O)C(=O)OC(C)(C)C)c1ccccc1] | 407 | 374 | 391 | 42074 | 1033 | 419 | 26 | 94[a] |

Table 7, below, shows data for further 1,2-dicarbonyl compounds and further physical data for some of those exemplified in table 6. Compounds 277 and 278 were synthesised largely to investigate the effect of the ester/amide moiety on properties of the 1,2-dicarbonyl compounds. On moving from the ester to the amide a slight increase in steepness of transmittance curve was observed along with a lowering of λmax of approximately 5 nm. Photostability results for 277 gave a result of 95% stability. This confirms that the modifications to the amide moiety can be used to positively alter photostability. Compound 278 is an ester-bearing compound prepared from 2-ethylhexanol.

Whilst this compound does not feature a 3O alcohol as compound 269 does, it was postulated that the bulky alcohol side chain might also increase photostability. As has been observed previously, changing the ester does not impact the position of absorbance or the molar extinction coefficient greatly. 278 has a lower efficiency of absorbance (E) due to the increased molecular mass. The photostability of absorber 278 was measured as 88% which is intermediate between the corresponding ethyl ester (256, 85%) and the t-butyl ester (269, 94% average) but all representing useful levels of photostability.

TABLE 7

Physical and spectroscopic data for select compounds.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 231 | 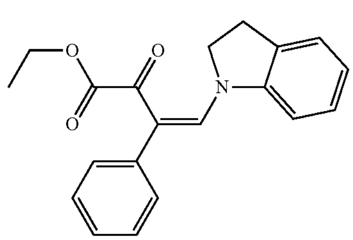 [SMILES: CCOC(=O)C(=O)/C(=C\N1CCc2ccccc21)c1ccccc1] | 321 | 4.6 | 363 | 388 | 31758 | 989 | >95 | Breakthrough 418 Steepness 34 Photostability 80% |

TABLE 7-continued

Physical and spectroscopic data for select compounds.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 258 | 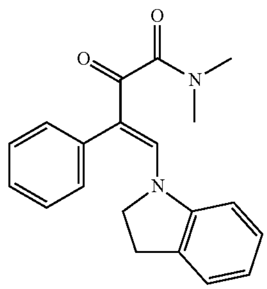 [SMILES: CN(C)C(=O)C(=O)/C(=C/N1CCc2ccccc21)c1ccccc1] | 320 | 3.2 | 359 | 384 | 33443 | 1045 | >95 | Breakthrough 409<br>Steepness 23<br>Photostability 63% |
| 256 | 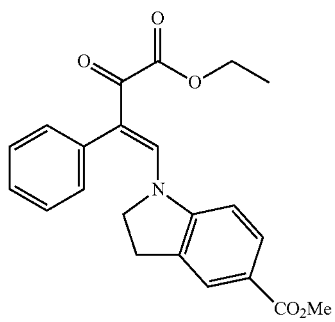 [SMILES: CCOC(=O)C(=O)/C(=C/N1CCc2cc(C(=O)OC)ccc21)c1ccccc1] | 379 | 4.8 | 372 | 391 | 46566 | 1228 | >95 | Breakthrough 421<br>Steepness 28<br>Photostability 85% |
| 277 | 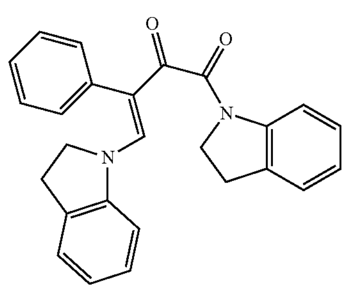 [SMILES: O=C(C(=O)N1CCc2ccccc21)/C(=C/N1CCc2ccccc21)c1ccccc1] | 394 | 5.2 | 365 | 388 | 34350 | 872 | >95 | Breakthrough 414<br>Steepness 26<br>Photostability 95% |
| 269 | 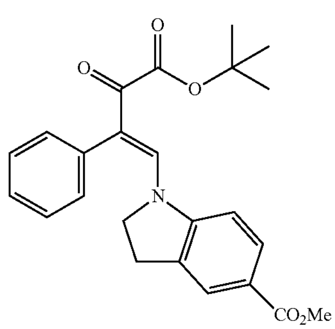 [SMILES: COC(=O)c1ccc2c(c1)CCN2/C=C(/C(=O)C(=O)OC(C)(C)C)c1ccccc1] | 407 | 5.5 | 374 | 391 | 42074 | 1033 | >95 | Breakthrough 419<br>Steepness 26<br>Photostability 94, 98, 91% |

TABLE 7-continued

Physical and spectroscopic data for select compounds.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 278 | 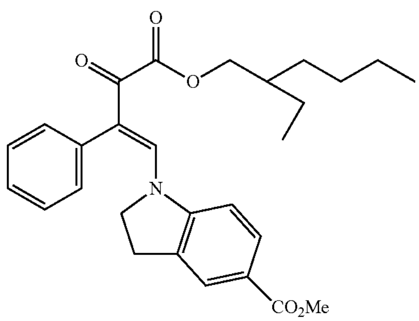 [SMILES: CCCCC(CC)COC(=O)C(=O)/C(=C/N1CCc2cc(C(=O)OC)ccc21)c1ccccc1] | 463 | 7.9 | 372 | 391 | 44118 | 953 | >95 | Breakthrough 418 Steepness 30 Photostability 88% |
| 288 | 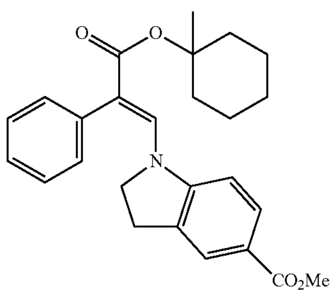 [SMILES: COC(=O)c1ccc2c(c1)CCN2/C=C(/C(=O)OC1(C)CCCCC1)c1ccccc1] | 419 | 7.3 | 356 | 370 | 57009 | 1360 | >95 | Breakthrough 383 Steepness 28 |
| 289 | 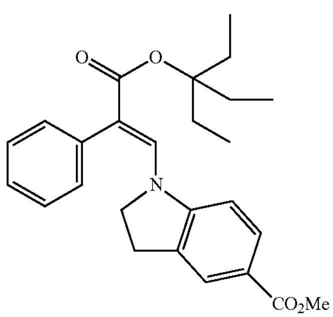 [SMILES: CCC(CC)(CC)OC(=O)/C(=C/N1CCc2cc(C(=O)OC)ccc21)c1ccccc1] | 421 | 7.6 | 357 | 370 | 59157 | 1405 | >95 | Breakthrough 381 Steepness 18 Photostability 78% |
| 290 | 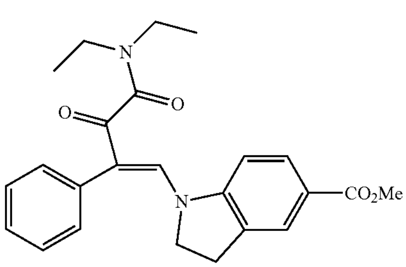 [SMILES: CCN(CC)C(=O)C(=O)/C(=C/N1CCc2cc(C(=O)OC)ccc21)c1ccccc1] | 406 | 4.6 | 370 | 389 | 51191 | 1260 | >95 | Breakthrough 412 Steepness 22 Photostability 53% |

TABLE 7-continued

Physical and spectroscopic data for select compounds.

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 305 | 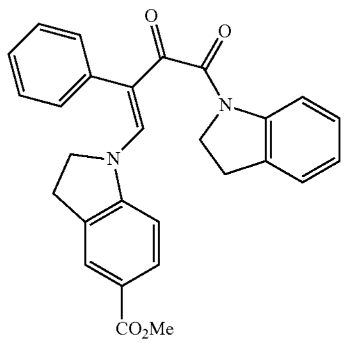 [SMILES: COC(=O)c1ccc2c(c1)CCN2/C=C(/C(=O)C(=O)N1CCc2ccccc21)c1ccccc1] | 452 | 5.5 | 375 | 391 | 48709 | 1078 | >95 | Breakthrough 417<br>Steepness 23<br>Photostability 80, 75 |

All compounds were found to be soluble in most organic solvents.

General Compound Synthesis Pathways

Scheme 13, below, shows a number of synthetic pathways resulting in compounds of the first aspect of a range of different classes. This scheme shows that, using the approaches set out herein and those known in the art, a very wide array of enamine compounds are attainable. Scheme 13 is indicative only and is not in any way limiting on the classes of compounds which can be synthesised.

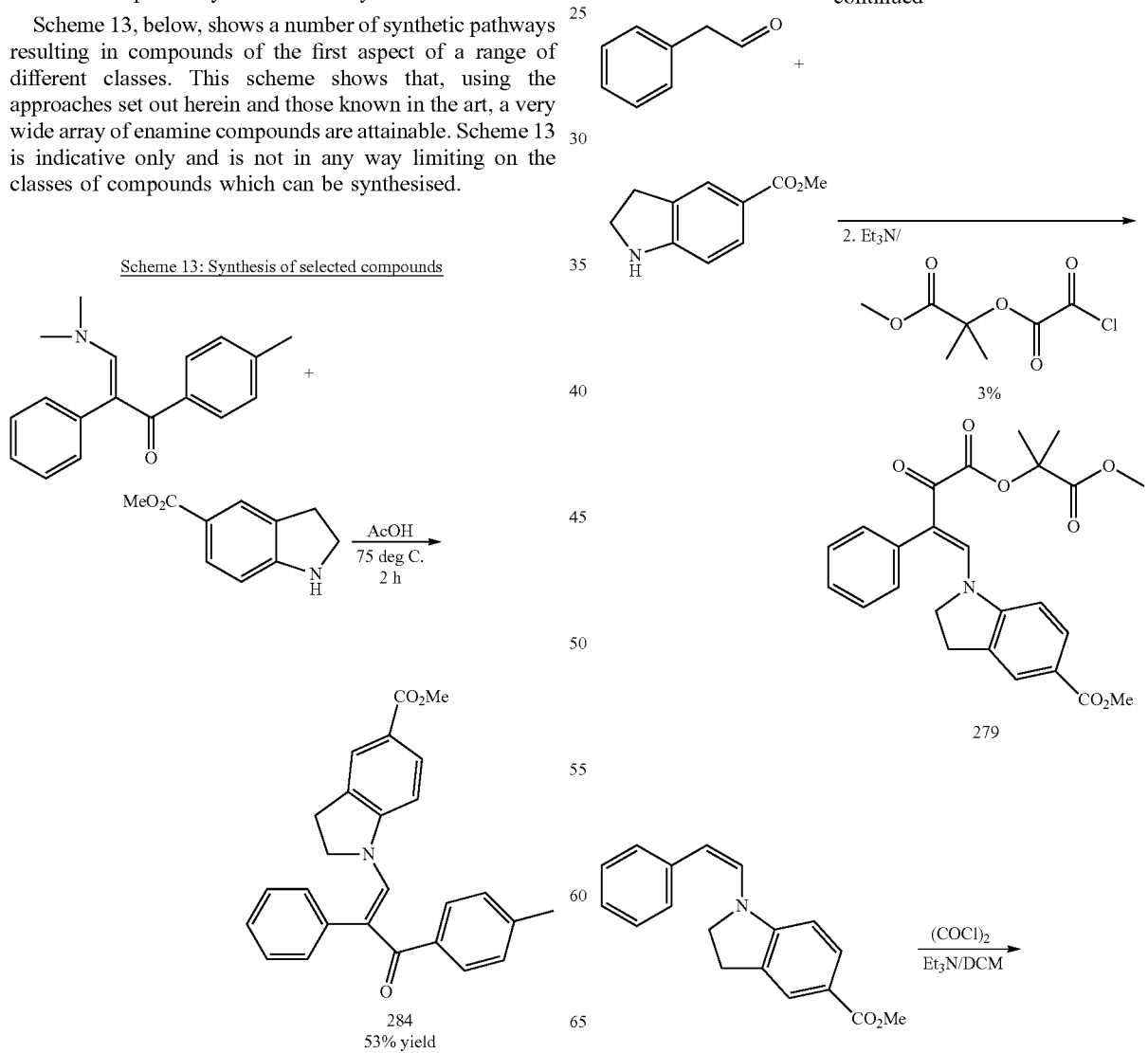

Scheme 13: Synthesis of selected compounds

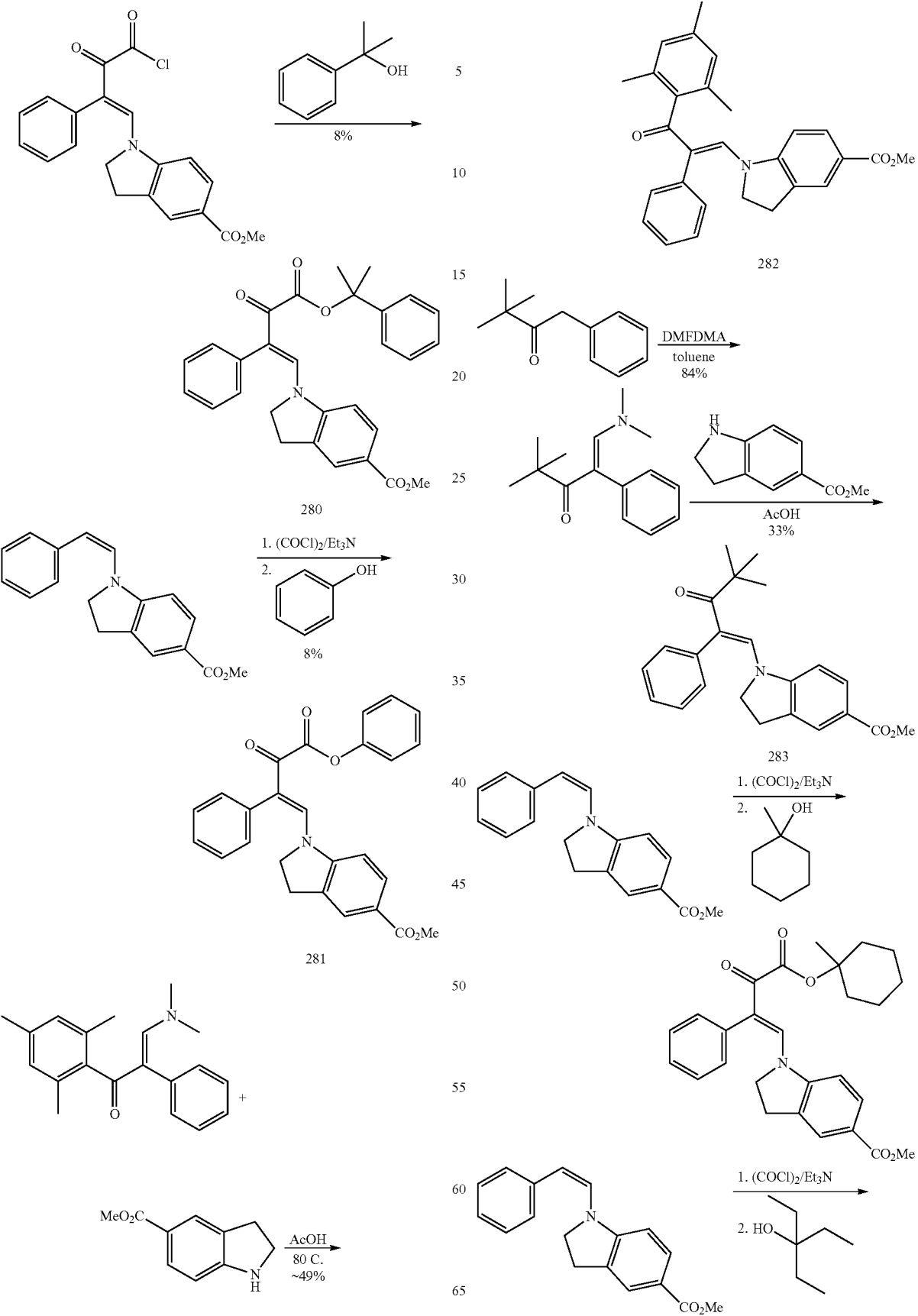

131
-continued

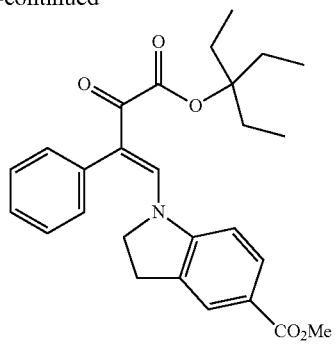

132
-continued

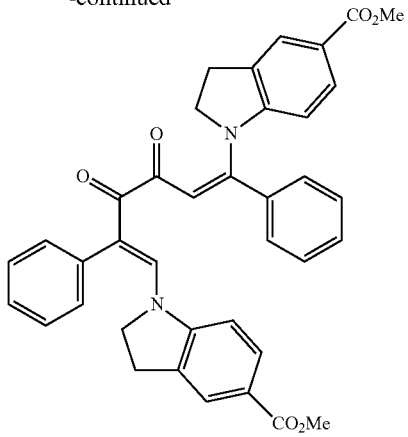

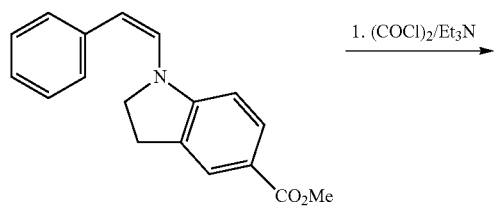

1. (COCl)$_2$/Et$_3$N →

Amongst the compounds synthesised using certain of the pathways of scheme 13 were some further examples of 1,2-dicarbonyl esters which were functionalised with 3° alcohols, in addition to a compound functionalised by phenol. Ester functionalised compound 279 proved to possess a very strong absorbance as did benzyl ester 280 which also featured a steep transmittance curve resulting in a critical wavelength of 370 nm and no residual colour. Substitution with a phenol, 281 resulted in weaker absorbance strength but with all compounds demonstrating strong photostability.

TABLE 8

Physical and spectroscopic data for select compounds

| No. | Structure | Mw | ClogP | $\lambda_{max}$ nm | $\lambda_{crit}$ nm | ε | E (1%, 1 cm) | Purity (%) | Other |
|---|---|---|---|---|---|---|---|---|---|
| 256 | 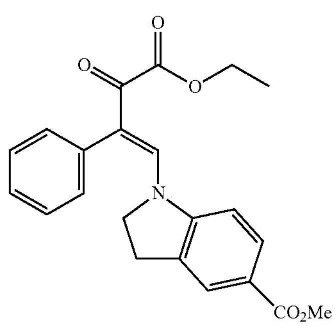 [SMILES: CCOC(=O)C(=O)/C(=C/N1CCc2cc(C(=O)OC)ccc21)c1ccccc1] | 379 | 4.8 | 372 | 391 | 46566 | 1228 | >95 | Photostability 85% Breakthrough 421 Steepness 28 |
| 269 | 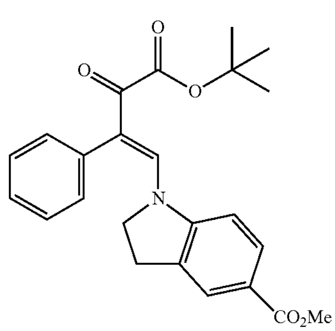 [SMILES: COC(=O)c1ccc2c(c1)CCN2/C=C(/C(=O)C(=O)OC(C)(C)C)c1ccccc1] | 407 | 5.5 | 374 | 391 | 42074 | 1033 | >95 | Photostability 94, 98, 91% Breakthrough 419 Steepness 26 |

TABLE 8-continued

Physical and spectroscopic data for select compounds

| No. | Structure | Mw | ClogP | $\lambda_{max}$ nm | $\lambda_{crit}$ nm | $\varepsilon$ | E (1%, 1 cm) | Purity (%) | Other |
|---|---|---|---|---|---|---|---|---|---|
| 279 | 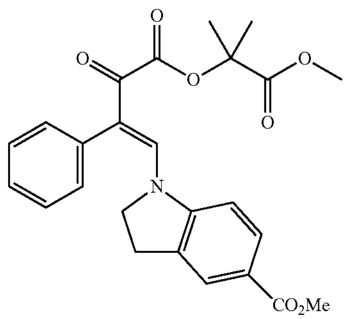 [SMILES: COC(=O)c1ccc2c(c1)CCN2/C=C(/C(=O)C(=O)OC(C)(C)C(=O)OC)c1ccccc1] | 451 | 4.8 | 368 | 386 | 58842 | 1304 | >95 | Photostability 32% Breakthrough 412 Steepness 32 |
| 280 | 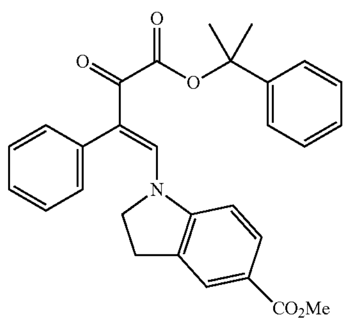 [SMILES: COC(=O)c1ccc2c(c1)CCN2/C=C(/C(=O)C(=O)OC(C)(C)c1ccccc1)c1ccccc1] | 469 | 7.1 | 357 | 370 | 67567 | 1440 | >95 | Photostability 68% Breakthrough 384 Steepness 21 |
| 281 | 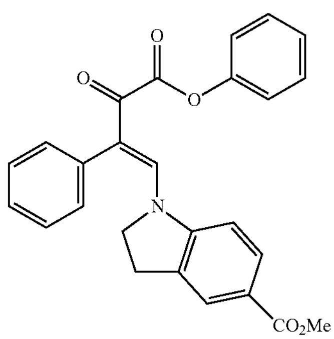 [SMILES: COC(=O)c1ccc2c(c1)CCN2/C=C(/C(=O)C(=O)Oc1ccccc1)c1ccccc1] | 427 | 5.1 | 376 | 392 | 30040 | 703 | >95 | Breakthrough 419 Steepness 34 |

All compounds were found to be soluble in most organic solvents.

Miscellaneous Compounds

A number of other compounds of the first aspect were synthesised with non-benzoyl or dicarbonyl functional groups. The synthesis of compound 249 having an electron withdrawing cyanoacteyl group is shown in scheme 14. Compound 238 was prepared in a similar manner.

Scheme 14: Synthesis of cyanoacetyl-bearing compound 249.

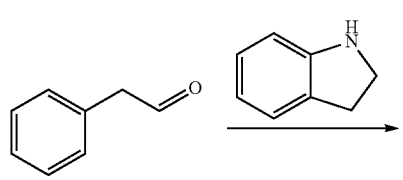

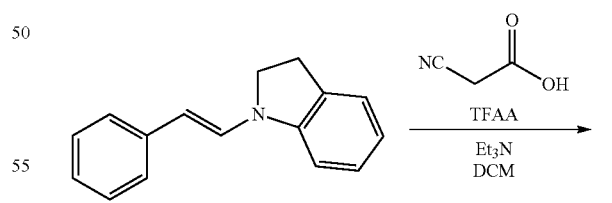

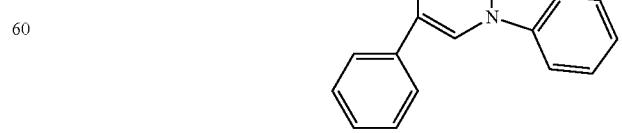

249

The properties of these compounds are shown in table 9 with comparator compounds. Both cyanoacetyl derivatives displayed a slightly lower value for $\lambda_{max}$ and $\lambda_{crit}$ with similar values for strength of absorbance compared to their trifluoroacetyl analogues. In both cases low solubility meant that photostability could not be measured. This would not preclude use of the compounds in many applications where solubility is not at issue.

example replacement of one reagent with an analogous reagent which presents a variation in side chains, will be apparent to access further compounds of the first aspect.

According to a second aspect of the present invention there is provided a composition comprising a compound of any one of formula I to VI, or a salt or isomer thereof, and a suitable carrier.

TABLE 9

Properties of miscellaneously functionalised compounds and comparators.

| No. | Structure | Mw | $\lambda_{max}$ (nm) | $\lambda_{crit}$ (nm) | ε | E (1%, 1 cm) | Break-through (1% T at 0.1%) | Steepness (nm) | Photo-stability (%) |
| --- | --- | --- | --- | --- | --- | --- | --- | --- | --- |
| 143 | 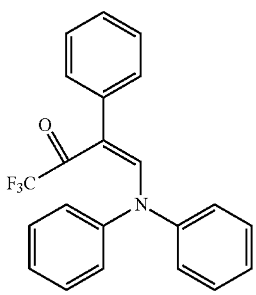 [SMILES: O=C(/C(=C\N(c1ccccc1)c1ccccc1)c1ccccc1)C(F)(F)F] | 367 | 351 | 381 | 27893 | 760 | 402 | 32 | Not soluble Assumed >98 |
| 236 | 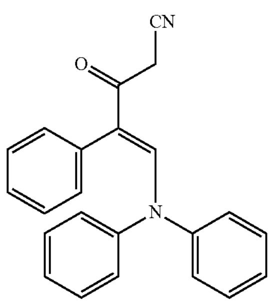 [SMILES: N#CCC(=O)/C(=C/N(c1ccccc1)c1ccccc1)c1ccccc1] | 338 | 346 | 373 | 28026 | 829 | 391 | 31 | Not soluble |
| 164 | 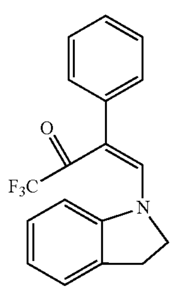 [SMILES: O=C(/C(=C\N1CCc2ccccc21)c1ccccc1)C(F)(F)F] | 317 | 367 | 389 | 35741 | 1127 | 418 | 20 | 99 |
| 249 | 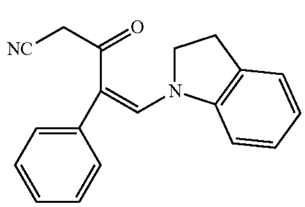 [SMILES: N#CCC(=O)/C(=C\N1CCc2ccccc21)c1ccccc1] | 288 | 361 | 361 | 31385 | 1089 | 405 | Not soluble | Not soluble |

It will be appreciated that the schemes above and discussion of synthesis in the examples, represent reaction pathways to access a range of compound classes of the first aspect. It will further be appreciate by the person of skill in the art that these reaction schemes are representative only and simple modification of the exemplified pathways, for In one embodiment, the compounds may provide for improved solubility or stability in standard compositions, including sunscreen compositions. Such solubility may be measured by generating, for example, a 3% solution of the relevant compound in 2:1:1 EtOH:capric/caprylic triglyceride:C12-C15 alkyl benzoate.

In one embodiment, the composition is a sunscreen composition. The sunscreen composition may be suitable for protection from one or more of UV-A, UV-B and visible light.

The composition may contain dispersing agents, emulsifiers or thickening agents to assist in applying a uniform layer of the active compounds. Suitable dispersing agents for the formulations include those useful for dispersing organic UV and visible light absorbing agents in a water phase, oil phase, or part of an emulsion, including, for example, chitosan.

Emulsifiers may be used in the composition to disperse one or more of the compounds or other components of the composition. Suitable emulsifiers include conventional agents such as, for example, ethoxylated alcohols (oleth-2, oleth-20 etc.), glycerol stearate, stearyl alcohol, cetyl alcohol, dimethicone copolyol phosphate, hexadecyl-D-glucoside, octadecyl-D-glucoside, cetearyl alcohol and dicetyl phosphate and ceteth-10-phosphate (Crodafos™ CES), one or more ethoxylated esters of natural derivatives, e.g. polyethoxylated esters of hydrogenated castor oil; or a silicone emulsifier such as silicone polyol; a free or ethoxylated fatty acid soap; an ethoxylated fatty alcohol; a free or ethoxylated sorbitan ester, an ethoxylated fatty acid; or an ethoxylated glyceride.

Emolients may be used in the sunscreen composition including cetyl esters, such as cetyl ethylhexanoate, isostearyl neopentanoate, diisopropyl sebacate, coconut oil and silicones.

Humectants may be used including glycols such as propylene glycol and butylene glycol as well as glycerine.

Rheology modifiers such as various Carbopol® acrylate polymeric compounds, alkyl acrylates as well as neutralisers and preservatives as are standard in the art.

Thickening agents may be used to increase the viscosity of the sunscreen composition. Suitable thickening agents include glyceryl stearate, carbomers, acrylate/acrylonitrile copolymers, xanthan gum and combinations of these. The amount of thickener within the sunscreen composition, on a solids basis without water, may range from about 0.001 to about 5%, preferably from 0.01 to about 1% and optimally from about 0.1 to about 0.5% by weight.

Minor optional adjunct ingredients for the sunscreen composition may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone (PVP), polyvinylpyrrolidone/vinylacetate, PVP/Eicosene copolymer and adipic acids/diethylene glycol/glycerine crosspolymer etc. Waterproofing agents may be present at levels of from about 0.01 to about 10% by weight.

There is considerable knowledge in the art in terms of sunscreen formulations and standard texts and journal articles may also provide guidance. One such text which may prove useful is *The Chemistry and Manufacture of Cosmetics*. An appropriate article to refer to may be Cosmetics & Toiletries, vol. 116, No. 9, September 2001 and Tanner. P. R., Dermatol. Clin. 2006 January; 24(1):53-62. These articles and textbook are incorporated herein in their entirety by way of reference.

Eusolex® UV-Pearls® (supplied commercially by Merck) may provide for the present absorbing compounds to be encapsulated in micro-capsules allowing for alternative options in formulation. Such encapsulation may provide for a reduced dermal uptake, lower allergy potential, and further improved photostability. The micro-encapsulation technology employed entraps the compounds in a sol-gel silica glass. Merck supplies such products as aqueous dispersions containing approximately 37% (w/w) of the UV absorber. The white liquids contain Eusolex® UV-Pearls® of about 1.0 μm diameter on average which are transparent when applied to the skin.

Therefore, in one embodiment, the compounds of the first aspect are present in a composition as encapsulated compounds. The encapsulation may be by any known method of encapsulation but preferably is by a sol gel encapsulation approach. Suitably, the encapsulation is a silica-based sol gel encapsulation. For compounds with highly desirable absorption properties but less than optimal photostability, encapsulation may improve the photostability into commercially acceptable territory.

The sunscreen compositions can additionally contain one or more further UV-protective substances, e.g. triazines, 1,3-diketones, such as avobenzone, oxanilides, triazoles or amides containing vinyl groups or cinnamides. Such protective substances are described, for example, in GB-A-2, 286,774 or alternatively are known from Cosmetics & Toiletries (107), 50 et seq. (1992).

The compositions may contain 0.1 to 15, preferably 0.5 to 10% by weight, based on the total weight of the composition, of a compound of any one of formula I to VI. The compositions can be prepared by physical mixing of the compounds with the auxiliary by the usual methods, such as, for example, by simply stirring the individual components together. The compositions can be formulated as a water-in-oil or oil-in-water emulsion, as an oil-in-alcohol lotion, as a vesicular dispersion of an ionic or non-ionic amphiphilic lipid, as a gel, solid stick or as an aerosol formulation. As a water-in-oil or oil-in-water emulsion, any compatible auxiliary preferably contains 5 to 50% of an oil phase, 5 to 20% of an emulsifier and 30 to 90% of water. The oil phase can in this case contain any oil suitable for cosmetic formulations, e.g. one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

In one embodiment, the sunscreen composition may comprise more than one compound of any one of formula I to VIII or a compound of any one of formula I to VIII and a known UV absorbing sunscreen agent or protective agent such as avobenzone, EHT, octinoxate and octocrylene.

The protective agent may be an additive, such as octocrylene and like compounds, which have protective effects on the compounds of the invention. While showing modest UV absorption itself, octocrylene is primarily used in sunscreen formulations due to the stabilising and protective effect it has on other UV absorbing actives. Current understanding suggests that the energy levels of such stabilisers need to be matched with the UV/light absorbing active to allow efficient stabilisation and so it cannot be assumed that protective agents such as octocrylene would work with any particular class of absorbing compounds. Due to the lack of understanding of the protective relationship, and hence lack of reliable prediction, it is necessary to test the compounds with the protective additive and see if the benefit is obtained. Advantageously, it has been found by such testing that the present compounds of formula Ia, Ib, II and/or V are appropriately 'matched' with octocrylene and so receive the additional protective benefit. Further protective agents which may be present in the composition include MBC, MBBT, BEMT, DHHB, Diethylhexyl 2,6 Naphthalate (DEHN, CORAPAN® TQ), Diethylhexyl Syringylidene Malonate (DESM, Oxynex® ST), and Benzotriazolyl Dodecyl p-cresol (TINOGARD® TL).

In one alternative embodiment, the composition comprising a compound of any one of formula I to VIII is a coating composition, a plastics composition or a paint composition.

UV protective paint or general coating compositions can be useful in external applications such as in automotive paints, masonry and timber paints and UV protective compositions for boats and other marine applications.

The paint composition may contain a diluent or solvent such as water, petroleum distillate, an esters, a glycol ether, a binder or film forming component including include synthetic or natural resins such as alkyds, acrylics, vinylacrylics, vinyl acetate/ethylene (VAE), polyurethanes, polyesters, melamine resins, epoxy, or oils, and may comprise a pigment or dye to provide colouration and/or other optional additives such as catalysts, thickeners, stabilizers, emulsifiers, texturizers, adhesion promoters, UV stabilizers, flatteners (de-glossing agents), fungicides, flow control agents, surfactants, and rheology modifiers.

In a further alternative embodiment, the composition may be a glass or plastic film-forming composition. Such compositions may be useful in forming UV and/or visible light protective glass or plastic films useful to prevent UV and/or visible light damage to the enclosed material. They may be useful in forming or coating: automotive glass, architectural glass and plastics, such as PVC, used in similar applications. The compositions may, in one embodiment, result in UV and/or visible light protective ophthalmic lenses including corrective contact lenses and eyeglasses. Such compositions are known in the art but have not comprised the compounds of the present invention to this point.

In further embodiments, the composition comprising at least one compound of any one of formula I to VI, or a salt thereof, may be an industrial formulation. Such formulations may form components of dishwashing liquids, gels or tablets, food packaging, coatings for signage and the like.

Such formulations may comprise a range of emulsifiers, silicates, bleaches, activators, catalysts, metal care agents, alkalinity agents, polymeric dispersants, anti-redisposition agents, sulfonated or carboxylated polymers, enzymes, ionic surfactants and non-ionic surfactants, as are known in the art.

Detergent active components which may be selected from bleach, bleach activator, bleach catalyst, surfactants, alkalinity sources, enzymes, polymeric dispersants, anti-corrosion agents (e.g. sodium silicate) and care agents. Highly preferred detergent components include a builder compound, an alkalinity source, an anti-redeposition agent, a sulfonated polymer, an enzyme and an additional bleaching agent.

The bleach is preferably selected from inorganic peroxides inclusive of perborates and percarbonates, organic peracids inclusive of preformed monoperoxy carboxylic acids, such as phthaloyl amido peroxy hexanoic acid and di-acyl peroxides Builders suitable for use in such an industrial detergent composition include builders which form water-soluble hardness ion complexes (sequestering builders) such as citrates and polyphosphates e.g. sodium tripolyphosphate and sodium tripolyphosphate hexahydrate, potassium tripolyphosphate and mixed sodium and potassium tripolyphosphate salts and builders which form hardness precipitates (precipitating builders) such as carbonates e.g. sodium carbonate.

Other suitable builders include amino acid based compounds or a succinate based compound. Examples of suitable amino acid based compounds include MGDA (methylglycine-diacetic acid), and salts and derivatives thereof and GLDA (glutamic-N,N-diacetic acid) and salts and derivatives thereof. GLDA (salts and derivatives thereof) is especially preferred according to the invention, with the tetrasodium salt thereof being especially preferred. Particular suitable builders include; for example, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)aspartic acid (SMAS), N-(2-sulfoethyl)aspartic acid (SEAS), N-(2-sulfornethyl)glutarnic acid (SMGL), N-(2-sulfoethyl)glutarnic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts or ammonium salts thereof The detergent and cleaning compositions herein can comprise traditional detergency components and can also comprise organic solvents having a cleaning function and organic solvents having a carrier or diluent function or some other specialised function. The compositions will generally be built and comprise one or more detergent active components which may be selected from bleaching agents, surfactants, alkalinity sources, enzymes, thickeners (in the case of liquid, paste, cream or gel compositions), anti-corrosion agents (e.g. sodium silicate) and disrupting and binding agents (in the case of powder, granules or tablets).

In yet a further embodiment, the composition may be a treatment for hair of a mammal, such as a human or companion animal. The hair care composition may be a colouring or other cosmetic composition or may be a UV protective composition specifically designed for hair application. The composition may directly protect the hair from UV damage or the compound(s) of the first aspect contained therein may also provide UV protection to dyes or other components of the hair treatment composition. Dyes and other components which may be included in the composition include anionic and/or cationic surfactants, fragrances, pest repellents, vitamins, sunscreens and cooling agents are well known in the art and it is envisaged that the composition would comprise one or more compounds of the first aspect along with one or more such components and a suitable carrier.

A third aspect of the present invention resides in the use of a compound of any one of formula I to VI, or a salt or isomer thereof, as an electromagnetic radiation absorbing compound.

A fourth aspect of the present invention resides in a method of protecting a surface or tissue from electromagnetic radiation including the step of applying a compound of any one of formula I to VI, or a salt or isomer thereof, to the surface or tissue.

Preferably, the use of the third aspect or the method of the fourth aspect has the compound as a component of a sunscreen composition. The compound of any one of formula I to VIII may be present in the sunscreen composition with a range of standard formulation agents including water, various emulsifiers, stabilisers and surfactants.

Alternatively, the use of the third aspect or the method of the fourth aspect has the compound as a component of a coating composition. The compound of any one of formula I to VIII may be present in the coating composition with a range of standard formulation agents including, one or more of the agents described above. The coating composition may be a medical device coating, hair care, paint, staining, UV and/or visible light protective, tinting, marine protection or polymeric matrix formulation wherein the compound of any one of formula I to VIII provides UV and/or visible light protective or additional UV and/or visible light protective properties to the formulation.

For example, the coating composition may be a paint formulation for the exterior of a building, marine vessel or for exposed timber structures. The coating composition may also be a matrix coating for signage and the like which are exposed to the suns rays for extended periods of time and which display information which it is desirable to protect from fading. It may be used for medical device coatings as described for the second aspect.

Further, the use of the third aspect or the method of the fourth aspect may employ the compound of any one of formula I to VIII as a component of a UV and/or visible light protective glass and/or UV and/or visible light protective polymeric film. The glass may be prepared in a manner standard in the industry. The polymeric film may be chosen from a range of standard film materials such as polyolefin-based films. The compounds of the present invention may be incorporated by cross-liking during film formation or may be associated with the film forming compounds, such as loosely held within the polymeric matrix.

In one embodiment, the use of the third aspect or the method of the fourth aspect may employ the compound of any one of formula I to VIII as a component of a packaging and/or photobleachable and/or light exposure indicating material. The compounds of the invention may have their colour altered by exposure to UV and/or visible light. They may change from colourless to exhibit a colour or vice versa.

In one embodiment, the use of the third aspect or the method of the fourth aspect may have the compound in or on an ophthalmic lens. This may be in terms of the UV and/or visible light absorbing compounds being cast in a lens formulation where the absorber is added to the bulk lens monomer prior to casting. Alternatively, the UV and/or visible light absorbing compound may be included as part of a coating layer or via imbibition. The lens may be a glass or plastic lens. By way of non-limiting example only, compounds 142, 143, 164 and 213 have been shown to be stable enough for such incorporation and to maintain useful levels of absorption thereafter.

Plastic lenses may be tinted by dipping them in a heated soluble dye comprising the UV and/or visible light absorbing compounds. This dye penetrates a uniform distance into the lens surfaces, providing a tint of uniform colour and transmittance and incorporating the UV and/or visible light absorbing compound. Glass lenses may be tinted by the addition of a chemical compound to the molten glass. The UV and/or visible light absorbing compound, if stable under those conditions, may be added in this process.

Some glass lenses are tinted by the application of a coating to one or both lens surfaces. These coatings consist of a thin layer of a coloured glass compound or a metal oxide that is applied using a vacuum deposition process. The UV and/or visible light absorbing compounds of the invention may be incorporated during this standard process.

In embodiments wherein the UV and/or visible light absorbing compound is included in the lens during formation of same it may be co-polymerised with a lens forming monomer. Many lens-forming monomers are known in the art and include both acrylic and silicone-containing monomers, among others. Non-limiting examples of preferred lens-forming monomers are diethyleneglycol bis allylcarbonate, 2-phenylethyl methacrylate; 4-phenylbutyl methacrylate; 5-phenylpentyl methacrylate; 2-benzyloxyethyl methacrylate; and 3-benzyloxypropyl methacrylate; and corresponding acrylates thereof.

The present compounds may also be used in the formation of plastic materials whereby their presence within the plastics matrix, either in the sense of being captured therein or being chemically bonded to the plastics backbone, imparts UV and/or visible light protective properties.

Therefore, it will be appreciated that the present compounds may be electromagnetic radiation absorbing molecules for human and material photo protection applications, including as components of coating compositions, glass compositions, plastics compositions, film-forming compositions, paint compositions; components of or coatings for lenses and eyeglasses; surface coatings for automobiles, timber, masonry, metals, plastics and glass; and components of compositions for marine applications.

In any embodiment of the compound of any one of formula I to VIII, or of the compound employed in any of the second, third or fourth aspects, independently, the compound is not a compound selected from the group consisting of:

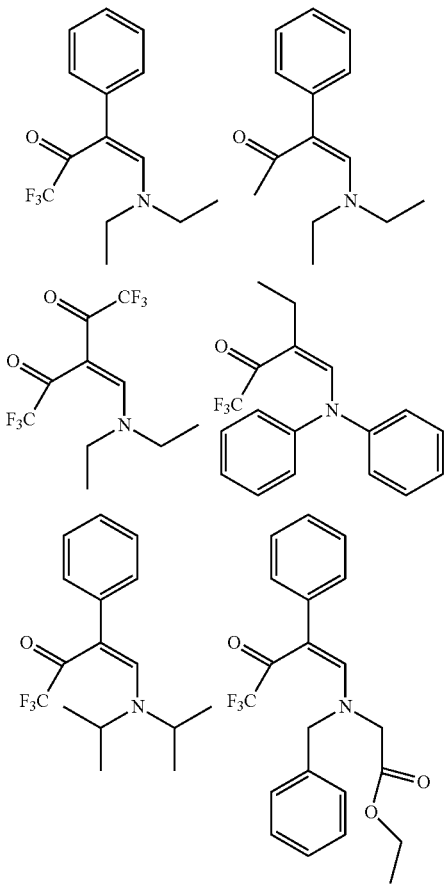

-continued

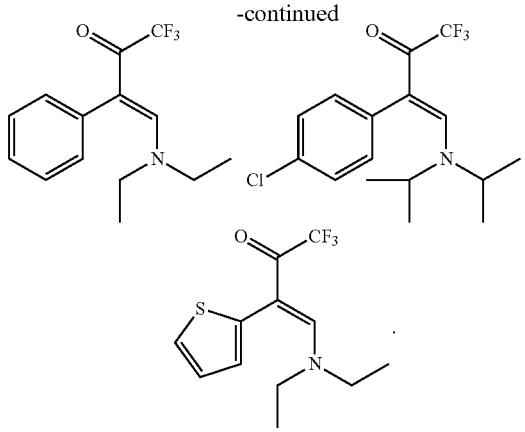

and

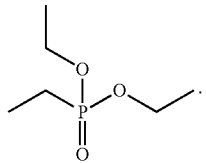

In any embodiment of the compound of any one of formula I to VIII, or of the compound employed in any of the second to sixth aspects, independently, any one or more of the following provisos may apply to the compound:

when $R_1$ is phenyl or chlorophenyl, $R_2$ is hydrogen and $R_5$ is $CF_3$ then $R_3$ and $R_4$ are (i) not both ethyl or isopropyl; and (ii) if one of $R_3$ or $R_4$ is benzyl then the other is not an ester group;

$R_1$ and $R_2$ do not form a ring structure;

$R_3$ or $R_4$ do not form a ring structure or fused ring structure with $R_1$ and/or $R_2$;

$R_3$ and $R_4$ do not form an aziridine ring with the nitrogen atom in formula I to VIII to which they are attached;

the alkene carbon atom of the enamine does not form a cyclic structure with the nitrogen atom of the enamine;

when $R_1$, $R_5$ and one of $R_3$ or $R_4$ is unsubstituted phenyl, and $R_2$ is hydrogen then the other of $R_3$ or $R_4$ is not methyl, unsubstituted phenyl or $CH_2CH_2NH-Ph$;

when $R_1$, $R_2$, $R_5$ and one of $R_3$ or $R_4$ is unsubstituted phenyl, then the other of $R_3$ or $R_4$ is not benzoyl;

when one of $R_3$ or $R_4$ is alkyl then the other cannot be hydrogen or methyl;

when $R_1$ is hydrogen then $R_5$ is not alkyl greater than $C_1$ to $C_6$;

when $R_1$ is pyridine then $R_3$ or $R_4$ are not methyl;

when $R_5$ is phenyl then it is not para-substituted with a nitro group;

when $R_5$ is methyl, $R_1$ is unsubstituted phenyl and one of $R_3$ or $R_4$ is unsubstituted phenyl, then the other of $R_3$ or $R_4$ is not methyl or unsubstituted phenyl;

when $R_5$ is

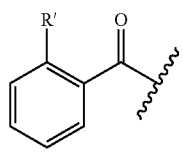

and R' is hydrogen or carboxyl then $R_3$ an $R_4$ are not unsubstituted phenyl and methyl, at the same time, and are not phenol and acetyl groups, at the same time, and are not both unsubstituted phenyl, and are not unsubstituted phenyl and unsubstituted benzyl, at the same time, and do not together form a methyl substituted indole or a benzimidazole; and $R_3$ and $R_4$ do not comprise In any embodiment of a compound of any one of formula I to VIII, $R_3$ and/or $R_4$ may not comprise a sulfonic acid group. A sulfonic acid group is any group having the formula —$SO_3X$ wherein X may be hydrogen, an ammonium ion or other salt or counterion.

In one particular embodiment of a compound of any one of formula I to VIII, wherein $R_3$ and/or $R_4$ together form a bicyclic or tricyclic group then the bicyclic or tricyclic group may not comprise a sulfonic acid group.

In a further particular embodiment of a compound of any one of formula I to VIII, wherein $R_3$ and/or $R_4$ together form an indole or indole-containing or a fused piperidine-phenyl group then the phenyl group of these structures may not comprise a sulfonic acid group.

In any embodiment of a compound of any one of formula I to VIII, $R_3$ and/or $R_4$ may not be methyl.

In any embodiment of a compound of any one of formula I to VIII, $R_3$ and/or $R_4$ may not be ethyl.

In any embodiment of a compound of any one of formula I to VIII, $R_1$ may not be acetyl.

In any embodiment of a compound of any one of formula I to VIII, $R_1$ may not be an ester/alkyl alkanoate group.

In any embodiment of a compound of any one of formula I to VIII, $R_1$ may not be cyano.

In any embodiment of a compound of any one of formula I to VIII, $R_5$ may not be $CCl_3$.

In any embodiment of a compound of any one of formula I to VIII, $R_5$ may not be halo-substituted phenyl.

In any embodiment of a compound of any one of formula I to VIII, $R_5$ does not comprise a double bond adjacent the carbonyl carbon to which $R_5$ is attached.

The invention will now be described by, but it is in no way limited to, the following Examples.

EXPERIMENTAL

Example 1—Select Procedures for Compound Preparation

A number of synthetic pathways have been shown in the schemes discussed earlier. Therefore, a detailed procedure is only provided for compounds 142 and 143. Characterisation data was obtained for all compounds but, similarly, is not included for the sake of brevity.

Method 1 Preparation of 4-(ethyl(phenyl)amino)-1, 1,1-trifluoro-3-phenylbut-3-en-2-one, 142

A solution of 2-phenylacetaldehyde (0.643 ml, 5.78 mmol) in $CHCl_3$ (Volume: 10 ml) was treated with 4 Å sieves (0.5 g, 4.13 mmol) and then N-ethylaniline (0.505 ml, 4.13 mmol) (amount adjusted to account for lack of purity in phenylacetaldehyde). After stirring at room temperature (RT) for 2 h analysis of an aliquot shows mostly product with only small amounts of starting aniline and aldehyde. A portion of this mixture of N-ethyl-N-styrylaniline in $CHCl_3$ containing 20% N-ethylaniline and 10% 2-phenylacetaldehyde (0.45 g, 2.015 mmol) was treated with triethylamine (0.562 ml, 4.03 mmol) and then dropwise with TFAA (0.313 ml, 2.217 mmol) and left to stir at RT overnight. NMR of an aliquot suggests only traces of enamine remain. The mixture was diluted with water/DCM, shaken and the organic phase separated and washed with $NaHCO_3$ before drying ($MgSO_4$) and evaporation to an orange sweet smelling oil (710 mg). The crude material was purified by column chromatography eluting with 0-5% EtOAc/petroleum ether to give 142 as a pale yellow oil which on standing solidified to an off white solid (362 mg, 56%).

$\delta_H$ ($CDCl_3$, 400 MHz) 7.95 (s, 1H), 7.24-6.95 (m, br, 10H), 3.51-3.46 (m, br, 2H), 0.98-0.94 (m, br, 3H). $\delta_C$ ($CDCl_3$, 100 MHz) 150.6, 131.2, 128.9, 127.5, 127.0, 126.2, 13.3. HRMS (EI): calc. for $C_{18}H_{16}NOF_3[M^+]$, 319.1179. Found, 319.1178 $[M^+]$. UV $\lambda_{max}$ 331 nm, $\varepsilon$ 34708 $M^{-1}$ $cm^{-1}$.

Preparation of 4-(diphenylamino)-1,1,1-trifluoro-3-phenylbut-3-en-2-one, 143

Prepared according to the procedure above for the preparation of 4-(ethyl(phenyl)amino)-1,1,1-trifluoro-3-phenylbut-3-en-2-one, 142 as a pale yellow solid in 43% yield.

$\delta_H$ ($CDCl_3$, 400 MHz) 8.12 (s, 1H), 7.17-7.05 (m, br, 6H), 6.92-6.87 (m, br, 7H), 6.80-6.77 (m, 2H). $\delta_C$ ($CDCl_3$, 100 MHz) 180.0 (m), 148.8, 132.5, 131.2, 129.3, 127.6, 127.0, 126.6, 115.1. HRMS (EI): calc. for $C_{22}H_{16}NOF_3[M^+]$, 367.1179. Found, 367.1180 $[M^+]$. UV $\lambda_{max}$ 351 nm, $\varepsilon$ 27893 $M^{-1}$ $cm^{-1}$.

Figure 2:
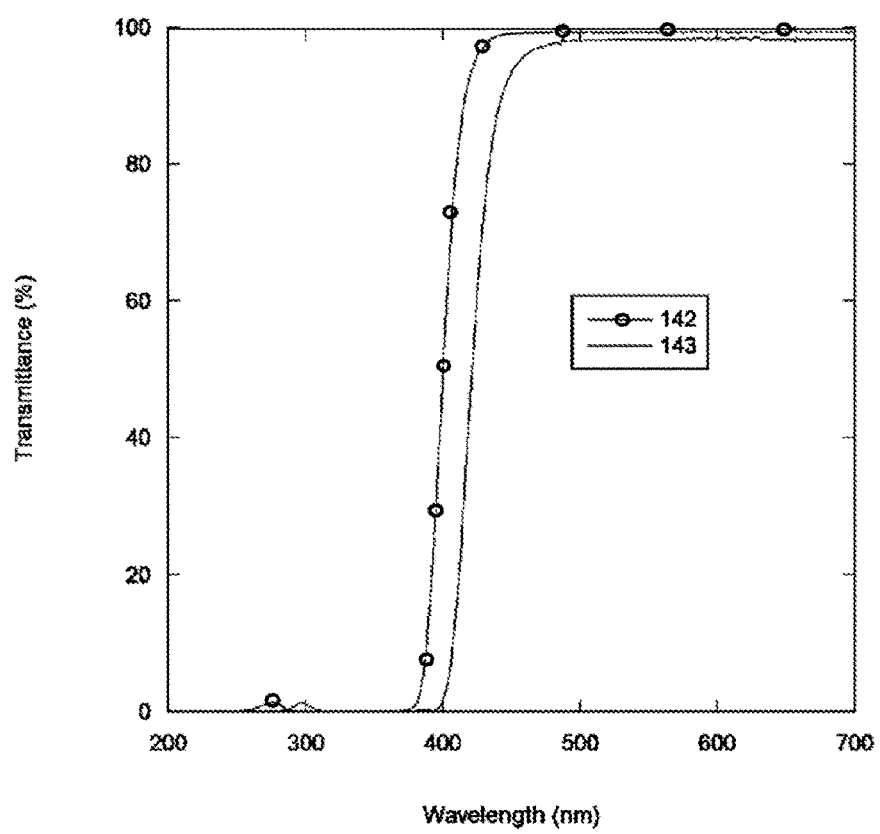
FIG. 2 is a is a graphical representation of the % transmission of compounds 142 and 143 measured in a 2 mm cuvette as 0.1% solutions in methanol (142 is the left most trace)

The following, table 11, provides information on the absorption profile of compounds 142 and 143.

influence of the second aryl ring, giving significant absorbance in the visible region. While the strength of the absorbance was lower than that observed for 142, presumably as a result of the difficulty in obtaining co-planarity of the chromophore with the added steric bulk of a second aromatic substituent, it should be noted that this may not be an issue for use of diaryl absorbers such as 143 due to the low cost of their preparation. Prototype absorber 142 also proved to be exceptionally photostable with 99% of the material remaining after irradiation for 1 hour. The absorbance and transmission properties of 142 and 143 are also seen in FIGS. 1 and 2, respectively.

Example 2—General Procedures for Lens Casting

Two lens formulations were used. The first (CR-39) was composed of Di(ethylene glycol) bis(allylcarbonate) with 3% wt benzoyl peroxide as initiator. The second lens formulation (NK) was made up of 4 parts NK Ester BPE 100N (Ethoxylated Bisphenol A dimethacrylate) to 1 part NK Ester 9G (PEG 400 dimethacrylate) with 0.4 wt % AIBN as initiator.

A Viton O-ring (RS part no 129-088, 13.94 mm id, 2.62 mm thickness; initial tests suggest an inexpensive nitrile rubber alternative, RS part no 128-912 would also work satisfactorily) was attached to a standard glass microscope slide using a minimal amount of superglue. Once the glue had dried the lens matrix (3 g of the lens matrix was treated with 3 mg of absorber, 0.1 wt % and stirred until dissolution complete. 3 g of the matrix was sufficient to prepare 3-4 lenses) was added via pipette to the interior until a convex meniscus was formed at the top of the O-ring. The mixture

TABLE 11

Data for compounds 142 and 143.

| No. | Structure | Mw | ClogP | $\lambda_{max}$ (nm) | $\lambda_{crit}$ (nm) | $\varepsilon$ | E (1%, 1 cm) | Photo-stability (% remains) |
|---|---|---|---|---|---|---|---|---|
| 142 | 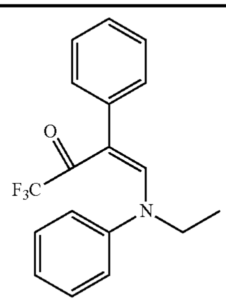 | 319 | 5.1 | 331 | 365 | 34708 | 1088 | 91 |
| 143 | 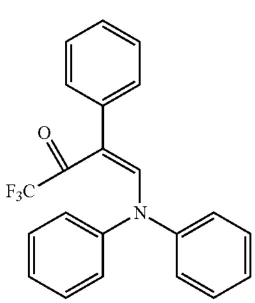 [SMILES: O=C(/C(=C\N(c1ccccc1)c1ccccc1)c1ccccc1)C(F)(F)F] | 367 | 5.9 | 351 | 381 | 27893 | 760 | N/A |

Compound 142 proved to possess strong UV absorbance with a $\lambda_{max}$ of 331 nm and a $\lambda_{crit}$ of 365 nm. As expected the $\lambda_{max}$ and $\lambda_{crit}$ of 143 were higher, likely as a result of the was then left to settle for 15 minutes during which time any bubbles formed were dispersed. A second microscope slide was then slowly rolled on top of the first to form a seal and expel any air. Taking care to maintain pressure the lens mould was then clamped at the sides with two "Bulldog" clips and cured in an oven at 70° C. for 18 hours. Once the curing process was complete the two microscope slides were separated and the lens removed from the O-ring before washing with acetone and drying/polishing with a soft tissue. The lenses thus formed were approximately 2 mm thick and 15 mm in diameter.

Figure 3:
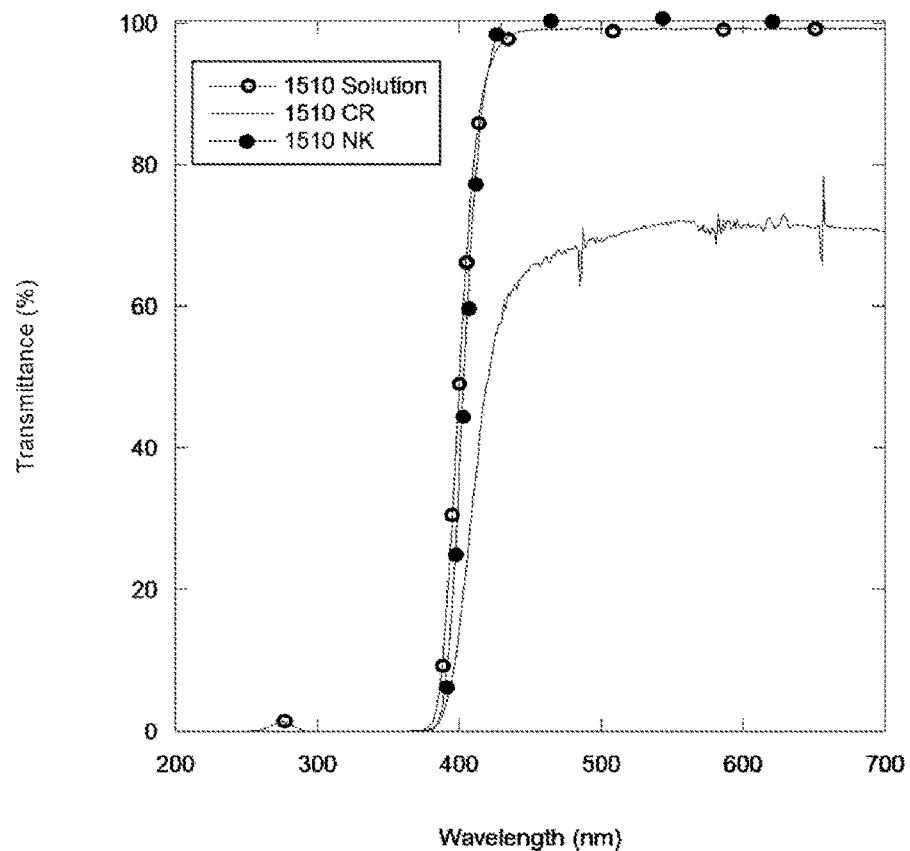
FIG. 3 is a graphical representation of the % transmission of compound 142 in differing lens compositions measured as a 2 mm thickness lens of 0.1% concentration. Solution denotes the absorber as a methanol solution, CR-39 the absorber in a cured CR-39 lens and NK the absorber in a cured NK ester lens formulation (1510 Solution and 1510 NK are left most traces which largely overlap until the 1510 NK trace continues off the chart while the 1510 Solution one plateaus and the 1510 CR trace is the right most trace which plateaus at the lowest transmittance)
Figure 4:
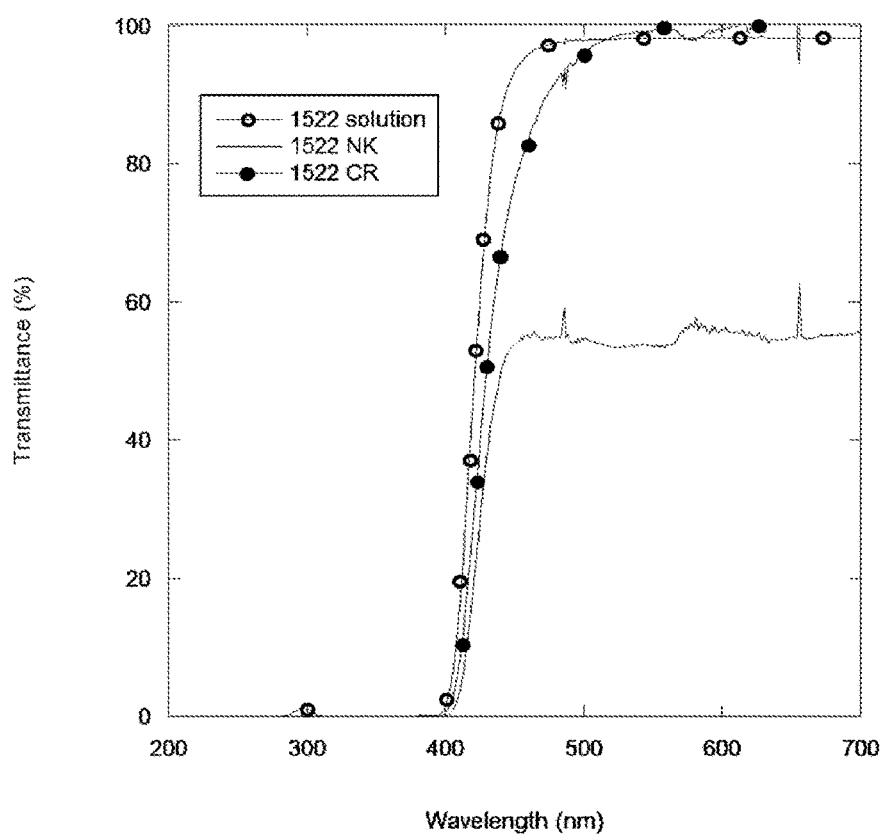
FIG. 4 is a graphical representation of the % transmission of compound 143 in differing lens compositions measured as a 2 mm thickness lens of 0.1% concentration. Solution denotes the compound as a methanol solution, CR-39 the compound in a cured CR-39 lens and NK the compound in a cured NK ester lens formulation (the 1522 NK trace plateaus at the lowest transmittance at 500 nm while the 1522 solution trace is the left most)

Both compound 142 and 143 are seen to be stable to lens casting conditions with seemingly very little if any decomposition on casting in lenses both in CR-39 (initiated with benzoyl peroxide) and NK-Ester (initiated by AIBN) and, importantly, no observable colouration of the test lenses. The transmittance spectra of the lenses obtained for both media in contrast with the simple solutions can be seen in FIG. 3 (compound 142) and 4 (compound 143).

A range of further fluorinated compounds were synthesised, in the manner used for compounds 142 and 143, and tested and their structures and properties are set out in table 12. Compounds 142 and 143 are included for comparison's sake.

TABLE 12

Data for selected compounds of the first aspect. (N/A means compound not tested)

| Structure | No. | $\lambda_{max}$ (nm) | $\lambda_{crit}$ (nm) | ε | E (1%, 1 cm) | Photo-stability (% remains) |
|---|---|---|---|---|---|---|
| 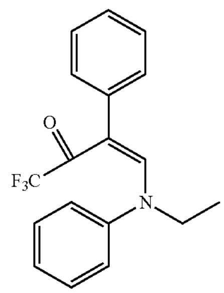 [SMILES: CCN(/C=C(\C(=O)C(F)(F)F)c1ccccc1)c1ccccc1] | 142 | 331 | 365 | 34708 | 1088 | 99 |
| 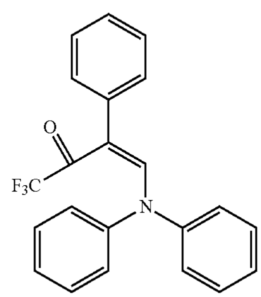 [SMILES: O=C(/C(=C\N(c1ccccc1)c1ccccc1)c1ccccc1)C(F)(F)F] | 143 | 351 | 381 | 27893 | 760 | N/A |
| 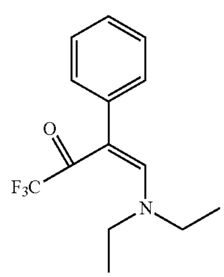 [SMILES: CCN(/C=C(\C(=O)C(F)(F)F)c1ccccc1)CC] | 144 | 319 | | 23306 | 860 | 97 |
| 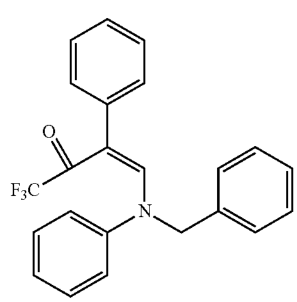 [SMILES: O=C(/C(=C\N(Cc1ccccc1)c1ccccc1)c1ccccc1)C(F)(F)F] | 162 | 329 | 365 | 23495 | 620 | N/A |

TABLE 12-continued
Data for selected compounds of the first aspect. (N/A means compound not tested)
| Structure | No. | $\lambda_{max}$ (nm) | $\lambda_{crit}$ (nm) | ε | E (1%, 1 cm) | Photo-stability (% remains) |
|---|---|---|---|---|---|---|
| 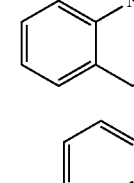 | 163 | 354 | 383 | 26848 | 811 | N/A |
| 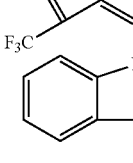 | 164 | 367 | 389 | 35741 | 1127 | 99 |
| 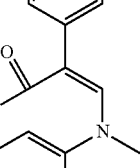 | 172 | 331 | 365 | 22290 | 673 | N/A |
| 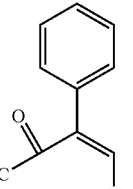 | 177 | 320 | 354 | 23543 | 707 | N/A |
| 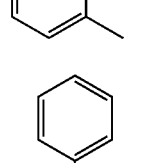 | 149 | 294 | | 14973 | 690 | 6 |

TABLE 12-continued

Data for selected compounds of the first aspect. (N/A means compound not tested)

| Structure | No. | $\lambda_{max}$ (nm) | $\lambda_{crit}$ (nm) | ε | E (1%, 1 cm) | Photo-stability (% remains) |
|---|---|---|---|---|---|---|
| 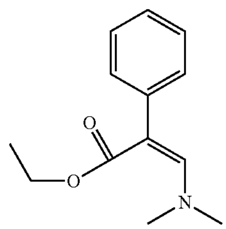 [SMILES: CCOC(=O)/C(=C\N(C)C)c1ccccc1] | 171 | 291 | | 22598 | 1169 | 18 |

Figure 5:
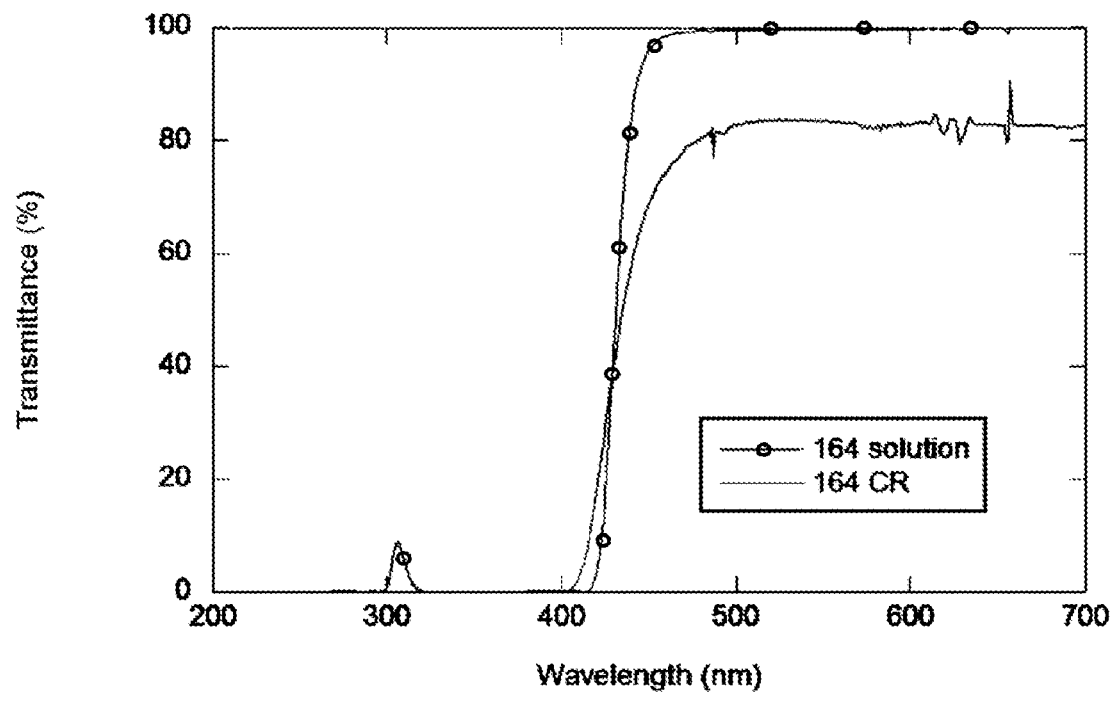
FIG. 5 is a graphical representation of the % transmission of compound 164 in solution versus when incorporated into a cured CR-39 lens (the 154 solution trace is the one with the higher plateau and steeper rise)
Figure 6:
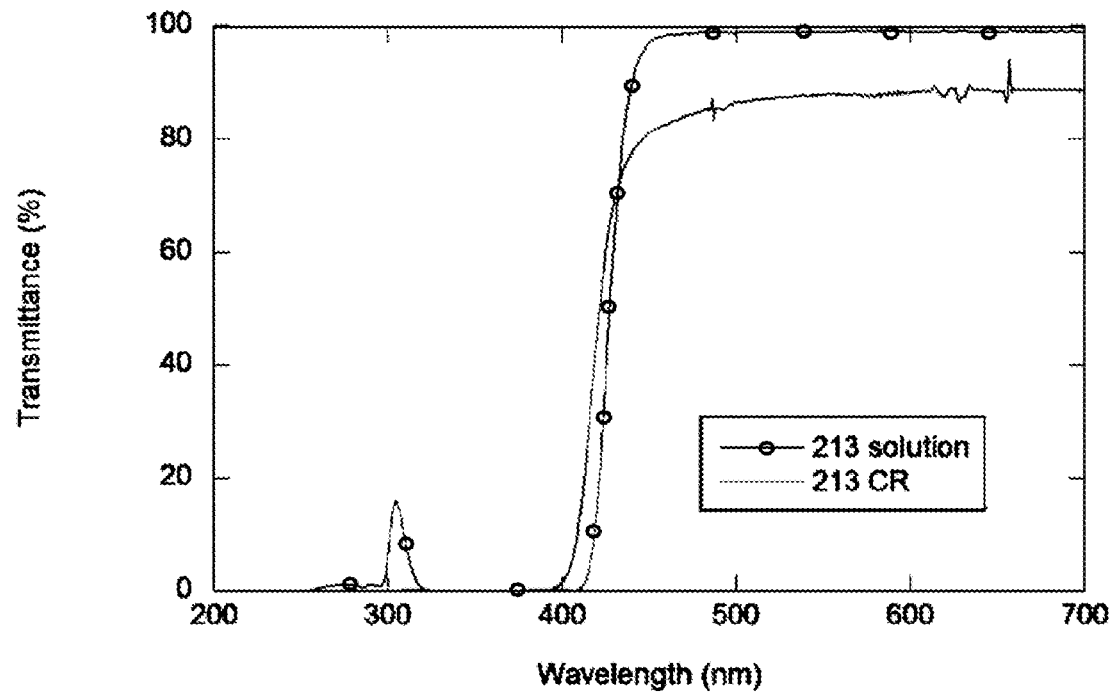
FIG. 6 is a graphical representation of the % transmission of compound 213 in solution versus when incorporated into a cured CR-39 lens (the 213 solution trace is the one with the higher plateau and steeper rise)

As can be seen on moving away from an aromatic nitrogen substituent (142 vs. 144) a lowering in $\lambda_{max}$ is observed but the photostability seen with the parent compound is retained. The results show success in altering absorbance position by changing substituents and demonstrates that the central non-cyclic enamine structure can be used to provide electromagnetic radiation absorbers with a range of absorbing profiles. Of particular interest are compounds 163 and 164 which show an increase in $\lambda_{max}$ on constraining only the nitrogen substituent in a ring i.e. not the double bond. As compound 164 showed a number of desirable properties for further development it was also cast into the same CR-39 lenses as described above for compounds 142 and 143, to evaluate its stability under these conditions. Additionally the dimethyl analogue 213 (structure in table 14) was also evaluated. The CR-39 formulation consisted of (Di(ethylene glycol) bis(allylcarbonate) with benzoyl peroxide (3% wt) and a curing cycle of 70° C. for 18 hours, as previously described. Both compounds 164 (FIG. 5 wherein the higher plateau line is the solution experiment and the lower the CR experiment) and 213 (FIG. 6 wherein the higher plateau line is the solution experiment and the lower the CR experiment) showed a good correlation between the solution phase transmission spectra and that seen in the lenses with only a very slight lowering of the steepness of the curve observed. This indicates good stability to the lens curing conditions and efficacy in lens applications.

172 was synthesised with a pendant allyl group which could be used to incorporate the compound within a polymeric matrix for a range of applications including lenses, glass, coatings and the like. The compounds tested for photostability show an excellent stability profile.

Example 3—General Procedures for Testing of Compounds in Epoxy Resin

In order to test the stability of a number of compounds to a typical epoxy resin curing system, epoxy adhesive packs were obtained (Parfix 5 minute everyday epoxy adhesive, 24 ml). This is a standard 2 part epoxy resin with the first part composed of a viscous Bisphenol-A/epichlorohydrin polymeric reaction product. The second part is a viscous 30% solution of an aminophenol hardener, T (shown below). Epoxy resins cured by 1° and 2° amines are also available.

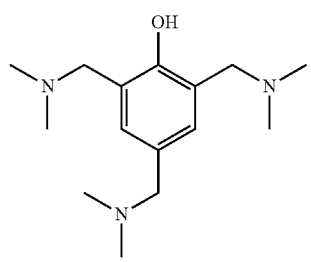

T

To test the stability of the compounds to the curing conditions, a 0.1% wt (1 mg absorber per gram of resin) was prepared and added to a mould comprising a 2 mm thick viton o-ring super glued to a microscope slide. Attempts to cap this with a second microscope slide resulted in the test piece being firmly bonded to both layers of glass and so once the mould was filled, the resin was levelled off with a palette knife and left to cure in the dark overnight (test pieces were touch hard after ca. 10 minutes). Due to difficulties in solubilising the compounds in the mixed resin/hardener in the limited working time as the resin cured; the two barrels of the application syringe were separated with a scalpel allowing the separate application of both parts of the resin system.

As the compounds were found to be generally more soluble in the Bisphenol-A/epichlorohydrin polymeric resin component, a 2% solution of the compounds was prepared in this and then diluted with an equal amount of the hardener. This was then mixed thoroughly and immediately added to the moulds as described above. While the test pieces thus obtained had low transmittance, this was due to the presence of air trapped in the resin (the resin is very viscous, cures quickly and needs to be vigorously stirred to ensure mixing which makes it impossible to remove the air which is thus introduced when using simple lab equipment) but this approach is sufficient purely to determine if the compounds had survived the curing process.

Figure 7:
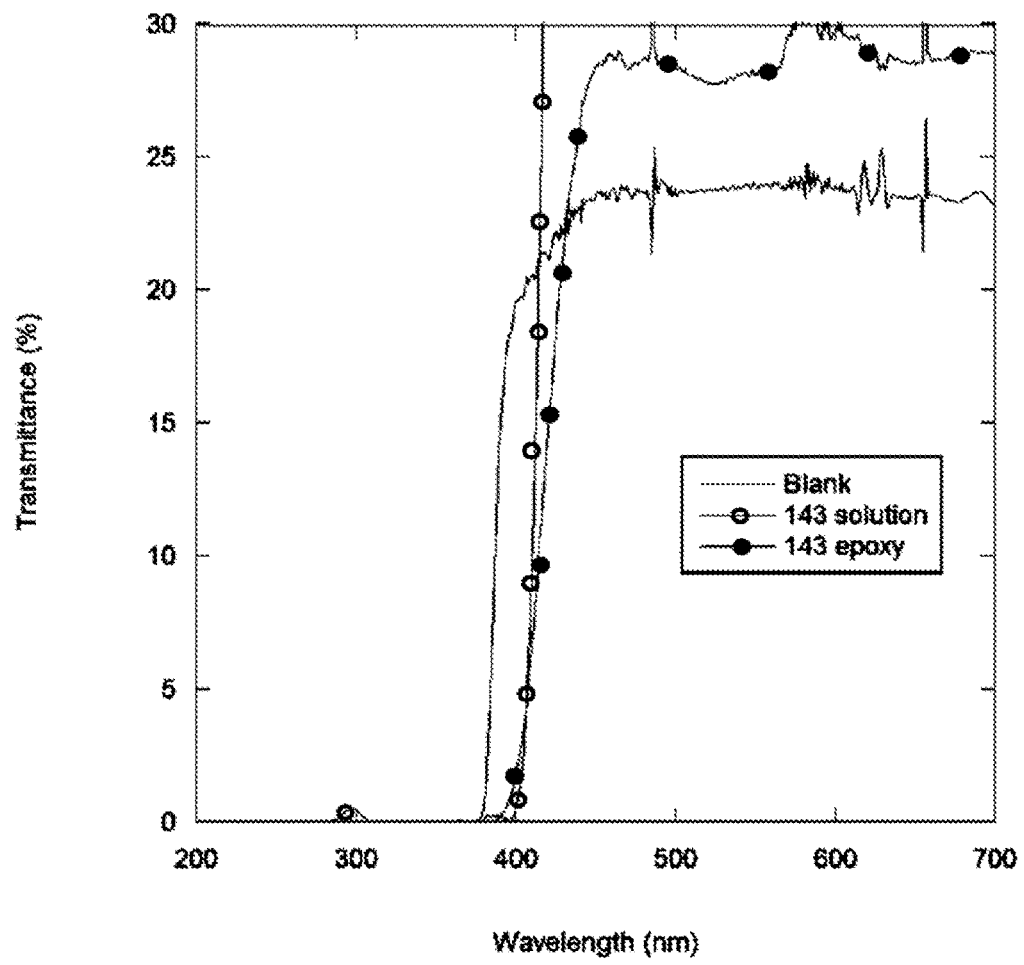
FIG. 7 is a graphical representation showing the transmittance spectra of compound 143 when cast into epoxy resin (the trace with the lowest plateau at 500 nm is the Blank, that with the next lowest is 143 epoxy and the 143 solution trace is the one running off the scale)
Figure 8:
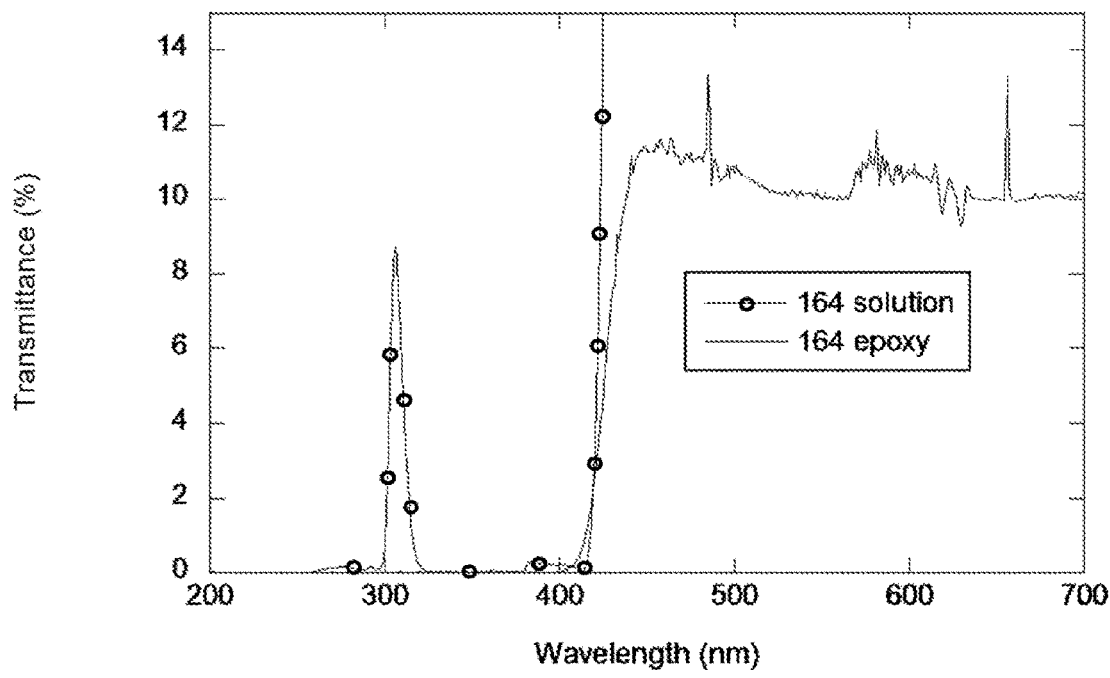
FIG. 8 is a graphical representation showing the transmittance spectra of compound 164 when cast into epoxy resin (the 164 epoxy trace is that with the lowest plateau at 500 nm while the 164 solution trace runs off the scale)

The results of the epoxy testing can be seen in FIG. 7 wherein the lower plateau represents the black, the next highest the epoxy result and the line trending off the chart being the solution phase result (compound 143) and FIG. 8 wherein the plateau line is the epoxy result (compound 164). All of the samples retain significant light blocking beyond that seen for the blank epoxy resin which indicates that the compounds remain intact after curing. Compound 143 shows a close match between the solution phase spectrum and that measured in epoxy resin. This suggests that little or no decomposition occurred.

Example 4—Incorporation of Compounds into Coatings

As a model for the use of the compounds of the first aspect in coatings, a 1% solution by mass (10 mg in 1 g) of the compounds in British Paints oil based polyurethane varnish was applied to the surface of a microscope slide and left to dry overnight in the dark. The transmittance of the slide was then measured before irradiating the sample with a xenon arc lamp (as for the solution phase thin film samples) for two hours and the transmittance re-measured. Slight variations in the thickness of the films obtained would be sufficient to result in variations in transmittance so it was judged to be of equal importance to observe the slope of the samples before and after irradiation as any change here was likely an indicator of decomposition. The varnish itself blocks the transmission of light up to approximately 350-370 nm.

Figure 9:
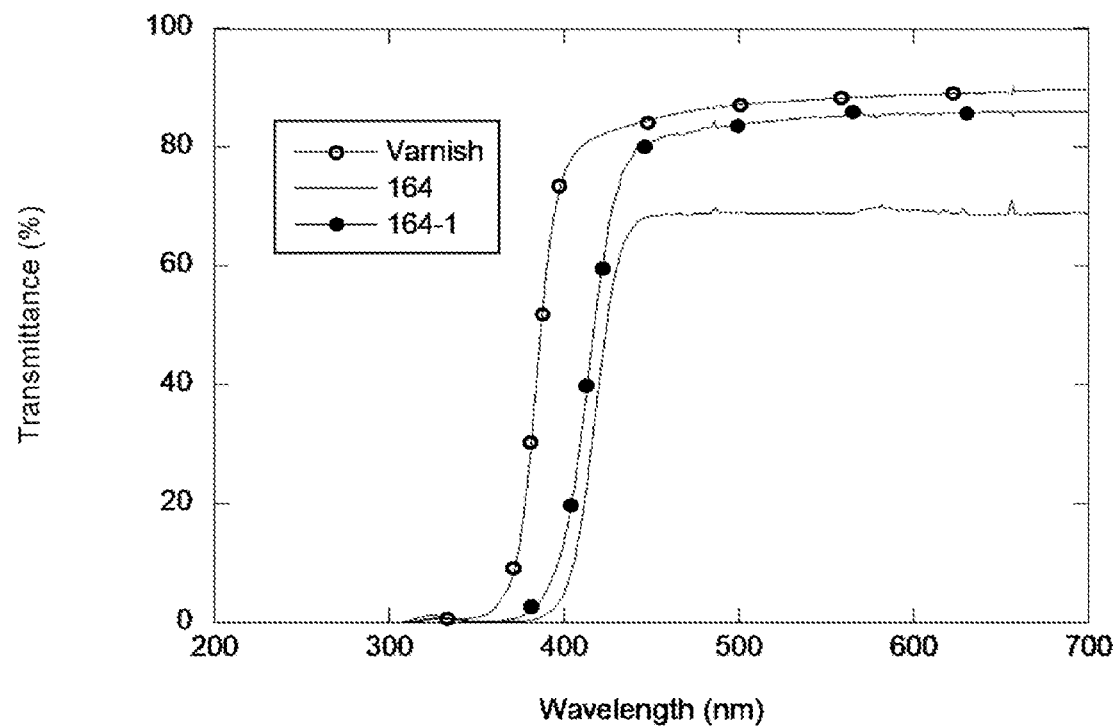
FIG. 9 is a graphical representation showing the transmittance spectra of compound 164 in varnish both before and after irradiation (the 164 trace is that which has the lowest plateau at 500 nm, the 164-1 trace has the next lowest and the Varnish trace is the highest plateau at 500 nm)

Compound 164 was tested and appeared to be largely unscathed by the irradiation with an almost identical slope both before and after exposure to UV as is seen in FIG. 9 wherein the uppermost line is the varnish control, the lowest plateau line is that for the compound before radiation and the middle trace following irradiation.

Example 5—Incorporation of Compounds in a Polymer Matrix

In order to determine the stability of the compounds in a polymer matrix, thin films were cast in Poly(methylmethacrylate) (PMMA). This was achieved by adding the compound in question to a solution of PMMA (Mw 240,000) in DCM and spreading the resulting solution onto a glass slide before evaporation over night to give the desired film. The film was then sandwiched between 2 glass slides to prevent deformation and irradiated. A blank film was found to block light up to approximately 250 nm and the glass microscope slide up to approximately 295 nm (the xenon lamp used for the irradiation was Pyrex filtered and so would be blocking these wavelengths in any case). In this way films of compound 164 were prepared. The films were irradiated for 1 h, 2 h and also left outside exposed to direct sunlight and atmospheric conditions for 3 weeks (Melbourne summer time).

Figure 10:
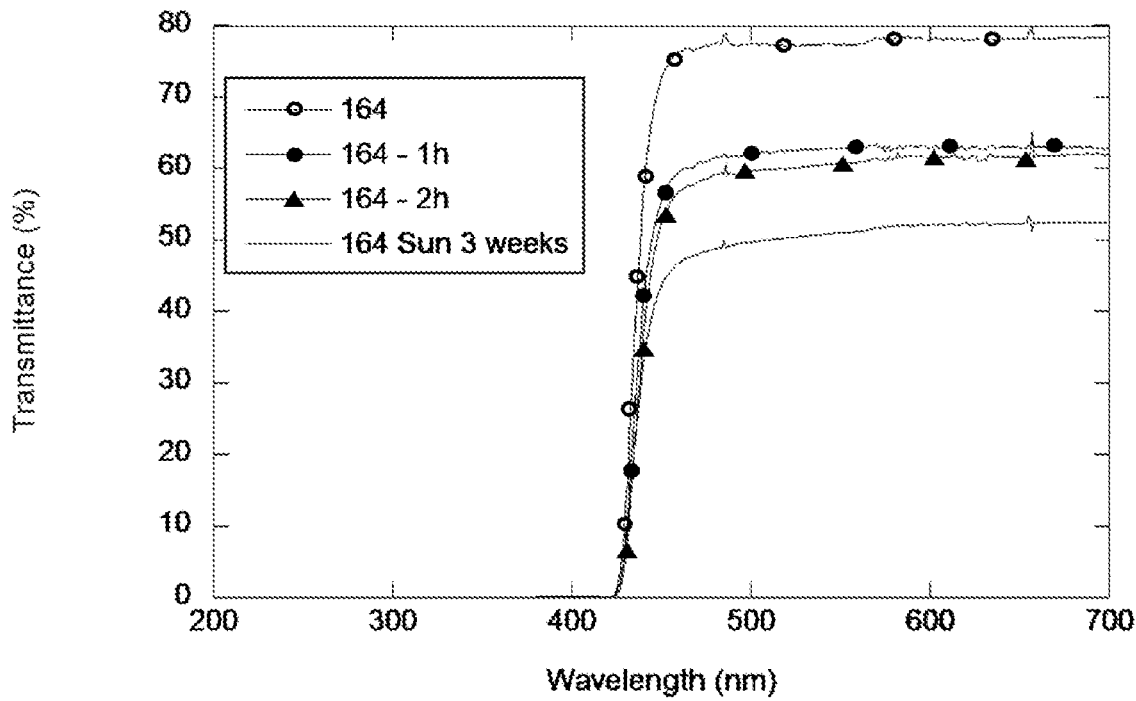
FIG. 10 is a graphical representation showing the transmittance spectra of compound 164 in PMMA both before and after irradiation (the 164 Sun 3 weeks trace is that which has the lowest plateau at 500 nm, the 164-2 h trace has the next lowest, the 164-1 h is next lowest and the 164 trace is the highest plateau at 500 nm)

As can be seen in FIG. 10 (from top plateau line downwards is (i) 164 in PMMA prior to irradiation; (ii) after 1 h irradiation; (iii) 2 h irradiation; and (iv) 3 weeks sun exposure), varnish 164 shows satisfyingly close overlap of all of the spectra for the different exposure periods indicating good incorporation into the matrix thin film without compound deterioration.

Figure 11:
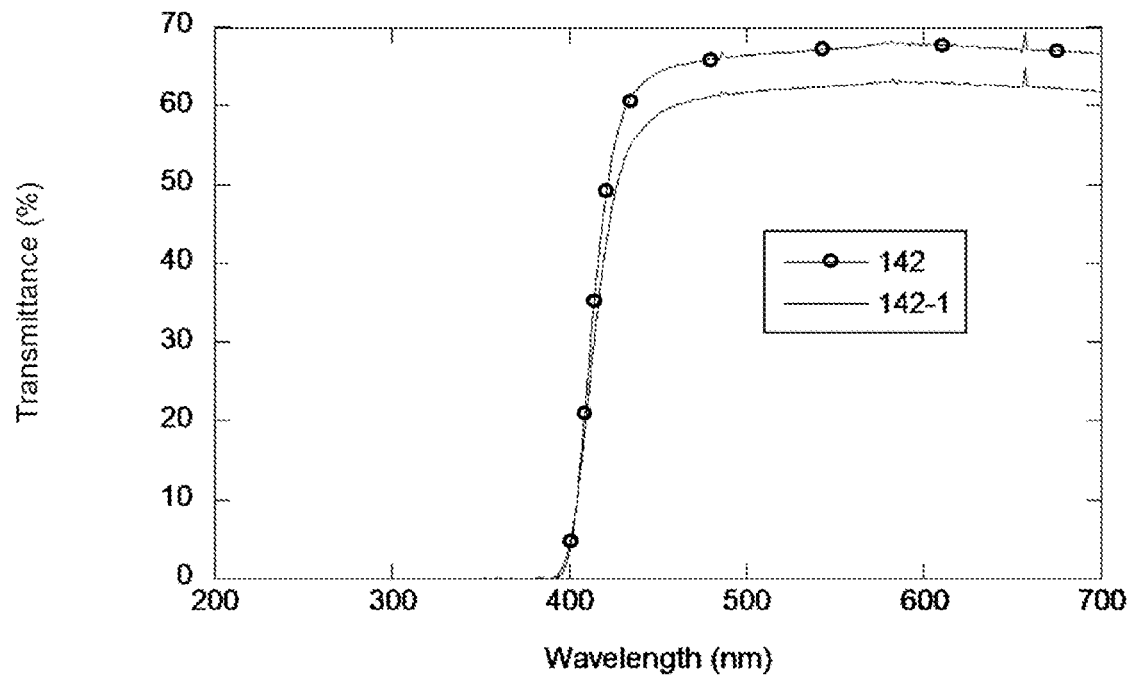
FIG. 11 is a graphical representation showing the transmittance spectra of compound 142 before and after irradiation (the 142 trace has the highest plateau at 500 nm)
Figure 12:
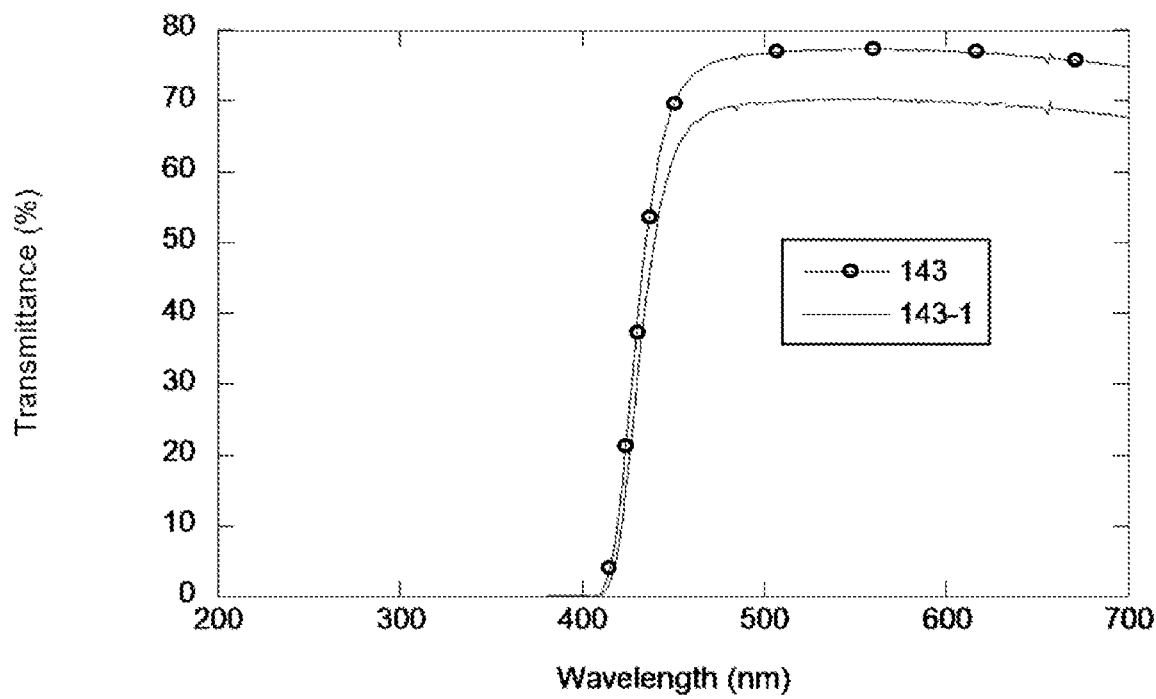
FIG. 12 is a graphical representation showing the transmittance spectra of compound 143 before and after irradiation (the 143 trace has the highest plateau at 500 nm)
Figure 13:
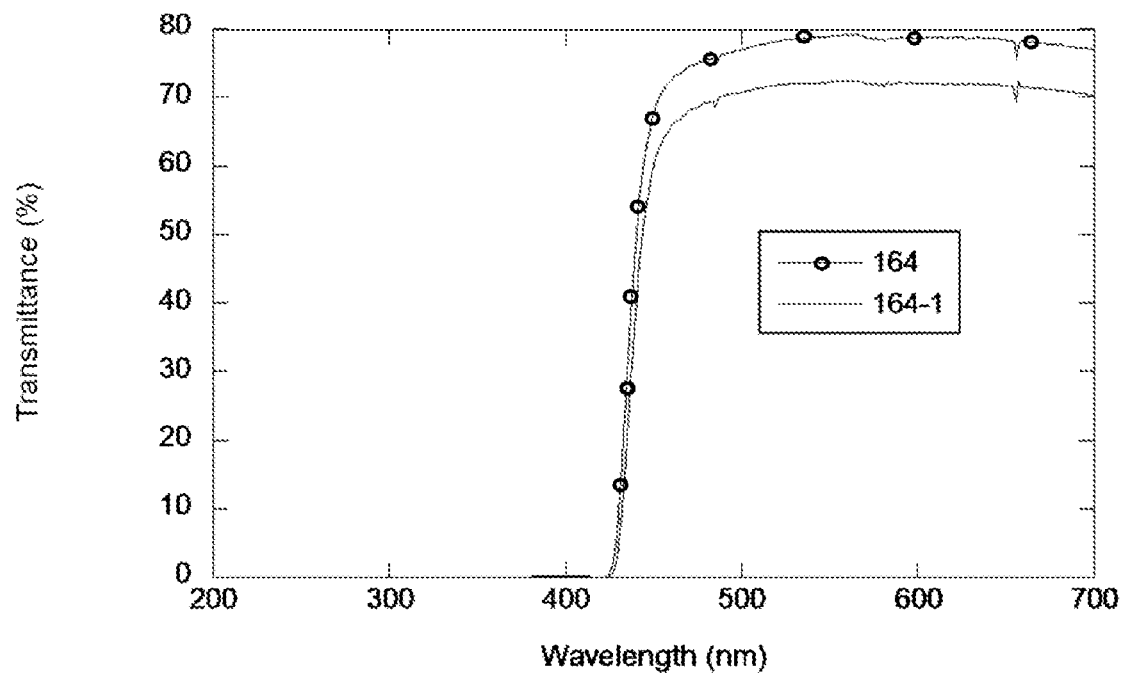
FIG. 13 is a graphical representation showing the transmittance spectra of compound 164 before and after irradiation (the 164 trace has the highest plateau at 500 nm)
Figure 14:
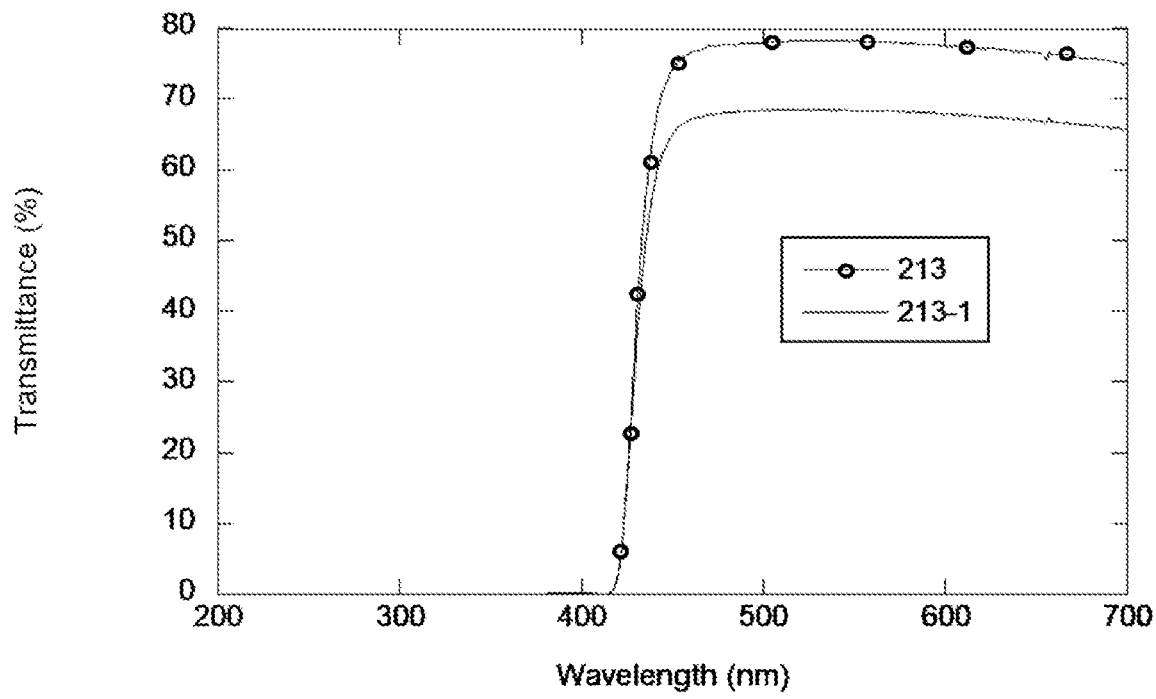
FIG. 14 is a graphical representation showing the transmittance spectra of compound 213 before and after irradiation (the 213 trace has the highest plateau at 500 nm)
Figure 15:
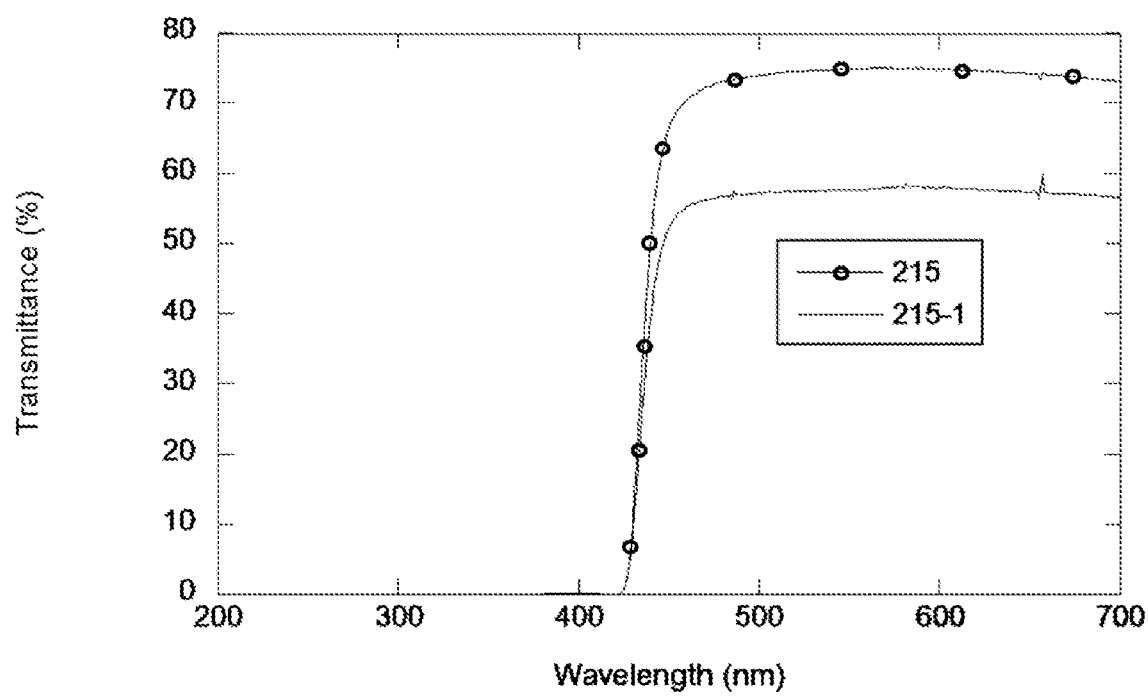
FIG. 15 is a graphical representation showing the transmittance spectra of compound 215 before and after irradiation (the 215 trace has the highest plateau at 500 nm).

In order to gauge longer term photostability, the PMMA film samples were evaluated in a QUV Weatherometer using type A bulbs with solar irradiance at 70° C. for 8 hours followed by heating in the dark under a humid atmosphere at 50° C. for 4 h. The film was then sandwiched between 2 glass slides to prevent deformation and irradiated. The samples were evaluated by a visual comparison and measurement of transmittance spectra. Compounds 142, 143, 164, 213 and 215 all showed little sign of decomposition after irradiation. This clearly indicates the suitability of compounds of the first aspect to incorporation into polymeric matrices and films. The relevant transmission spectra are shown in FIG. 11 (142), FIG. 12 (143), FIG. 13 (164), FIG. 14 (213) and FIG. 15 (215) wherein in all of these figures the lower plateau line represents the result following radiation and the upper line prior to irradiation.

Further compound data is shown in the tables (13 to 15) below:

TABLE 13

Selected compound data for fluorinated compounds

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 143 | 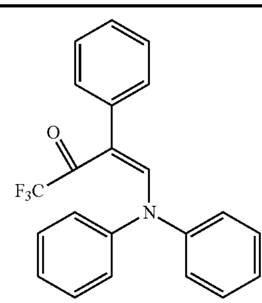 | 367 | 351 | 381 | 27893 | 760 | 402 | 32 | N/A |
| 229 | 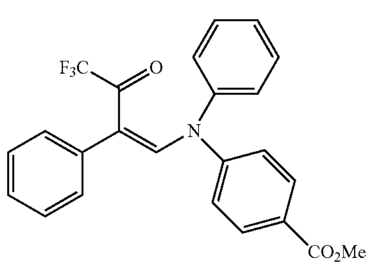 [SMILES: COC(=O)c1ccc(N(/C=C(\C(=O)C(F)(F)F)c2ccccc2)c2ccccc2)cc1] | 425 | 356 | 382 | 33427 | 786 | 403 | 33 | |

TABLE 13-continued

Selected compound data for fluorinated compounds

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 230 | 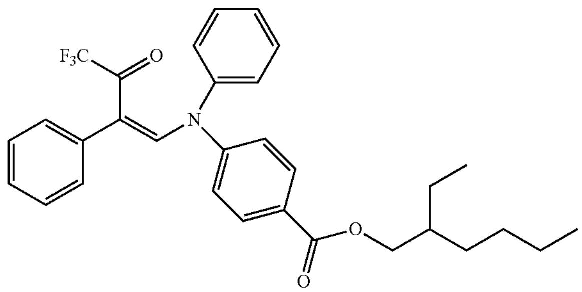 [SMILES: CCCCC(CC)COC(=O)c1ccc(N(/C=C(\C(=O)C(F)(F)F)c2ccccc2)c2ccccc2)cc1] | 523 | 355 | 381 | 27313 | 522 | 398 | 34 | |
| 142 | 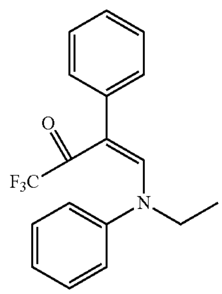 [SMILES: CCN(/C=C(\C(=O)C(F)(F)F)c1ccccc1)c1ccccc1] | 318 | 331 | 365 | 34708 | 1088 | 381 | 29 | 99 |
| 232 | 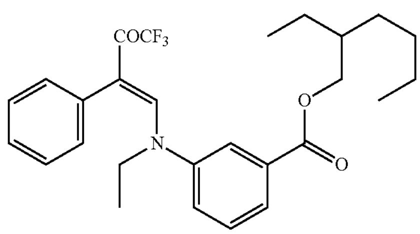 | 475 | 334 | 368 | 20462 | 430 | 373 | 35 | |
| 183 | 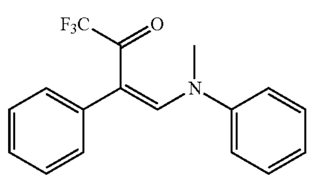 [SMILES: CN(/C=C(\C(=O)C(F)(F)F)c1ccccc1)c1ccccc1] | 305 | 332 | 367 | 23153 | 759 | | | 90 |
| 233 | 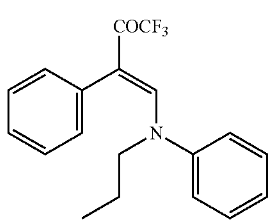 | 333 | 331 | 365 | 24467 | 734 | 380 | 36 | 87 |
| 234 | 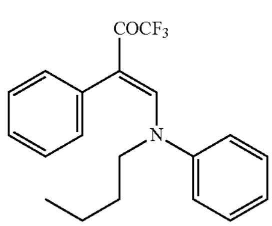 | 347 | 330 | 365 | 24440 | 704 | 381 | 31 | 87 |

TABLE 13-continued

Selected compound data for fluorinated compounds

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 164 | 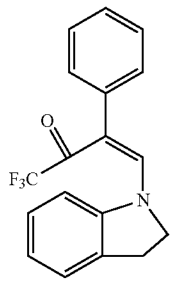 | 317 | 367 | 389 | 35741 | 1127 | 418 | 20 | 99 |
| 235 | 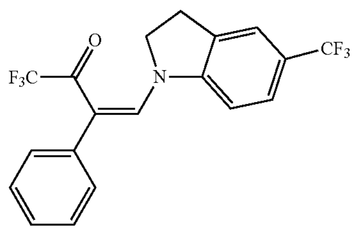 [SMILES: O=C(/C(=C\N1CCc2cc(C(F)(F)F)ccc21)c1ccccc1)C(F)(F)F] | 385 | 361 | 386 | 37158 | 965 | 409 | 19 | |
| 236 | 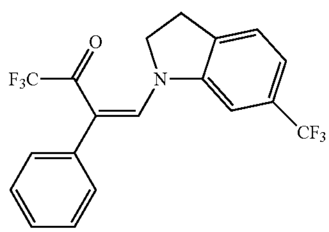 [SMILES: O=C(/C(=C\N1CCc2ccc(C(F)(F)F)cc21)c1ccccc1)C(F)(F)F] | 385 | 364 | 387 | 31379 | 815 | 409 | 19 | |
| 239 | 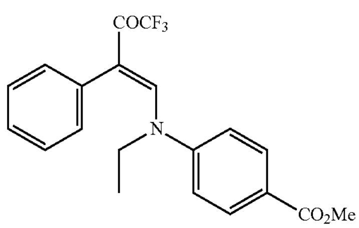 | 377 | 348 | 375 | 25349 | 728 | 391 | 28 | |
| 222 | 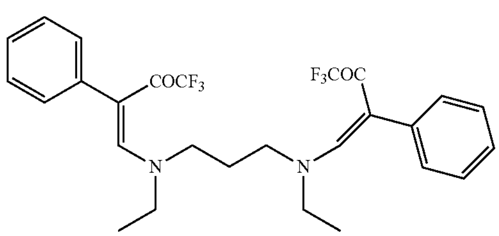 | 526 | 327 | 362 | 53355 | 1014 | 365 | 24 | N/A |
| 144 | 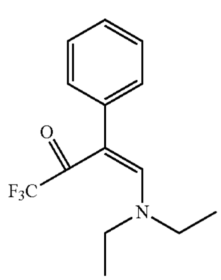 [SMILES: CCN(/C=C(\C(=O)C(F)(F)F)c1ccccc1)CC] | 271 | 319 | 350 | 23306 | 860 | | | 97 |

TABLE 13-continued

Selected compound data for fluorinated compounds

| No. | Structure | Mw | $\lambda_{max}$ (nm) | $\lambda_{crit}$ (nm) | ε | E (1%, 1 cm) | Breakthrough (1% T at 0.1%) | Steepness (nm) | Photostability (%) |
|---|---|---|---|---|---|---|---|---|---|
| 241 | | 540 | 319 | 353 | 44769 | 829 | 365 | | 28 |
| 242 | | 569 | 318 | 353 | 30981 | 544 | 361 | | 52 |

TABLE 14

Further selected compound data for fluorinated compounds

| Structure | No. | $\lambda_{max}$ (nm) | $\lambda_{crit}$ (nm) | ε | E (1%, 1 cm) | Photostability (% remains) |
|---|---|---|---|---|---|---|
| 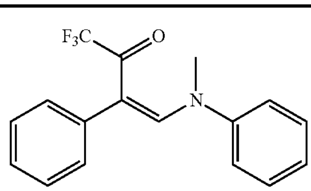 | 183 | 332 | 367 | 23153 | 759 | 90 |

TABLE 14-continued

Further selected compound data for fluorinated compounds

| Structure | No. | λ$_{max}$ (nm) | λ$_{crit}$ (nm) | ε | E (1%, 1 cm) | Photo-stability (% remains) |
|---|---|---|---|---|---|---|
| 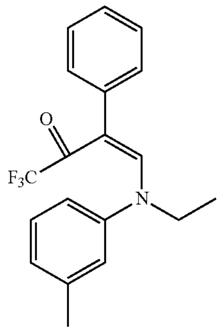 [SMILES: CCN(/C=C(\C(=O)C(F)(F)F)c1ccccc1)c1cccc(C)c1] | 186 | 331 | 367 | 23605 | 709 | |
| 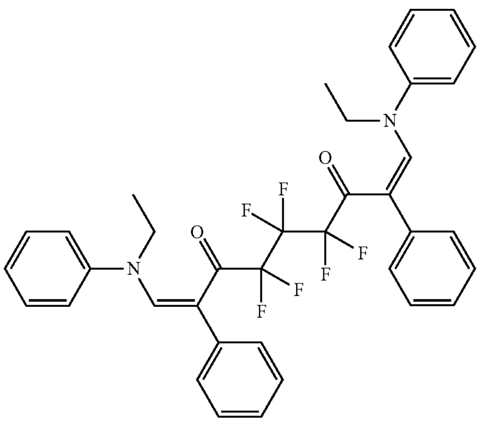 [SMILES: CCN(/C=C(\C(=O)C(F)(F)C(F)(F)C(F)(F)C(=O)/C(=C\N(CC)c1ccccc1)c1ccccc1)c1ccccc1)c1ccccc1] | 190 | 330 | 370 | 40027 | 616 | |
| 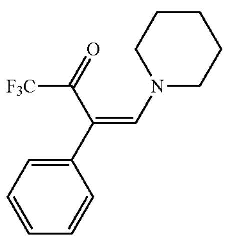 [SMILES: O=C(/C(=C\N1CCCCC1)c1ccccc1)C(F)(F)F] | 192 | 322 | 353 | 25028 | 884 | |
| 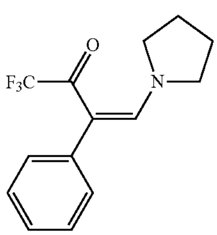 [SMILES: O=C(/C(=C\N1CCCC1)c1ccccc1)C(F)(F)F] | 193 | 323 | 354 | 20673 | 769 | |
| 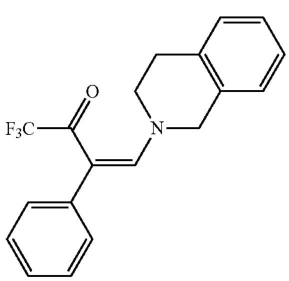 [SMILES: O=C(/C(=C\N1CCc2ccccc2C1)c1ccccc1)C(F)(F)F] | 194 | 321 | 352 | 22743 | 687 | |

TABLE 14-continued

Further selected compound data for fluorinated compounds

| Structure | No. | $\lambda_{max}$ (nm) | $\lambda_{crit}$ (nm) | ε | E (1%, 1 cm) | Photo-stability (% remains) |
|---|---|---|---|---|---|---|
| 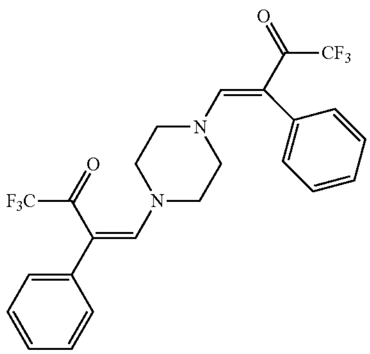 [SMILES: O=C(/C(=C\N1CCN(/C=C(/C(=O)C(F)(F)F)c2ccccc2)CC1)c1ccccc1)C(F)(F)F] | 195 | 339 | 360 | 33248 | 689 | |
| 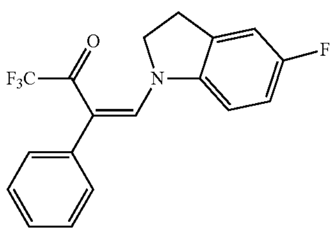 [SMILES: O=C(/C(=C\N1CCc2cc(F)ccc21)c1ccccc1)C(F)(F)F] | 198 | 368 | 389 | 29804 | 890 | |
| 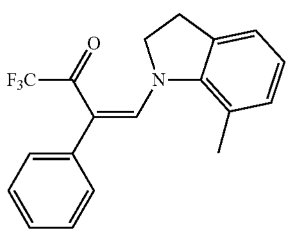 [SMILES: Cc1cccc2c1N(/C=C(\C(=O)C(F)(F)F)c1ccccc1)CC2] | 199 | 360 | 386 | 32273 | 975 | |
| 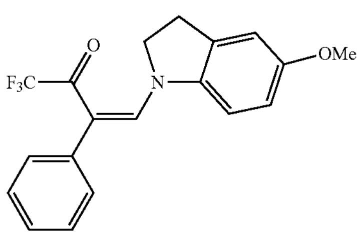 [SMILES: COc1ccc2c(c1)CCN2/C=C(\C(=O)C(F)(F)F)c1ccccc1] | 200 | 381 | 393 | 34855 | 1004 | 91 |
| 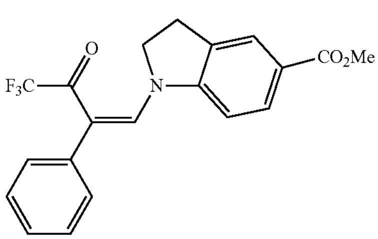 [SMILES: COC(=O)c1ccc2c(c1)CCN2/C=C(\C(=O)C(F)(F)F)c1ccccc1] | 201 | 373 | 391 | 46134 | 1230 | 97 |
| 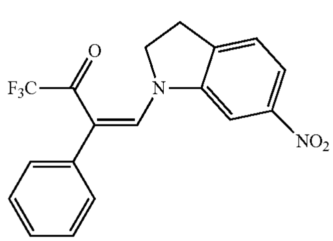 [SMILES: O=C(/C(=C\N1CCc2ccc([N+](=O)[O-])cc21)c1ccccc1)C(F)(F)F] | 202 | 355 | 387 | 32693 | 903 | |

TABLE 14-continued

Further selected compound data for fluorinated compounds

| Structure | No. | $\lambda_{max}$ (nm) | $\lambda_{crit}$ (nm) | $\varepsilon$ | E (1%, 1 cm) | Photo-stability (% remains) |
|---|---|---|---|---|---|---|
| 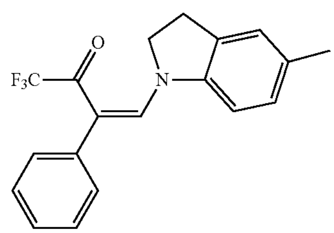 [SMILES: Cc1ccc2c(c1)CCN2/C=C(\C(=O)C(F)(F)F)c1ccccc1] | 205 | 371 | 391 | 36692 | 1108 | |
| 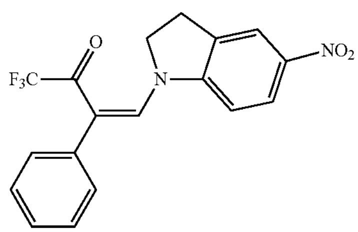 [SMILES: O=C(/C(=C\N1CCc2cc([N+](=O)[O-])ccc21)c1ccccc1)C(F)(F)F] | 206 | 398 | 396 | 50315 | 1390 | |
| 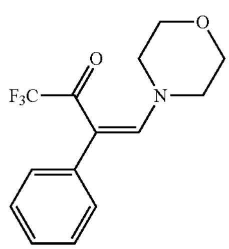 [SMILES: O=C(/C(=C\N1CCOCC1)c1ccccc1)C(F)(F)F] | 209 | 320 | 351 | 24356 | 855 | |
| 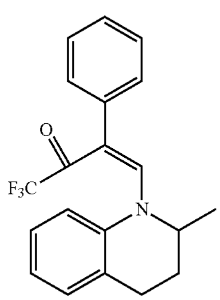 [SMILES: CC1CCc2ccccc2N1/C=C(\C(=O)C(F)(F)F)c1ccccc1] | 211 | 350 | 380 | 28907 | 837 | |
| 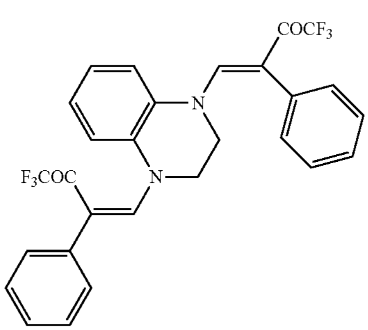 | 212 | 377 | 391 | 40293 | 760 | |

TABLE 14-continued
Further selected compound data for fluorinated compounds
| Structure | No. | $\lambda_{max}$ (nm) | $\lambda_{crit}$ (nm) | ε | E (1%, 1 cm) | Photo-stability (% remains) |
|---|---|---|---|---|---|---|
| 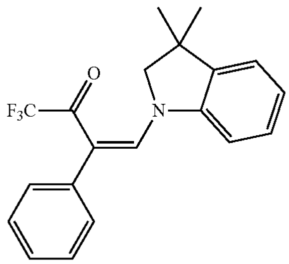 [SMILES: CC1(C)CN(/C=C(\C(=O)C(F)(F)F)c2ccccc2)c2ccccc21] | 213 | 366 | 389 | 29690 | 860 | |
| 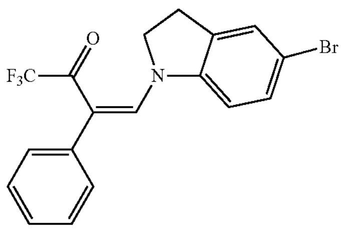 [SMILES: O=C(/C(=C\N1CCc2cc(Br)ccc21)c1ccccc1)C(F)(F)F] | 214 | 371 | 390 | 39265 | 994 | |
| 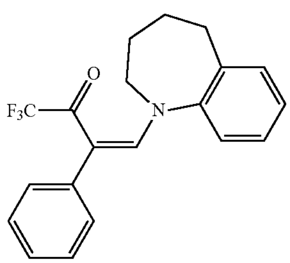 [SMILES: O=C(/C(=C\N1CCCCc2ccccc21)c1ccccc1)C(F)(F)F] | 217 | 324 | 359 | 29114 | 843 | |
| 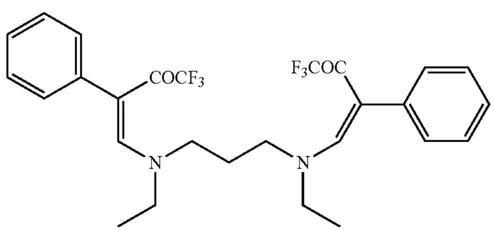 | 222 | 327 | 362 | 53355 | 1014 | |
TABLE 15
Data for selected fluorinated compounds
| Structure | No. | $\lambda_{max}$ (nm) | $\lambda_{crit}$ (nm) | ε | E (1%, 1 cm) | Photo-stability (% remains) |
|---|---|---|---|---|---|---|
| 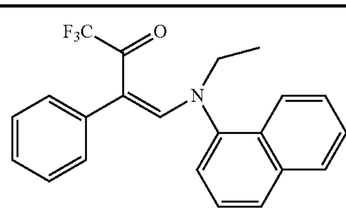 | 189 | 324 | 357 | 23400 | 634 | |

TABLE 15-continued

Data for selected fluorinated compounds

| Structure | No. | λ$_{max}$ (nm) | λ$_{crit}$ (nm) | ε | E (1%, 1 cm) | Photo-stability (% remains) |
|---|---|---|---|---|---|---|
| 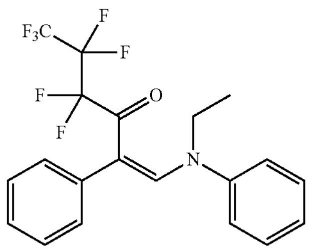 [SMILES: CCN(/C=C(\C(=O)C(F)(F)C(F)(F)C(F)(F)F)c1ccccc1)c1ccccc1] | 191 | 332 | 370 | 18948 | 452 | 95 |
| 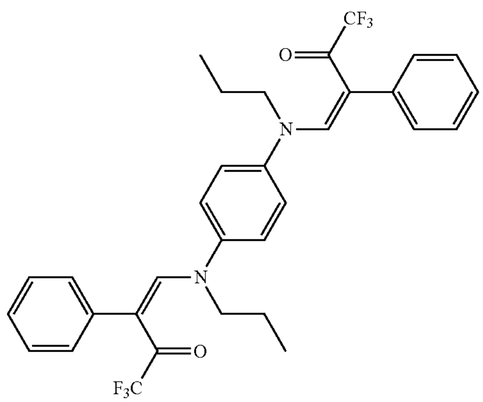 [SMILES: CCCN(/C=C(\C(=O)C(F)(F)F)c1ccccc1)c1ccc(N(/C=C(\C(=O)C(F)(F)F)c2ccccc2)CCC)cc1] | 196 | 344 | 378 | 41997 | 714 | |
| 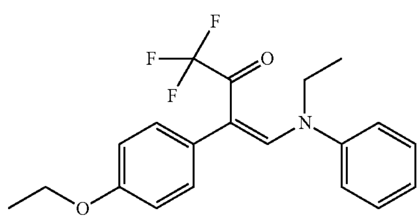 [SMILES: CCOc1ccc(/C(=C/N(CC)c2ccccc2)C(=O)C(F)(F)F)cc1] | 197 | 335 | 369 | 42359 | 1166 | |
| 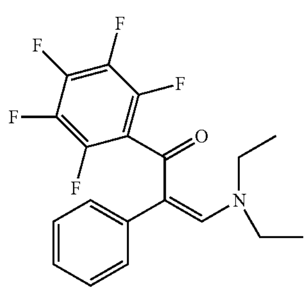 [SMILES: CCN(/C=C(\C(=O)c1c(F)c(F)c(F)c(F)c1F)c1ccccc1)CC] | 203 | 319 (broad) | 356 | 22532 | 611 | 31 |
| 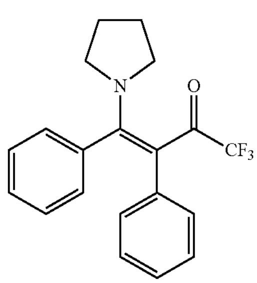 [SMILES: O=C(/C(=C(/c1ccccc1)N1CCCC1)c1ccccc1)C(F)(F)F] | 204 | 363 | 387 | 12357 | 358 | 70 |

TABLE 15-continued

Data for selected fluorinated compounds

| Structure | No. | λ$_{max}$ (nm) | λ$_{crit}$ (nm) | ε | E (1%, 1 cm) | Photo-stability (% remains) |
|---|---|---|---|---|---|---|
| 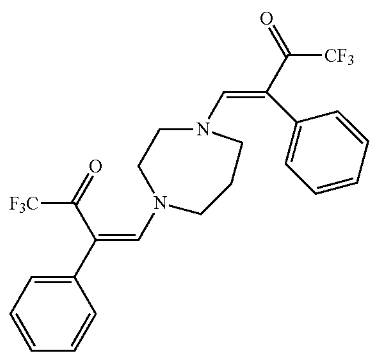 [SMILES: O=C(/C(=C\N1CCCN(/C=C(/C(=O)C(F)(F)F)c2ccccc2)CC1)c1ccccc1)C(F)(F)F] | 210 | 326 | 356 | 40611 | 819 | |
| 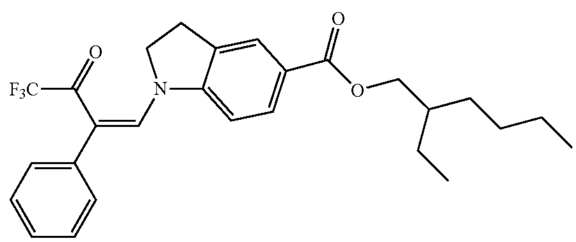 [SMILES: CCCCC(CC)COC(=O)c1ccc2c(c1)CCN2/C=C(\C(=O)C(F)(F)F)c1ccccc1] | 215 | 374 | 391 | 50515 | 1067 | 85 |
| 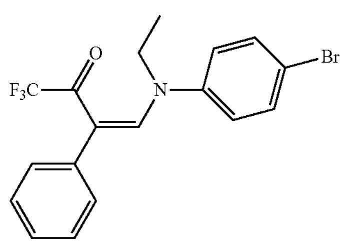 [SMILES: CCN(/C=C(\C(=O)C(F)(F)F)c1ccccc1)c1ccc(Br)cc1] | 216 | 332 | 367 | 25865 | 651 | |
| 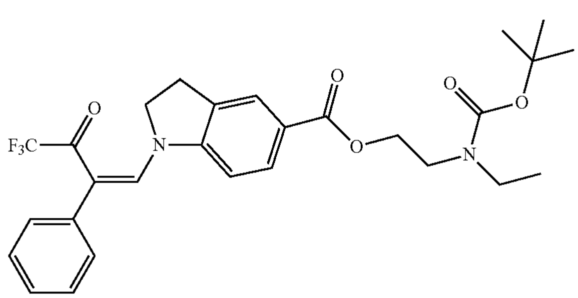 [SMILES: CCN(CCOC(=O)c1ccc2c(c1)CCN2/C=C(\C(=O)C(F)(F)F)c1ccccc1)C(=O)OC(C)(C)C] | 218 | 375 | 391 | 44357 | 833 | |
| 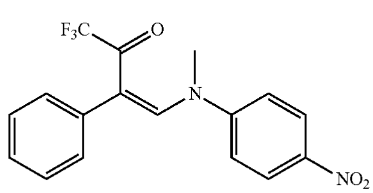 [SMILES: CN(/C=C(\C(=O)C(F)(F)F)c1ccccc1)c1ccc([N+](=O)[O-])cc1] | 219 | 376 | 391 | 24860 | 710 | |

TABLE 15-continued

Data for selected fluorinated compounds

| Structure | No. | $\lambda_{max}$ (nm) | $\lambda_{crit}$ (nm) | $\varepsilon$ | E (1%, 1 cm) | Photo-stability (% remains) |
|---|---|---|---|---|---|---|
| 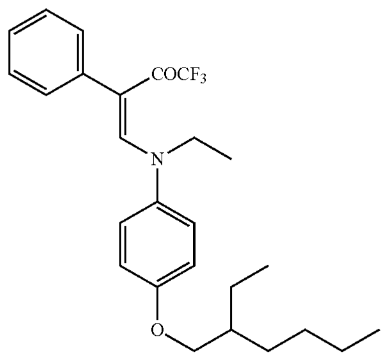 | 220 | 332 | 371 | 23819 | 532 | |
| 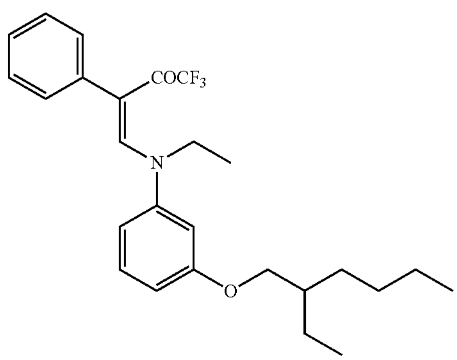 | 221 | 332 | 366 | 21876 | 490 | |
| 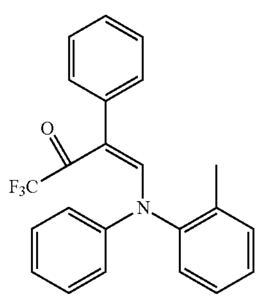 [SMILES: Cc1ccccc1N(/C=C(\C(=O)C(F)(F)F)c1ccccc1)c1ccccc1] | 223 | 344 | 377 | 25885 | 679 | |
| 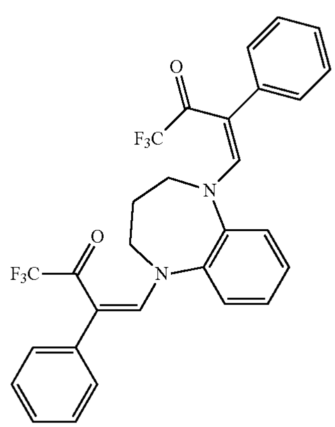 [SMILES: O=C(/C(=C\N1CCCN(/C=C(\C(=O)C(F)(F)F)c2ccccc2)c2ccccc21)c1ccccc1)C(F)(F)F] | 224 | 323 | 366 | 37546 | 690 | 97 |

TABLE 15-continued

Data for selected fluorinated compounds

| Structure | No. | λ$_{max}$ (nm) | λ$_{crit}$ (nm) | ε | E (1%, 1 cm) | Photo-stability (% remains) |
|---|---|---|---|---|---|---|
| 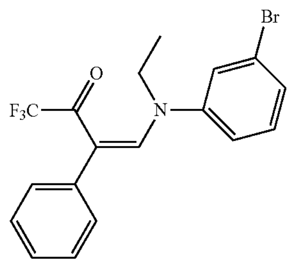 [SMILES: CCN(/C=C(\C(=O)C(F)(F)F)c1ccccc1)c1cccc(Br)c1] | 225 | 332 | 366 | 24181 | 609 | |
| 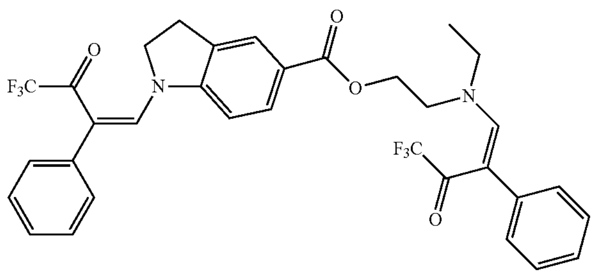 [SMILES: CCN(/C=C(\C(=O)C(F)(F)F)c1ccccc1)CCOC(=O)c1ccc2c(c1)CCN2/C=C(\C(=O)C(F)(F)F)c1ccccc1] | 226 | 374 | 388 | 43151 | 685 | |
| 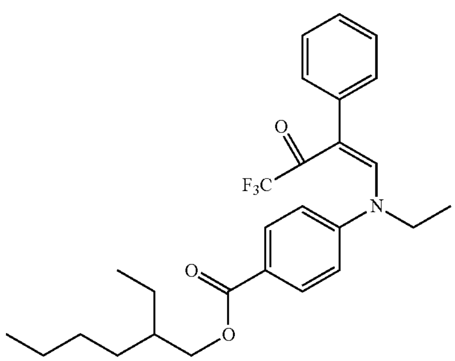 [SMILES: CCCCC(CC)COC(=O)c1ccc(N(/C=C(\C(=O)C(F)(F)F)c2ccccc2)CC)cc1] | 227 | 347 | 374 | 30252 | 646 | 85 |
| 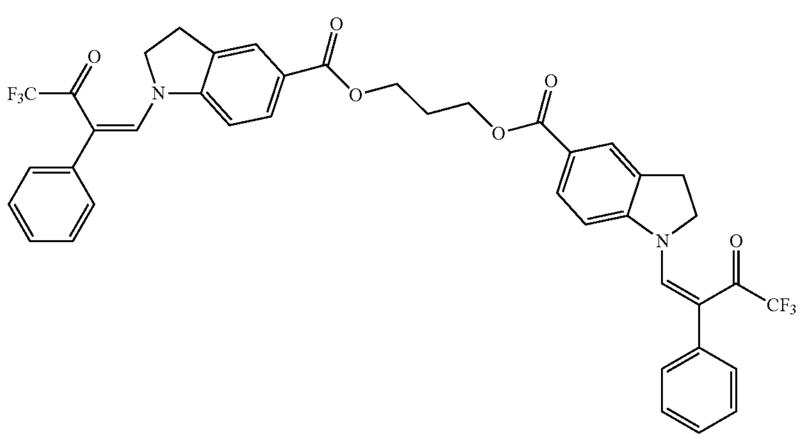 [SMILES: O=C(OCCCOC(=O)c1ccc2c(c1)CCN2/C=C(\C(=O)C(F)(F)F)c1ccccc1)c1ccc2c(c1)CCN2/C=C(\C(=O)C(F)(F)F)c1ccccc1] | 228 | 374 | 391 | 89042 | 1168 | 95 |

TABLE 15-continued

Data for selected fluorinated compounds

| Structure | No. | $\lambda_{max}$ (nm) | $\lambda_{crit}$ (nm) | ε | E (1%, 1 cm) | Photostability (% remains) |
|---|---|---|---|---|---|---|
| [structure with F₃C, O, N, phenyl groups, CO₂Me] | 229 | 356 | 382 | 33427 | | 786 |
| [structure with F₃C, O, N, phenyl groups, 2-ethylhexyl benzoate] | 230 | 355 | 381 | 27313 | | 522 |

Photostability Protocol

The compounds of the first aspect may demonstrate an improved stability upon exposure to electromagnetic radiation, as shown in the photostability data presented. The below approach was used to test this.

1 mL of a 3% solution of the test compound (30 mg of test compound in 1 mL solvent) was prepared in a solvent mix made up of 50% EtOH and 25% capric/caprylic triglyceride and 25% $C_{12}$-$C_{15}$ alkyl benzoate. 50 μL of this solution (containing 1.5 mg of test compound) was added carefully to the centre of a glass microscope slide and the volatile components left to evaporate in the dark for at least 3 hours to give a liquid film. The prepared films were then exposed for 1 hour to an Eimac 150 W xenon arc lamp filtered through Pyrex (15 Amp supply current, samples 19 cm from the lamp) previously allowed to warm up for 15 minutes prior to sample exposure. The irradiation was performed in a fume cupboard where the air flow was sufficient to keep sample T<30° C. One hour's exposure represented a calculated radiation dose (using meter) of approximately 100 MED.

In order to calculate the photostability of the test compounds, the exposed slides were placed in a beaker and rinsed with 2×5 mL EtOH, 1×5 mL MeOH. The combined washings were then added to a 100 mL volumetric flask and made up to 100 mL total volume with methanol. The UV absorbance was then measured in a 10 mm cuvette. The percent stability is measured as the ratio of absorbance at $\lambda_{max}$ for the irradiated sample compared to the unirradiated sample.

The thin films are a good surrogate for testing the stability of a candidate in, for example, a sunscreen formulation as they use cosmetic emollients as solvent and are formed at cosmetically relevant concentrations.

Salt forms of the compounds of the first aspect can be prepared by reaction of the compound with an organic or inorganic acid, using standard methods detailed in the literature.

Examples of acceptable salt forms of the compounds useful according to the invention include acid addition salts. Suitable acid addition salts according to the present invention include organic and inorganic acids and may include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular examples of salt forms include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-sulfonates, and mandelates.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Unless defined otherwise, all technical and scientific terms used herein have the same meaning as would be commonly understood by those of ordinary skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. It is expected that skilled artisans will employ such variations as appropriate and it is considered within the scope and spirit of the present invention for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula I, or a salt or a cis/trans isomer thereof:

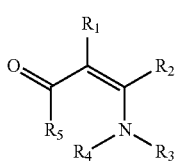

formula I wherein:
$R_1$ is phenyl, which may be substituted or unsubstituted;
$R_2$ is hydrogen;
$R_3$ and $R_4$ together form a 5-membered nitrogen heterocycle fused with a benzene ring, each of which may themselves be substituted or unsubstituted; and
$R_5$ is selected from $C_1$ to $C_{20}$ haloalkyl, $C_1$ to $C_{20}$ haloalkenyl, a fluorine-containing group, $C_1$ to $C_{20}$ secondary or tertiary alkyl wherein secondary and tertiary are defined at the carbon attached to the carbonyl carbon of formula I, $C_2$ to $C_{20}$ alkenyl, ester, amide, $C_1$ to $C_{20}$ alkanoyl, $C_1$ to $C_{20}$ alkenoyl, aryl, $C_5$ to $C_7$ cycloalkenyl, or heterocyclic, each of which groups may be substituted or unsubstituted.

2. The compound of claim 1, wherein $R_3$ and $R_4$ together form a pyrrolidine fused with a benzene ring, each of which may themselves be substituted or unsubstituted.

3. The compound of claim 1, wherein $R_3$ and $R_4$ together form a cyclic structure which includes the nitrogen atom to which they are attached, said cyclic structure being selected from the group consisting of:

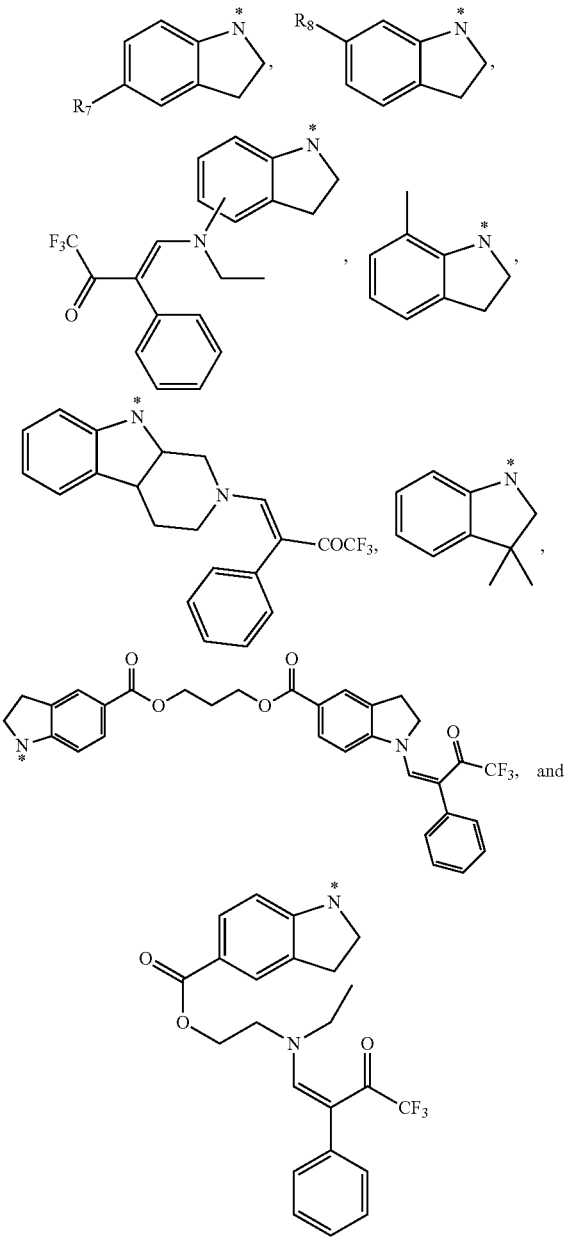

wherein, the asterisk indicates the enamine nitrogen atom to which $R_3$ and $R_4$ are directly attached; and
$R_7$ and $R_8$ are selected from hydrogen, F, Br, Cl, $C_1$ to $C_{20}$ alkyl, $C_1$ to $C_6$ fluoroalkyl, nitro, $C_1$ to $C_6$ alkoxy, —C(O)O—$C_1$ to $C_9$ alkyl, —C(O)O—$C_1$ to $C_4$ alkyl-carbamate, carboxymethyl, carboxyethyl, a divalent presentation of another compound of formula I, —C(O)O-PEG or —C(O)O-PDMS, each of which may be optionally substituted.

4. The compound of claim 1, wherein $R_5$ is selected from $C_1$ to $C_6$ fluoroalkyl, $C_2$ to $C_6$ fluoroalkenyl, $C_5$ or $C_6$ fluoro aryl, $C_1$ to $C_6$ perfluoroalkyl, $C_1$ to $C_6$ secondary or tertiary alkyl, $C_2$ to $C_9$ alkenyl, $C_1$ to $C_9$ alkanoyl, $C_1$ to $C_6$ cyanoalkyl, phenyl, $C_1$ to $C_9$ ester, $C_1$ to $C_9$ amide, and 5- to 7-membered heterocyclic, all of which groups may be substituted or unsubstituted.

5. The compound of claim 1, wherein $R_5$ is selected from the group consisting of:

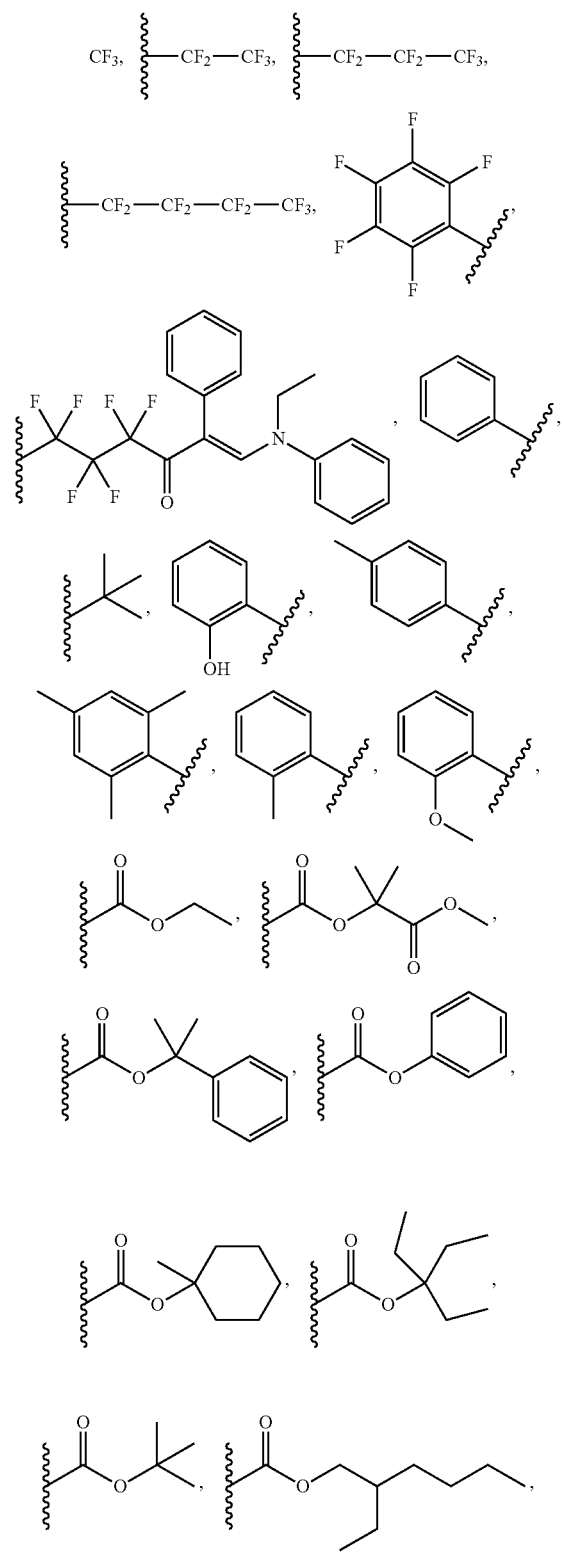

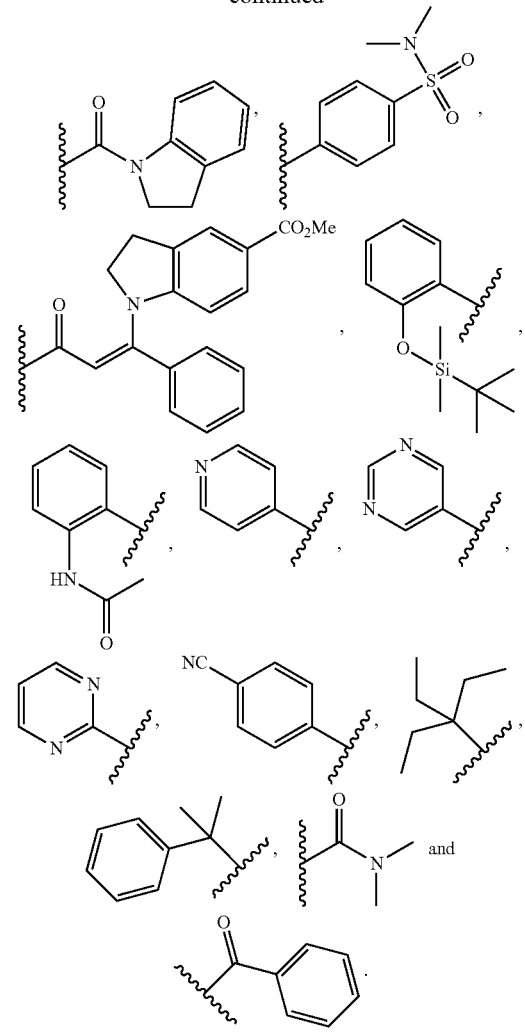

6. A compound of claim 1 of formula II, or a salt or a cis/trans isomer thereof:

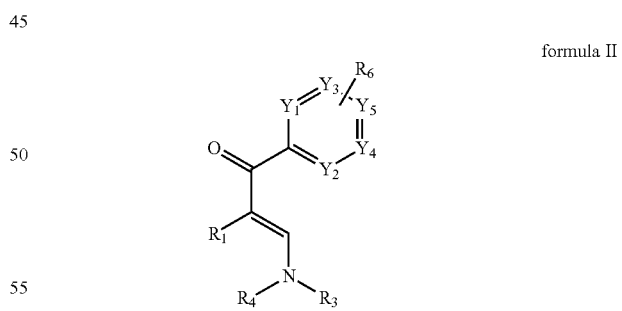

formula II wherein:
$R_1$ is phenyl, which is substituted or unsubstituted;
$R_3$ and $R_4$ together form a 5-membered nitrogen heterocycle fused with a benzene ring, each of which may themselves be substituted or unsubstituted;
$Y_1$, $Y_2$, $Y_3$, $Y_4$ and $Y_5$ are independently selected from a nitrogen or a carbon atom; and
each incidence of $R_6$ is independently selected from hydrogen, hydroxyl, halo, nitro, cyano, $C_1$ to $C_{12}$ alkyl, $C_1$ to $C_{12}$ alcohol, $C_2$ to $C_{12}$ alkenyl, $C_1$ to $C_{12}$ alkoxy, alkoxysilane, $C_1$ to $C_6$ amide, sulphonamide, or $C_1$ to $C_{12}$ haloalkyl, each of which may be substituted or unsubstituted.

7. The compound of claim 6 wherein the compound is a compound of formula IIa, or a salt or a cis/trans isomer thereof:

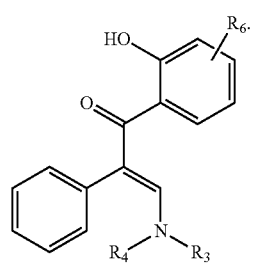

formula IIa

8. A compound of claim 1 of formula VI, or a salt or a cis/trans isomer thereof:

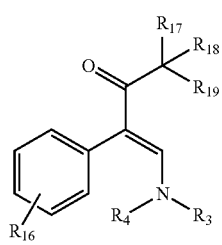

formula VI wherein:
$R_3$ and $R_4$ together form a 5-membered nitrogen heterocycle fused with a benzene ring, each of which may themselves be substituted or unsubstituted; and
$R_{17}$, $R_{18}$ and $R_{19}$ are independently selected from methyl, ethyl or propyl; and
each incidence of $R_{16}$ is independently selected from hydrogen, hydroxyl, halo, nitro, cyano, $C_1$ to $C_{12}$ alkyl, $C_1$ to $C_{12}$ alcohol, $C_2$ to $C_{12}$ alkenyl, $C_1$ to $C_{12}$ alkoxy, sulphonamide, or $C_1$ to $C_{12}$ haloalkyl, each of which may be substituted or unsubstituted.

9. The compound of claim 8, wherein $R_{16}$ is hydrogen and $R_3$ and $R_4$ together form an optionally substituted indoline ring system.

10. A composition comprising a compound of claim 1, or a salt or a cis/trans isomer thereof, and a suitable carrier.

11. A method of protecting a surface or tissue from UV rays including the step of applying a compound of claim 1, or a salt or a cis/trans isomer thereof, to the surface or tissue.

12. The method of claim 11 wherein the surface is selected from a surface of a fabric, clothing material, lens, plastic, timber, masonry or glass, or the tissue is the skin of a mammal.

13. A compound of formula I, or a salt or cis/trans thereof:

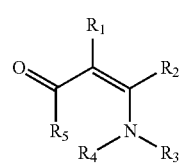

formula I wherein, $R_1$ is phenyl, which may be substituted or unsubstituted;
$R_2$ is hydrogen;
$R_3$ and $R_4$ together form a 5-membered nitrogen heterocycle fused with a benzene ring, each of which may themselves be substituted or unsubstituted;
$R_5$ is selected from the group consisting of $C_1$ to $C_{20}$ haloalkyl, $C_1$ to $C_{20}$ haloalkenyl, a fluorine-containing group, $C_1$ to $C_{20}$ alkyl, $C_2$ to $C_{20}$ alkenyl, ester, amide, $C_1$ to $C_{20}$ alkanoyl, $C_1$ to $C_{20}$ alkenoyl, aryl, $C_5$ to $C_7$ cycloalkenyl, and heterocyclic, each of which groups may be substituted or unsubstituted, and
wherein substituted in the above definitions of $R_1$, $R_3$, $R_4$ and $R_5$ includes substitution with one or more substituents selected from the group consisting of alkyl, alkenyl, alkylalkanoate, aryl, alkylaryl, heteroaryl, heterocyclyl, alkynyl, aroyl, alkanone, cycloalkyl, cycloalkaneone, cycloalkenyl, alkanoyl, alkanoyloxy, alkoxycarbonyl, carbamoyl, carboxyl, halo, cyano, nitro, haloalkyl, N-alkyl, N-aryl and N-heterocyclyl, wherein each of these substituents may themselves be substituted with the same or different substituents.

14. The compound of claim 13, wherein $R_3$ and $R_4$ together form a pyrrolidine fused with benzene ring, which may each be substituted or unsubstituted.

15. The compound of claim 13, wherein $R_3$ and $R_4$ together form a substituted or unsubstituted indoline group.

16. The compound of claim 13, wherein $R_5$ is selected from the group consisting of $C_1$ to $C_{12}$ haloalkyl, $C_2$ to $C_{12}$ haloalkenyl, $C_5$ or $C_6$ aryl, $C_1$ to $C_{12}$ perhaloalkyl, $C_1$ to $C_{12}$ alkyl, $C_1$ to $C_{12}$ alkenyl, $C_1$ to $C_{12}$ alkanoyl, phenyl, ester, amide, and 5-to 7-membered heterocyclic, all of which groups may be substituted or unsubstituted.

17. The compound of claim 1, wherein the compound is selected from the group consisting of:

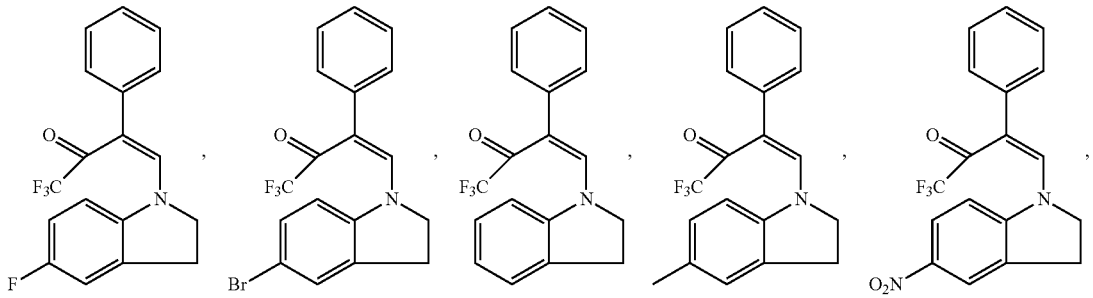

-continued
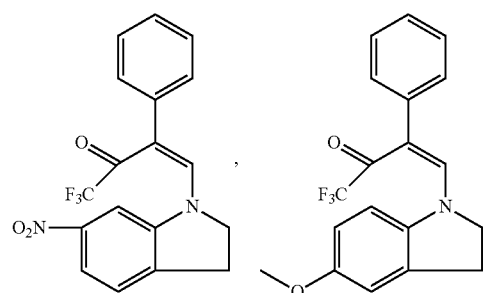
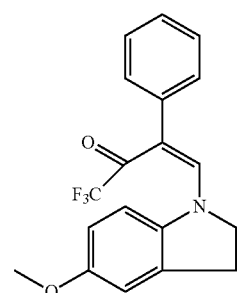
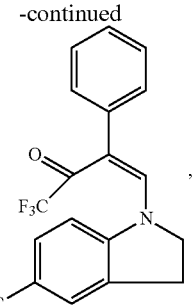
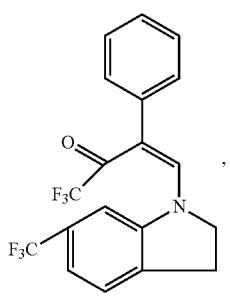
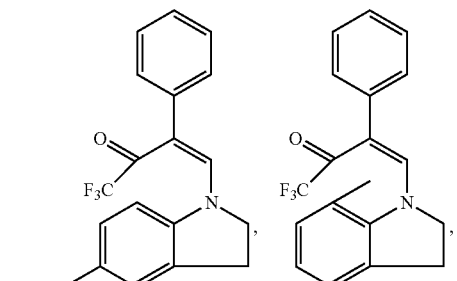
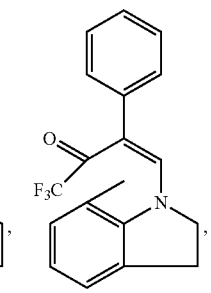
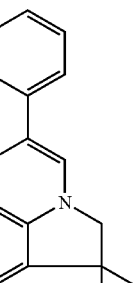
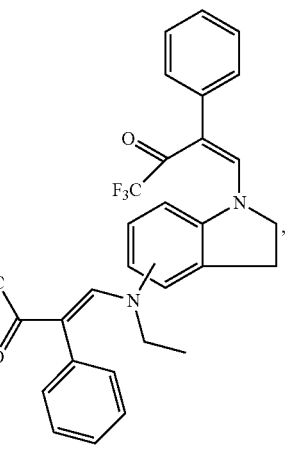
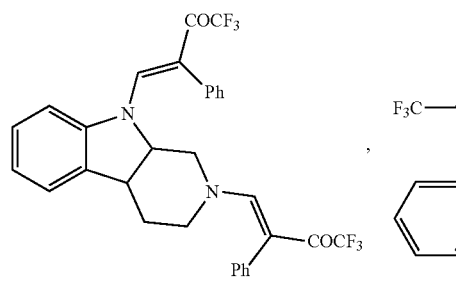
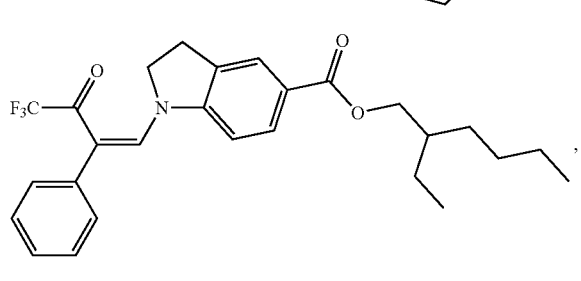
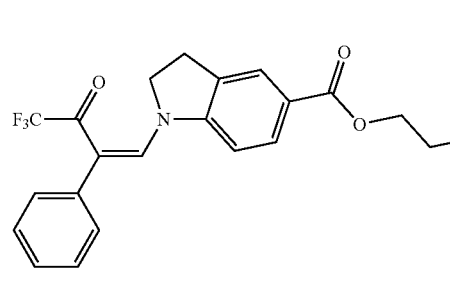
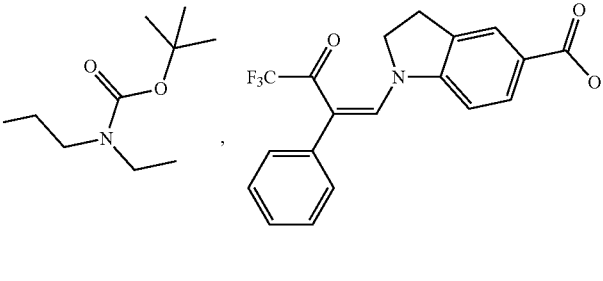
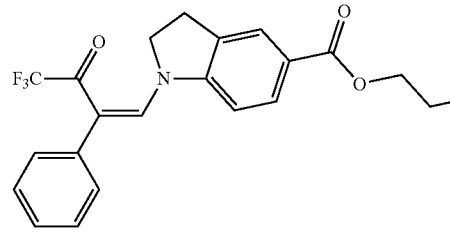
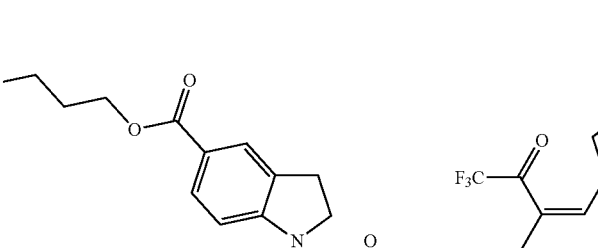
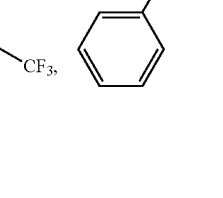

-continued
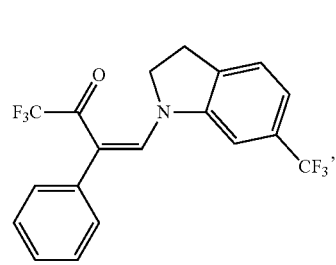
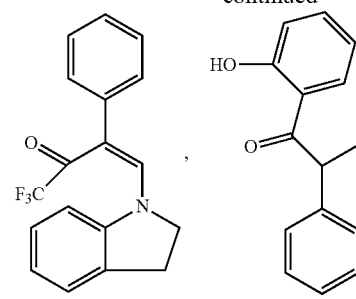
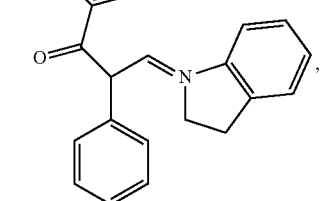
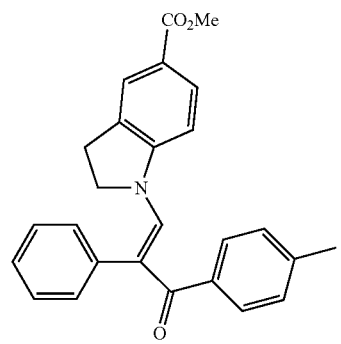
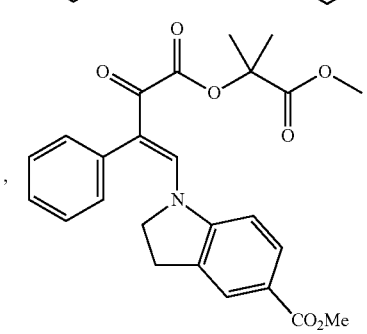
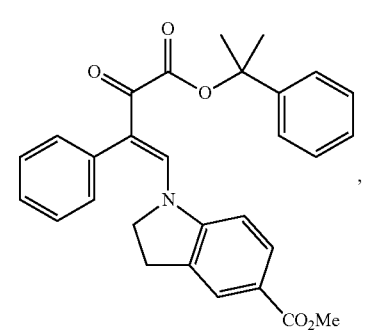
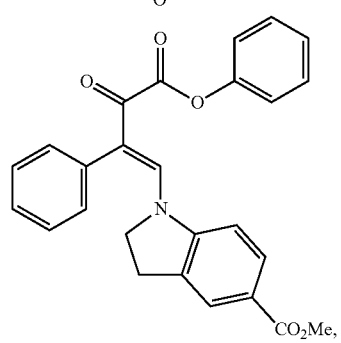
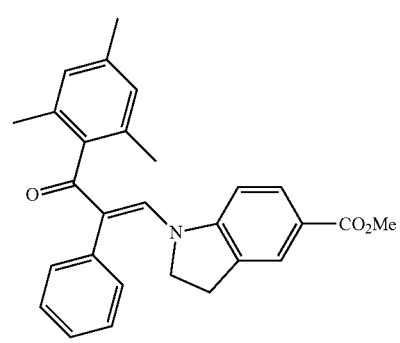
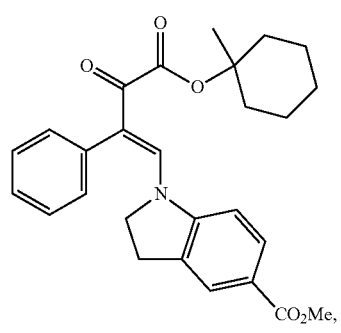
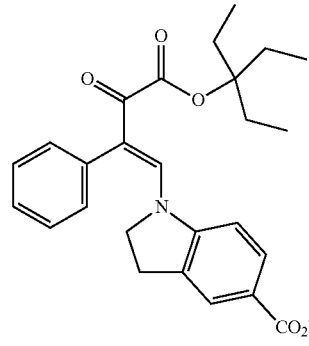
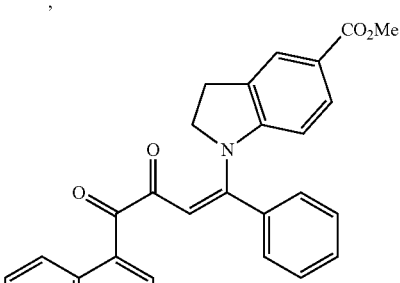
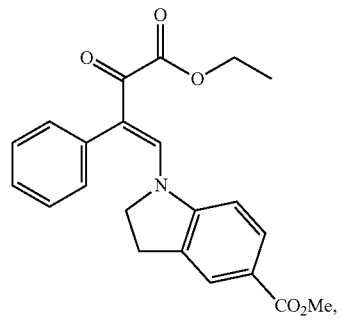
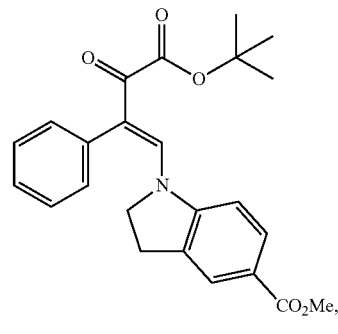

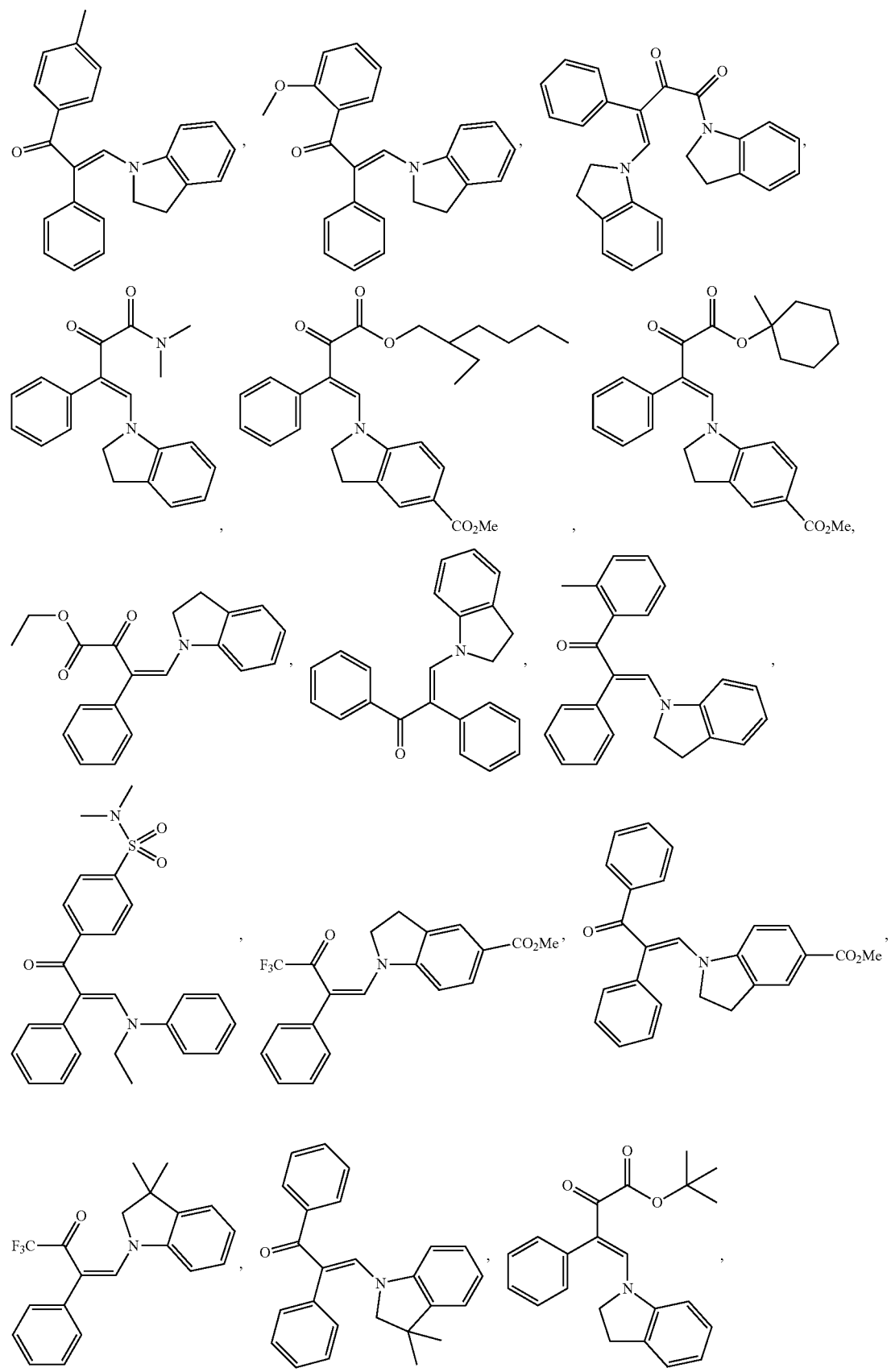

-continued
191
192
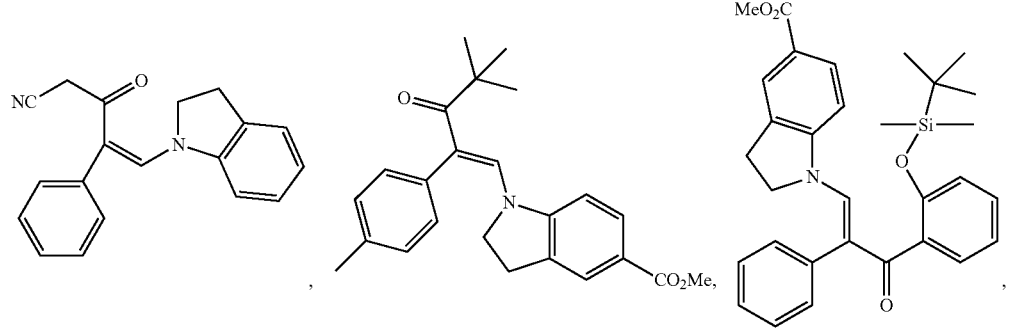
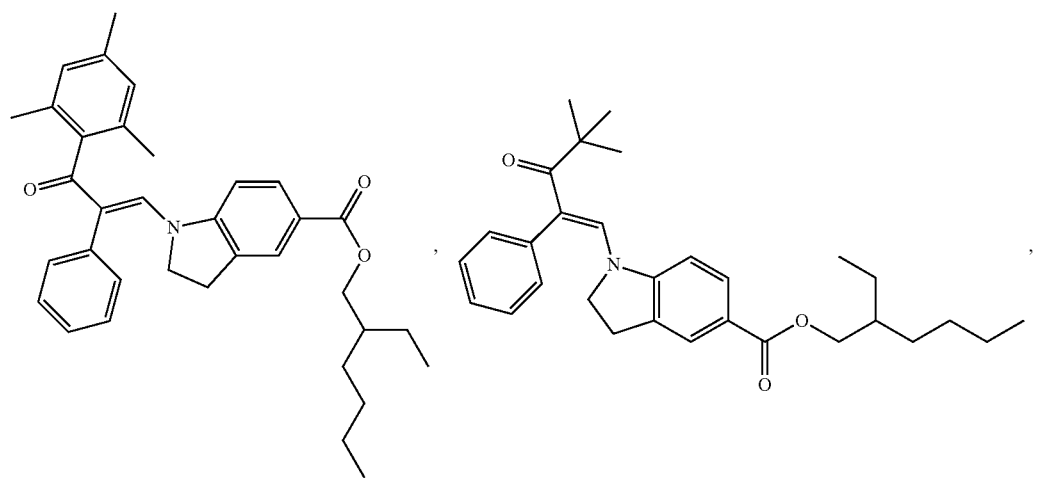
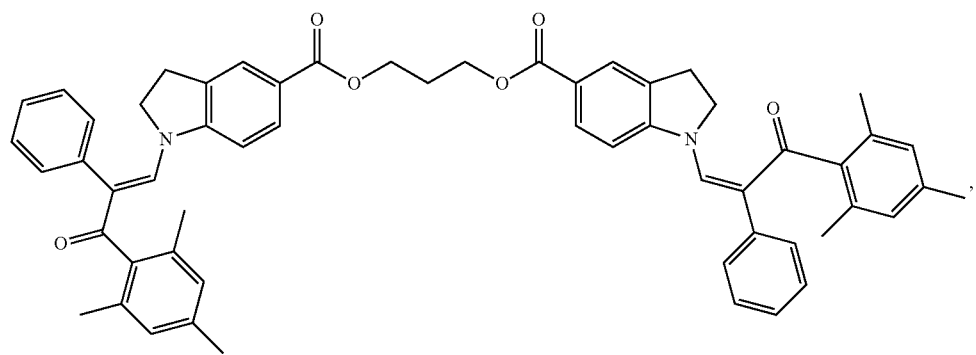
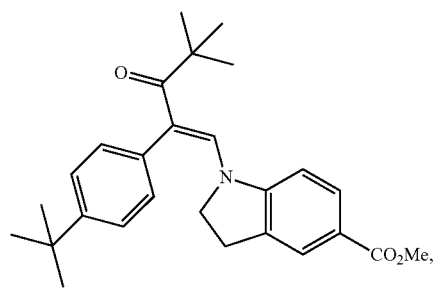

-continued
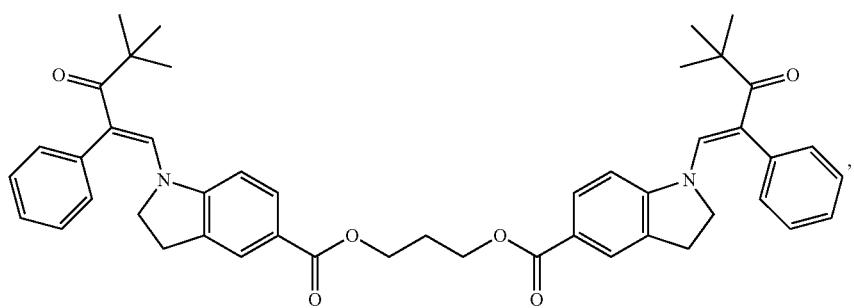
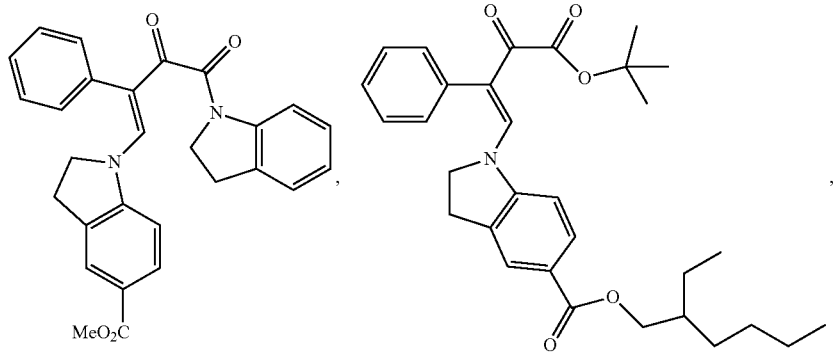
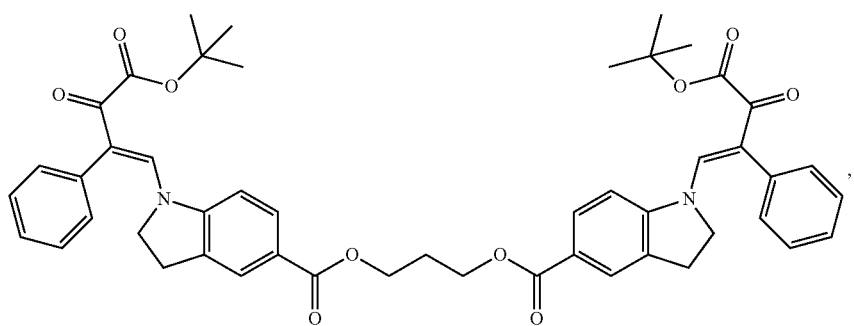
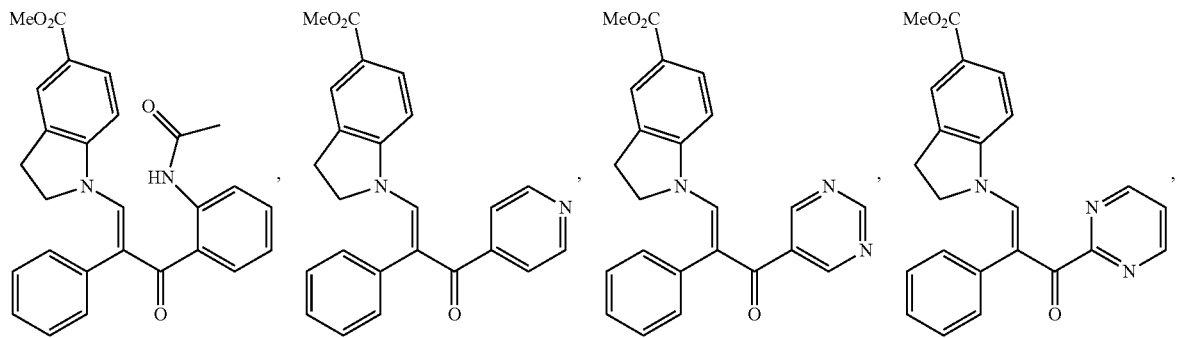
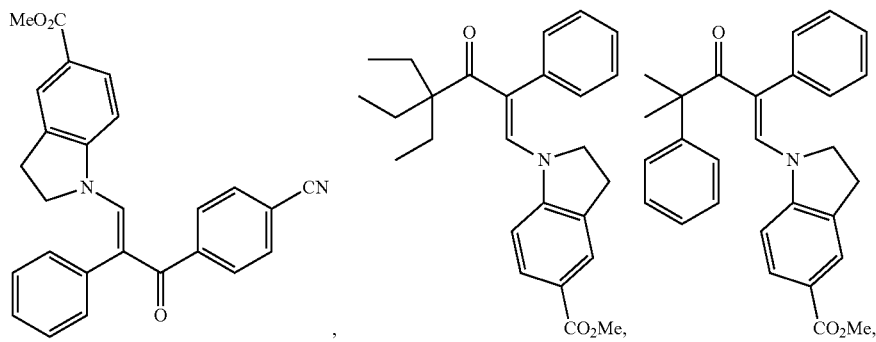

195 196
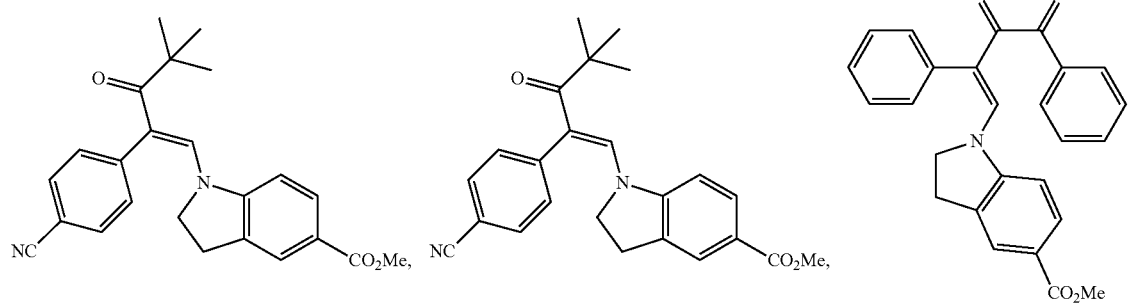
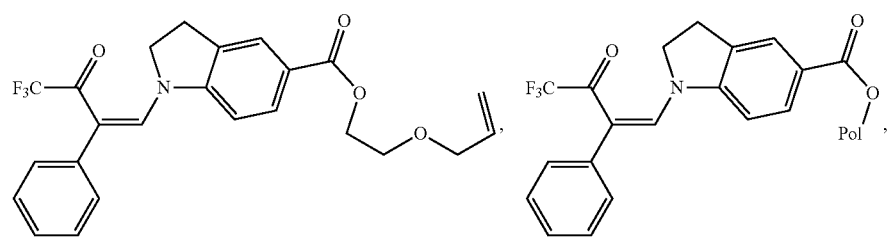
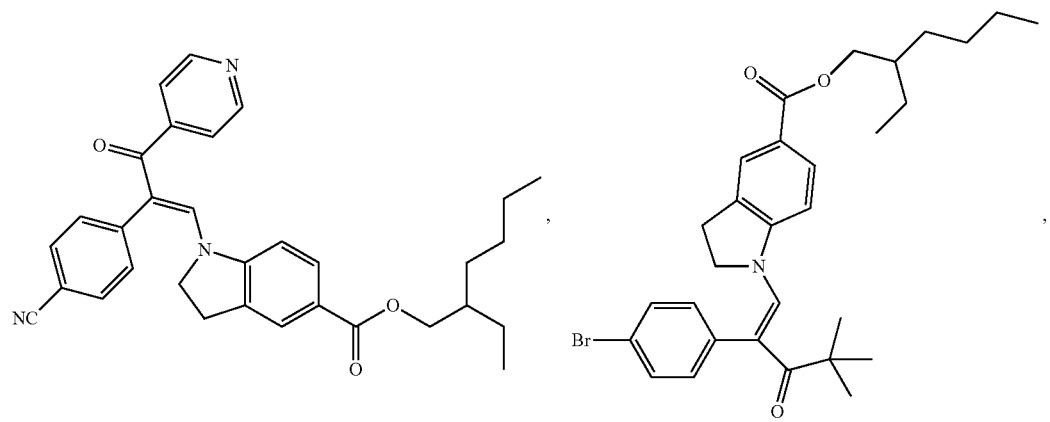
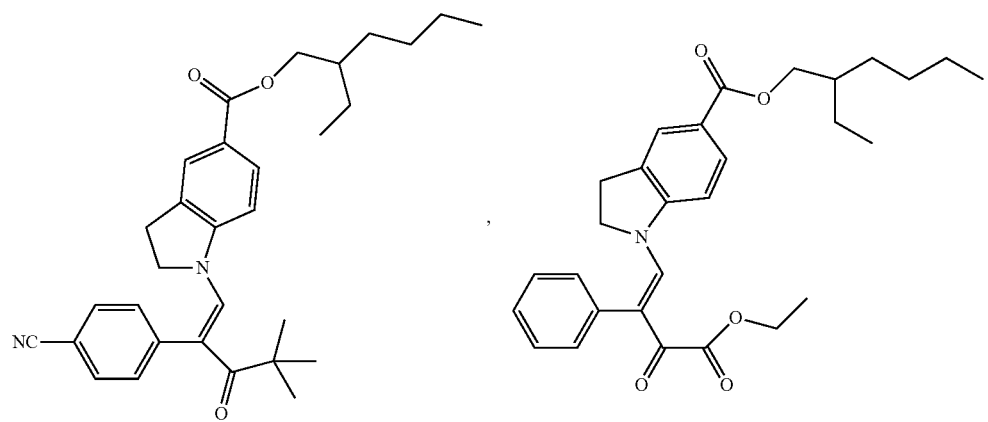

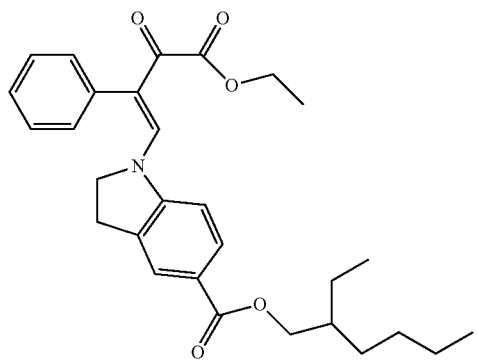
or a salt or a cis/trans isomer thereof, wherein Pol' is selected from PEG, PDMS or $C_6$ to $C_{20}$ alkyl and wherein a bond extending from within a ring structure indicates that bond may be connected directly to any of the ring atoms of that structure.
* * * * *